US012765870B2

(12) United States Patent
Wixey et al.

(10) Patent No.: US 12,765,870 B2
(45) Date of Patent: Oct. 20, 2026

(54) DEVICES AND METHODS FOR COUPLING A CABLE TO A MEDICAL DEVICE

(71) Applicant: Intuitive Surgical Operations, Inc., Sunnyvale, CA (US)

(72) Inventors: Matthew A. Wixey, Trumbull, CT (US); Michael Baldwin, Los Gatos, CA (US); Erik Nelson, Durango, CO (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 764 days.

(21) Appl. No.: 17/798,209

(22) PCT Filed: Feb. 12, 2021

(86) PCT No.: PCT/US2021/017840

§ 371 (c)(1),
(2) Date: Aug. 8, 2022

(87) PCT Pub. No.: WO2021/163468

PCT Pub. Date: Aug. 19, 2021

(65) Prior Publication Data

US 2023/0079266 A1 Mar. 16, 2023

Related U.S. Application Data

(60) Provisional application No. 62/975,927, filed on Feb. 13, 2020, provisional application No. 62/975,928, filed on Feb. 13, 2020.

(51) Int. Cl.

| | |
|---|---|
| ***A61B 17/00*** | (2006.01) |
| ***A61B 34/35*** | (2016.01) |
| *A61B 34/30* | (2016.01) |

(52) U.S. Cl.

CPC ........ *A61B 17/00234* (2013.01); *A61B 34/35* (2016.02); *A61B 2034/305* (2016.02)

(58) Field of Classification Search

CPC ................................ A61B 34/30; A61B 34/71

(Continued)

(56) References Cited

U.S. PATENT DOCUMENTS

| | | | |
|---|---|---|---|
| 2,091,317 | A | 8/1937 | Hill |
| 4,084,594 | A | 4/1978 | Mosior |

(Continued)

FOREIGN PATENT DOCUMENTS

| | | | |
|---|---|---|---|
| AU | 2014208189 | A1 | 4/2015 |
| CN | 101627894 | A | 1/2010 |

(Continued)

OTHER PUBLICATIONS

International Search Report and Written Opinion for Application No. PCT/US2021/017840, mailed on Jul. 28, 2021, 18 pages.

(Continued)

*Primary Examiner* — Allen Porter
*Assistant Examiner* — Jessica L Mullins

(57) ABSTRACT

A tool member is rotatably coupled to a distal end portion of a shaft and includes a drive pulley and a coupling spool. A mechanical structure is coupled to a proximal end portion of the shaft and includes first and second capstans. The first and second capstans each include a first portion and a second portion. A distal portion of the cable is wrapped at least one revolution about the coupling spool. A first proximal end of the cable is wrapped about the second portion of the first capstan such that a second portion crosses over a first portion of the first proximal end of the cable. The second proximal end of the cable is wrapped about the second portion of the second capstan such that a second portion of the second proximal end of the cable crosses over a first portion of the second proximal end of the cable.

20 Claims, 55 Drawing Sheets

(58) Field of Classification Search
USPC .............................................................. 606/1
See application file for complete search history.

(56) References Cited

U.S. PATENT DOCUMENTS 4,319,673 A 3/1982 Kojima
4,751,821 A 6/1988 Birchard
4,785,683 A 11/1988 Buckley et al.
4,850,241 A 7/1989 Buckley et al.
4,903,536 A 2/1990 Salisbury et al.
5,207,691 A 5/1993 Nardella
5,352,235 A 10/1994 Koros et al.
5,373,854 A 12/1994 Kolozsi
5,395,375 A 3/1995 Turkel et al.
5,396,900 A 3/1995 Slater et al.
5,482,054 A 1/1996 Slater et al.
5,496,317 A 3/1996 Goble et al.
5,496,347 A 3/1996 Hashiguchi et al.
5,528,955 A 6/1996 Hannaford et al.
5,531,744 A 7/1996 Nardella et al.
5,575,805 A 11/1996 Li
5,582,617 A 12/1996 Klieman et al.
5,667,354 A 9/1997 Nakazawa
5,713,896 A 2/1998 Nardella
5,730,740 A 3/1998 Wales et al.
5,792,135 A 8/1998 Madhani et al.
5,792,165 A 8/1998 Klieman et al.
5,797,938 A 8/1998 Paraschac et al.
5,800,449 A 9/1998 Wales
5,807,377 A 9/1998 Madhani et al.
5,817,128 A 10/1998 Storz
5,855,583 A 1/1999 Wang et al.
5,876,325 A 3/1999 Mizuno et al.
6,197,017 B1 3/2001 Brock et al.
6,206,903 B1 3/2001 Ramans
6,237,604 B1 5/2001 Burnside et al.
6,273,860 B1 8/2001 Kostylev et al.
6,309,397 B1 10/2001 Julian et al.
6,331,181 B1 12/2001 Tierney et al.
6,394,998 B1 5/2002 Wallace et al.
6,554,844 B2 4/2003 Lee et al.
6,623,482 B2 9/2003 Pendekanti et al.
6,685,698 B2 2/2004 Morley et al.
6,817,974 B2 11/2004 Cooper et al.
6,840,938 B1 1/2005 Morley et al.
6,843,793 B2 1/2005 Brock et al.
6,949,106 B2 9/2005 Brock et al.
6,964,662 B2 11/2005 Kidooka
6,994,708 B2 2/2006 Manzo
7,083,571 B2 8/2006 Wang et al.
7,090,683 B2 8/2006 Brock et al.
7,125,403 B2 10/2006 Julian et al.
7,147,650 B2 12/2006 Lee
7,169,141 B2 1/2007 Brock et al.
7,214,230 B2 5/2007 Brock et al.
7,331,967 B2 2/2008 Lee et al.
7,338,513 B2 3/2008 Lee et al.
7,371,210 B2 5/2008 Brock et al.
7,608,083 B2 10/2009 Lee et al.
7,824,401 B2 11/2010 Manzo et al.
7,935,130 B2 5/2011 Williams
7,963,913 B2 6/2011 Devengenzo et al.
8,142,447 B2 3/2012 Cooper et al.
8,224,484 B2 7/2012 Swarup et al.
8,317,746 B2 11/2012 Sewell et al.
8,323,297 B2 12/2012 Hinman et al.
8,444,631 B2 5/2013 Yeung et al.
8,479,969 B2 7/2013 Shelton, IV
8,506,555 B2 8/2013 Ruiz Morales
8,540,748 B2 9/2013 Murphy et al.
8,551,115 B2 10/2013 Steger et al.
8,573,465 B2 11/2013 Shelton, IV
8,597,280 B2 12/2013 Cooper et al.
8,602,288 B2 12/2013 Shelton, IV et al.
8,758,392 B2 6/2014 Crainich
8,771,270 B2 7/2014 Burbank
8,800,838 B2 8/2014 Shelton, IV
8,808,166 B2 8/2014 Hosaka
8,821,480 B2 9/2014 Burbank
8,887,595 B2 11/2014 Williams et al.
8,939,963 B2 1/2015 Rogers et al.
9,002,518 B2 4/2015 Manzo et al.
9,028,494 B2 5/2015 Shelton, IV et al.
9,078,684 B2 7/2015 Williams
9,198,729 B2 12/2015 Rogers
9,204,923 B2 12/2015 Manzo et al.
9,232,979 B2 1/2016 Parihar et al.
9,259,274 B2 2/2016 Prisco
9,339,341 B2 5/2016 Cooper
9,339,342 B2 5/2016 Prisco et al.
9,358,031 B2 6/2016 Manzo
9,524,022 B2 12/2016 Nakayama
9,533,122 B2 1/2017 Weitzner et al.
9,554,790 B2 1/2017 Bailey et al.
9,572,616 B2 2/2017 Vaughn
9,615,846 B2 4/2017 Prestel
9,664,262 B2 5/2017 Donlon et al.
9,737,373 B2 8/2017 Schuh
9,750,578 B2 9/2017 Alden et al.
9,931,106 B2 4/2018 Au et al.
9,962,228 B2 5/2018 Schuh et al.
9,993,313 B2 6/2018 Schuh et al.
10,130,366 B2 11/2018 Shelton, IV et al.
10,159,473 B2 12/2018 Rogers
10,219,874 B2 3/2019 Yu et al.
10,288,837 B2 5/2019 Miyatani et al.
10,314,583 B2 6/2019 Smith et al.
10,335,177 B2 7/2019 Steger
10,357,321 B2 7/2019 Donlon et al.
10,470,830 B2 11/2019 Hill et al.
10,478,163 B2 11/2019 Prisco et al.
10,478,256 B2 11/2019 Shelton, IV et al.
10,543,051 B2 1/2020 Schena et al.
10,624,709 B2 4/2020 Remm
10,667,873 B2 6/2020 Wallace
10,682,141 B2 6/2020 Moore et al.
10,772,690 B2 9/2020 Prisco
10,779,898 B2 9/2020 Hill et al.
10,799,303 B2 10/2020 Cooper et al.
10,806,530 B2 10/2020 Liao et al.
10,881,280 B2 1/2021 Baez, Jr.
10,932,868 B2 3/2021 Solomon et al.
11,013,566 B2 5/2021 Diel et al.
11,020,112 B2 6/2021 Shelton, IV et al.
11,045,270 B2 6/2021 Shelton, IV et al.
11,076,926 B2 8/2021 Ragosta et al.
11,207,145 B2 12/2021 Lambrecht et al.
11,241,290 B2 2/2022 Waterbury et al.
11,304,770 B2 4/2022 Crews et al.
11,517,397 B2 12/2022 Lambrecht et al.
2002/0111621 A1 8/2002 Wallace et al.
2002/0111635 A1 8/2002 Jensen et al.
2003/0068607 A1 4/2003 Gregorio et al.
2004/0260198 A1 12/2004 Rothberg et al.
2005/0042943 A1 2/2005 Mocivnik et al.
2005/0119527 A1 6/2005 Banik et al.
2006/0074415 A1 4/2006 Scott et al.
2006/0184198 A1 8/2006 Bales et al.
2006/0190034 A1 8/2006 Nishizawa et al.
2006/0217742 A1 9/2006 Messerly et al.
2006/0276775 A1 12/2006 Rosenberg et al.
2007/0043338 A1 2/2007 Moll et al.
2007/0093840 A1 4/2007 Pacelli et al.
2007/0208375 A1 9/2007 Nishizawa et al.
2007/0232858 A1 10/2007 Macnamara et al.
2008/0009838 A1 1/2008 Schena et al.
2008/0015566 A1 1/2008 Livneh
2008/0046122 A1 2/2008 Manzo et al.
2008/0065102 A1 3/2008 Cooper
2008/0065105 A1 3/2008 Larkin et al.
2008/0087871 A1 4/2008 Schena et al.
2008/0103491 A1 5/2008 Omori et al.
2008/0167651 A1 7/2008 Tetzlaff et al.
2008/0196533 A1 8/2008 Bergamasco et al.

(56) References Cited

U.S. PATENT DOCUMENTS

2009/0088774 A1 4/2009 Swarup et al.
2009/0110533 A1 4/2009 Jinno et al.
2009/0112230 A1 4/2009 Jinno
2009/0131975 A1 5/2009 Ahlberg et al.
2009/0148263 A1 6/2009 Lee et al.
2009/0198272 A1 8/2009 Kerver et al.
2009/0222022 A1 9/2009 Laporte et al.
2009/0326530 A1 12/2009 Orban, III et al.
2010/0011900 A1 1/2010 Burbank et al.
2010/0011901 A1 1/2010 Burbank
2010/0030238 A1 2/2010 Viola et al.
2010/0170519 A1 7/2010 Romo et al.
2010/0175701 A1 7/2010 Reis et al.
2010/0198253 A1 8/2010 Jinno et al.
2010/0318101 A1 12/2010 Choi et al.
2011/0015648 A1 1/2011 Alvarez et al.
2011/0015650 A1 1/2011 Choi et al.
2011/0065992 A1 3/2011 Bissinger
2011/0071508 A1 3/2011 Duval et al.
2011/0071543 A1 3/2011 Prisco et al.
2011/0118754 A1 5/2011 Dachs, II et al.
2011/0184241 A1 7/2011 Zubiate et al.
2011/0251612 A1 10/2011 Faller et al.
2011/0277775 A1 11/2011 Holop et al.
2011/0295269 A1 12/2011 Swensgard et al.
2011/0295270 A1 12/2011 Giordano et al.
2011/0313405 A1 12/2011 Anderson et al.
2012/0046522 A1 2/2012 Naito
2012/0109186 A1 5/2012 Parrott et al.
2012/0116433 A1 5/2012 Houser et al.
2012/0123441 A1 5/2012 Au et al.
2012/0150144 A1 6/2012 Campbell et al.
2012/0150192 A1 6/2012 Dachs, II et al.
2012/0239060 A1 9/2012 Orban, III et al.
2012/0277663 A1 11/2012 Millman et al.
2012/0289974 A1 11/2012 Rogers et al.
2012/0292367 A1 11/2012 Morgan et al.
2012/0298719 A1 11/2012 Shelton, IV et al.
2013/0046318 A1 2/2013 Radgowski et al.
2013/0079810 A1 3/2013 Isenberg
2013/0123783 A1 5/2013 Marczyk et al.
2013/0140835 A1 6/2013 Stefanchik et al.
2013/0144395 A1 6/2013 Stefanchik et al.
2013/0199327 A1 8/2013 Park et al.
2013/0267950 A1 10/2013 Rosa et al.
2014/0005662 A1 1/2014 Shelton, IV
2014/0005678 A1 1/2014 Shelton, IV et al.
2014/0005708 A1 1/2014 Shelton, IV
2014/0018821 A1 1/2014 Yeung et al.
2014/0073856 A1 3/2014 Stein et al.
2014/0100558 A1 4/2014 Schmitz et al.
2014/0107665 A1 4/2014 Shellenberger et al.
2014/0257333 A1 9/2014 Blumenkranz
2014/0276723 A1 9/2014 Parihar et al.
2014/0276956 A1 9/2014 Crainich et al.
2014/0309625 A1 10/2014 Okamoto et al.
2014/0378994 A1 12/2014 Wang
2015/0005786 A1 1/2015 Burbank
2015/0051034 A1 2/2015 Cooper et al.
2015/0150635 A1 6/2015 Kilroy et al.
2015/0157355 A1 6/2015 Price et al.
2015/0209965 A1* 7/2015 Low ........................ B25J 17/02
901/29
2015/0313676 A1 11/2015 Deodhar
2016/0045770 A1 2/2016 Yamada
2016/0058443 A1 3/2016 Yates et al.
2016/0151115 A1 6/2016 Karguth et al.
2016/0157926 A1 6/2016 Boudreaux
2016/0166342 A1 6/2016 Prisco et al.
2016/0184034 A1 6/2016 Holop et al.
2016/0287279 A1 10/2016 Bovay et al.
2016/0296219 A1 10/2016 Srivastava et al.
2016/0303743 A1 10/2016 Rockrohr
2016/0338762 A1 11/2016 Krastins et al.
2016/0361049 A1 12/2016 Dachs, II et al.
2016/0361107 A1 12/2016 Zergiebel et al.
2017/0007345 A1 1/2017 Smith et al.
2017/0014998 A1 1/2017 Langenfeld et al.
2017/0165017 A1 6/2017 Chaplin et al.
2017/0172672 A1 6/2017 Bailey et al.
2017/0207467 A1 7/2017 Shelton, IV et al.
2017/0248194 A1 8/2017 Bae et al.
2017/0252096 A1 9/2017 Felder et al.
2017/0265865 A1 9/2017 Burbank
2018/0080533 A1 3/2018 Awtar
2018/0104011 A1 4/2018 Kadokura et al.
2018/0104012 A1* 4/2018 Wixey ............. A61B 17/00234
2018/0126504 A1 5/2018 Shelton, IV et al.
2018/0206904 A1 7/2018 Felder et al.
2018/0214223 A1 8/2018 Turner
2018/0229021 A1 8/2018 Donlon et al.
2018/0311001 A1 11/2018 Prisco et al.
2019/0029767 A1 1/2019 Hasegawa et al.
2019/0038282 A1 2/2019 Shelton, IV et al.
2019/0099227 A1 4/2019 Rockrohr
2019/0117325 A1 4/2019 Kishi
2019/0125468 A1 5/2019 Adams
2019/0159846 A1 5/2019 Yates et al.
2019/0192137 A1 6/2019 Shelton, IV et al.
2019/0223960 A1 7/2019 Chaplin et al.
2019/0231451 A1 8/2019 Lambrecht et al.
2019/0231464 A1 8/2019 Wixey et al.
2019/0239965 A1 8/2019 Abbott
2019/0249759 A1 8/2019 Abbott
2019/0298323 A1 10/2019 Lambrecht et al.
2019/0328467 A1 10/2019 Waterbury et al.
2019/0374297 A1 12/2019 Wallace et al.
2020/0008828 A1 1/2020 Overmyer
2020/0015807 A1 1/2020 Limon et al.
2020/0054405 A1 2/2020 Schuh et al.
2020/0054408 A1 2/2020 Schuh et al.
2020/0093554 A1 3/2020 Schuh et al.
2020/0129226 A1 4/2020 Burbank et al.
2020/0138473 A1 5/2020 Shelton, IV et al.
2020/0138531 A1 5/2020 Chaplin
2020/0155136 A1 5/2020 Shuh et al.
2020/0155253 A1 5/2020 Shuh et al.
2020/0261168 A1 8/2020 Anglese
2020/0383738 A1 12/2020 Abbott et al.
2020/0383739 A1 12/2020 Abbott et al.
2021/0022819 A1 1/2021 Duque et al.
2021/0045819 A1 2/2021 Castillo et al.
2021/0093408 A1 4/2021 Carey et al.
2021/0169597 A1 6/2021 Abbott et al.
2021/0220001 A1 7/2021 Heiliger
2021/0401523 A1 12/2021 Suresh
2021/0401524 A1 12/2021 Suresh et al.
2022/0000572 A1 1/2022 Ragosta et al.
2022/0015847 A1 1/2022 Kadokura
2022/0039895 A1 2/2022 Adams et al.
2022/0096067 A1 3/2022 Beckman et al.
2022/0096082 A1 3/2022 Beckman et al.
2022/0128133 A1 4/2022 Cooper et al.
2022/0192764 A1 6/2022 Waterbury et al.
2022/0249184 A1 8/2022 Fischer et al.
2022/0280253 A1 9/2022 He et al.
2023/0045998 A1 2/2023 Shelton, IV et al.
2023/0119001 A1 4/2023 Abbott
2023/0119775 A1 4/2023 Lambrecht et al.
2023/0172680 A1 6/2023 Reid et al.
2023/0279931 A1 9/2023 Cooper et al.
2023/0329807 A1 10/2023 Heye
2023/0355328 A1 11/2023 Lambrecht et al.
2024/0090972 A1 3/2024 Lambrecht et al.
2024/0100942 A1 3/2024 Mattsson et al.
2024/0156551 A1 5/2024 Lambrecht et al.
2024/0197423 A1 6/2024 Ragosta et al.
2024/0315792 A1 9/2024 Lambrecht et al.
2024/0366329 A1 11/2024 Kadokura
2024/0382279 A1 11/2024 Baldwin et al.
2025/0000598 A1 1/2025 Baldwin et al.

(56) References Cited

U.S. PATENT DOCUMENTS

| | | | |
|---|---|---|---|
| 2025/0169899 | A1 | 5/2025 | Heye |
| 2025/0186147 | A1 | 6/2025 | Times et al. |

FOREIGN PATENT DOCUMENTS

| | | | |
|---|---|---|---|
| CN | 101893060 | A | 11/2010 |
| CN | 103251458 | A | 8/2013 |
| CN | 104116547 | A | 10/2014 |
| CN | 104799891 | A | 7/2015 |
| CN | 105212987 | A | 1/2016 |
| CN | 108430374 | A | 8/2018 |
| CN | 109069138 | A | 12/2018 |
| CN | 109505951 | A | 3/2019 |
| CN | 110269686 | A | 9/2019 |
| CN | 110584787 | A | 12/2019 |
| DE | 102016112546 | A1 | 3/2017 |
| EP | 2362285 | A2 | 8/2011 |
| EP | 2548529 | A1 | 1/2013 |
| EP | 2783643 | A1 | 10/2014 |
| EP | 3103374 | A1 | 12/2016 |
| EP | 3195993 | A1 | 7/2017 |
| EP | 3476321 | A1 | 5/2019 |
| EP | 3508311 | A1 | 7/2019 |
| FR | 3014678 | A1 | 6/2015 |
| JP | H06114000 | A | 4/1994 |
| JP | H10249777 | A | 9/1998 |
| JP | 2003024336 | A | 1/2003 |
| JP | 2004301275 | A | 10/2004 |
| JP | 2005288590 | A | 10/2005 |
| WO | WO-8910242 | A1 | 11/1989 |
| WO | WO-9729690 | A1 | 8/1997 |
| WO | WO-2010009224 | A1 | 1/2010 |
| WO | WO-2010039387 | A1 | 4/2010 |
| WO | WO-2011060046 | A2 | 5/2011 |
| WO | WO-2014025204 | A1 | 2/2014 |
| WO | WO2014/070980 | A1 | 5/2014 |
| WO | WO-2014151952 | A1 | 9/2014 |
| WO | WO-2015142290 | A1 | 9/2015 |
| WO | WO-2016025132 | A1 | 2/2016 |
| WO | WO-2016172299 | A1 | 10/2016 |
| WO | WO-2016189284 | A1 | 12/2016 |
| WO | WO-2017064303 | A1 | 4/2017 |
| WO | WO-2017188851 | A1 | 11/2017 |
| WO | WO-2017189272 | A1 | 11/2017 |
| WO | WO-2018049211 | A1 | 3/2018 |
| WO | WO-2018049217 | A1 | 3/2018 |
| WO | WO-2018069679 | A1 | 4/2018 |
| WO | WO-2018179140 | A1 | 10/2018 |
| WO | WO-2019222058 | A1 | 11/2019 |
| WO | WO-2020102776 | A1 | 5/2020 |
| WO | WO-2020102780 | A1 | 5/2020 |
| WO | WO-2020184588 | A1 | 9/2020 |
| WO | WO-2020252184 | A1 | 12/2020 |
| WO | WO-2021041395 | A1 | 3/2021 |
| WO | WO-2021155707 | A1 | 8/2021 |
| WO | WO-2021192255 | A1 | 9/2021 |
| WO | WO-2023055684 | A2 | 4/2023 |
| WO | WO-2023177554 | A1 | 9/2023 |

OTHER PUBLICATIONS

Invitation to pay additional fee received from the International Search Authority for Application No. PCT/US2021/017840, mailed Jun. 2, 2021, 13 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for CN Application No. 2021800245844, mailed Jun. 12, 2025, pp. 13.

Office Action for EP Application No. 21714996.2, mailed Sep. 4, 2025, pp. 5.

Office Action for CN Application No. 202180024584.4, mailed Oct. 14, 2025, pp. 20.

* cited by examiner

DEVICES AND METHODS FOR COUPLING A CABLE TO A MEDICAL DEVICE

CROSS-REFERENCE TO RELATED APPLICATIONS

This application is a U.S. national stage filing under 35 U.S.C. § 371 of International Application No. PCT/US2021/017840 (filed Feb. 12, 2021), entitled "Devices and Methods for Coupling a Cable to a Medical Device," which claims priority to and the benefit of U.S. Provisional Patent Application No. 62/975,927, entitled "Devices and Methods for Coupling a Cable to a Capstan of a Medical Device," filed Feb. 13, 2020 and U.S. Provisional Patent Application No. 62/975,928, entitled "Devices and Methods for Coupling a Cable to a Capstan of a Medical Device," filed Feb. 13, 2020, each of the disclosures of which is incorporated herein by reference in its entirety.

BACKGROUND

The embodiments described herein relate to medical devices, and more specifically to endoscopic tools. More particularly, the embodiments described herein relate to devices that include tension cables and mechanisms for coupling the cables to any of a capstan or an end effector tool coupled thereto.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of a shaft. During an MIS procedure, the end effector, wrist mechanism, and the distal end of the shaft can be inserted into a small incision or a natural orifice of a patient to position the end effector at a work site within the patient's body. The optional wrist mechanism can be used to change the end effector's orientation with respect to the shaft to perform the desired procedure at the work site. Known wrist mechanisms generally provide the desired degrees of freedom (DOFs) for movement of the end effector. For example, known wrist mechanisms are often able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include cables (e.g., cables) that extend through the shaft of the instrument and that connect the wrist mechanism to a mechanical structure configured to move the cables to operate the wrist mechanism. For robotic or teleoperated systems, the mechanical structure is typically motor driven and can be operably coupled to a processing system to provide a user interface for a clinical user (e.g., a surgeon) to control the instrument.

Patients benefit from continual efforts to improve the effectiveness of MIS methods and tools. For example, reducing the size and/or the operating footprint of the shaft and wrist mechanism can allow for smaller entry incisions and reduced need for space at the surgical site, thereby reducing the negative effects of surgery, such as pain, scarring, and undesirable healing time. But producing small medical instruments that implement the clinically desired functions for minimally invasive procedures can be challenging. Specifically, simply reducing the size of known wrist mechanisms by "scaling down" the components will not result in an effective solution because required component and material properties do not scale. For example, efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys and/or contoured surfaces are generally needed to reduce cable friction, which extends instrument life and permits operation without excessive forces being applied to the cables or other structures in the wrist mechanism. Increased localized forces that may result from smaller structures (including the cables and other components of the wrist mechanism) can result in undesirable lengthening (e.g., "stretch" or "creep") of the cables during storage and use, reduced cable life, and the like.

Further, the wrist mechanism generally provides specific degrees of freedom for movement of the end effector. For example, for forceps or other grasping tools, the wrist may be able to change the pitch, yaw, and grip of the end effector. More degrees of freedom could be implemented through the wrist but would require additional actuation members in the wrist and shaft, which competes for the limited space that exists given the size restrictions required by MIS applications. Other degrees of freedom, such as roll or insertion/extraction through movement of the main tube also competes for space at or in the shaft of the device.

A conventional architecture for a wrist mechanism in a robotically controlled medical instrument uses cables to turn a capstan in the backend mechanism and thereby rotate the portion of the wrist mechanism that is connected to the capstan. For example, a wrist mechanism can be operably coupled to three capstans for rotations about a pitch axis, a yaw axis, or a grip axis. Each capstan can be controlled using two cables that are attached to the capstan so that one side pays out cable while the other side pulls in an equal length of cable. With this architecture, three degrees of freedom call for a total of six cables extending from the wrist mechanism back along the length of the main tube to the backend mechanism of the instrument. Efficient implementation of a wrist mechanism and backend mechanism can be complicated because the cables must be carefully routed through the wrist mechanism, tool member and backend mechanism to maintain stability of the wrist throughout the range of motion of the wrist mechanism and to minimize the interactions (or coupling effects) of one rotation axis upon another.

Some known architectures for a robotically controlled medical instrument use cables including crimps or other retention methods to secure the cables to the capstan or to the tool member, which can increase the time and costs of manufacturing the medical instrument. For example, there may be increased time needed for routing and securing the crimps to the capstan and/or end effector. In addition, the cables themselves can be very expensive. For example, many conventional architectures for robotically controlled medical instrument use cables made from materials such as, for example, tungsten or steel. Such cables can be constructed for multiple use but are also very expensive.

Thus, a need exists for improved endoscopic tools, including improved backend mechanisms to enable a wrist to be operated with a small number of cables, to facilitate miniaturization of the instrument, reduce costs of the instrument, and to reduce manufacturing cost by reducing the number of parts required. A need also exists for improved endoscopic tools that can provide tighter control of the movement of the wrist mechanism and end effector, and that can include cables formed with materials, such as, various polymers that can decrease costs. A further need exists for endoscopic tools that include an architecture that does not require the cables to include a crimp or otherwise need a retention element to secure the cable within the wrist mechanism, end effector or backend mechanism.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, a medical device includes a shaft including a distal end portion and a proximal end portion, a tool member, a mechanical structure, and a cable. The tool member is rotatably coupled to the distal end portion of the shaft about a rotation axis and includes a drive pulley and a coupling spool. The mechanical structure is coupled to the proximal end portion of the shaft and includes a first capstan and a second capstan. The first capstan includes a first portion and a second portion. The second capstan includes a first portion and a second portion. The cable includes a first proximal end, a second proximal end, and a distal portion and is routed along the shaft. The distal portion of the cable is routed about a drive surface of the drive pulley and is wrapped at least one revolution about the coupling spool to secure the distal portion of the cable to the tool member. The first proximal end of the cable is routed about a drive surface of the first portion of the first capstan and is wrapped about the second portion of the first capstan such that a second wrap portion of the first proximal end of the cable crosses over a first wrap portion of the first proximal end of the cable. The second proximal end of the cable is routed about a drive surface of the first portion of the second capstan and is wrapped about the second portion of the second capstan such that a second wrap portion of the second proximal end of the cable crosses over a first wrap portion of the second proximal end of the cable.

In some embodiments, the cable of the medical device is formed with a polymer. In some embodiments, the cable of the medical device is devoid of a retention feature. In some embodiments, the distal end cable is wrapped at least two revolutions about the coupling spool. In some embodiments, the first proximal end of the cable is wrapped at least two revolutions about the second portion of the first capstan and the second proximal end of the cable is wrapped at least two revolutions about the second portion of the second capstan. In some embodiments, a first slot and a second slot are defined within the second portion of the first capstan, and the second slot crosses the first slot. In such an embodiment, the first proximal end of the cable is wrapped about the second portion of the first capstan within the first slot and the first proximal end of the cable is wrapped about the second portion of the first capstan within the second slot such that the second wrap portion of the cable crosses over the first wrap portion of the cable.

In some embodiments, a medical instrument includes a shaft that includes a distal end portion and a proximal end portion and a mechanical structure coupled to the proximal end portion of the shaft. The mechanical structure includes a capstan having a first portion and a second portion. The first portion includes a drive surface configured to engage a cable such that rotation of the capstan produces a tension force in the cable. A first slot and a second slot are defined within the second portion of the capstan. The second slot crosses the first slot and the first slot and the second slot are each configured to receive the cable to secure the cable to the second portion of the capstan. A termination opening is defined within the second portion.

In some embodiments, the medical instrument further includes the cable coupled to the capstan. The cable extends along the shaft and is routed about the drive surface of the first portion. The cable is wrapped about the second portion of the capstan within the first slot and wrapped about the second portion of the capstan within the second slot such that a second wrap portion of the cable crosses over a first wrap portion of the cable. A termination end of the cable is coupled within the termination opening.

In some embodiments, a medical instrument includes a shaft having a distal end portion and a proximal end portion. An end effector is coupled to the distal end portion of the shaft and a mechanical structure is coupled to the proximal end portion of the shaft. The mechanical structure includes a capstan that has a first portion and a second portion. The first portion includes a drive surface, and a termination opening is defined within the second portion. A first slot and a second slot are defined within the second portion and the second slot crosses the first slot. A cable is routed along the shaft and includes a proximal end and a distal end. The distal portion of the cable is coupled to the end effector and the proximal end of the cable includes a drive portion, a first wrap portion, a second wrap portion, and a termination portion. The drive portion of the cable is wrapped at least partially around the drive surface of the first portion of the capstan. The first wrap portion of the cable is wrapped about the second portion of the capstan within the first slot and the second wrap portion of the cable is wrapped about the second portion of the capstan within the second slot such that the second wrap portion crosses over the first wrap portion. The termination portion is coupled within the termination opening.

In some embodiments, the drive surface of the first portion of the capstan of the medical device is a circular groove about a longitudinal axis of the capstan and defines a diameter. The second portion of the capstan is cylindrical about the longitudinal axis of the capstan and defines a diameter that is greater than the diameter of the drive surface. In some embodiments, the first portion of the capstan includes a first side wall and a second side wall, and the drive surface of the capstan is between the first side wall and the second side wall. In some such embodiments, a passageway is defined within the first side wall and the first wrap portion of the cable is routed from the first portion of the capstan, through the passageway, and to the first slot. In some embodiments, the termination portion of the cable has a constant cross-sectional diameter. In some embodiments, a central bore is defined within the capstan and the capstan includes a reinforcing rod within the central bore.

In some embodiments, a method of assembling a medical instrument is provided where the medical instrument includes a shaft, an end effector movably coupled to a distal end of the shaft, a mechanical structure coupled to a proximal end of the shaft, and a cable. The cable includes a drive portion, a first wrap portion, a second wrap portion, and a termination portion. The method includes routing the cable from the end effector through the shaft and to a capstan of the mechanical structure. The capstan includes a first portion and a second portion. The first portion includes a drive surface, and each of a first slot, a second slot, and a termination opening are defined within the second portion. The method further includes wrapping at least a portion of the drive portion of the cable about the drive surface of the first portion of the capstan. The first wrap portion is wrapped about the second portion of the capstan within the first slot and the second wrap portion is wrapped about the second portion of the capstan within the second slot such that the second wrap portion crosses over the first wrap portion. The termination portion is secured within the termination opening.

In some embodiments, the cable includes a polymer. In some embodiments, the termination portion of the cable is devoid of a retention feature. In some embodiments, the method further includes after the wrapping the second wrap portion, cutting an end of the cable to form a termination portion of the cable.

In some embodiments, a medical instrument includes a shaft having a distal end portion and a proximal end portion, a link, a tool member, and a cable. The link is coupled to the distal end portion of the shaft and the tool member is rotatably coupled to the link about a rotation axis. The tool member includes a drive pulley and a coupling spool. The drive pulley includes a drive surface at a first location along the rotation axis. The coupling spool includes a wrap surface at a second location along the rotation axis and the second location is offset from the first location. The cable includes a proximal end and a distal end. The proximal end of the cable is routed along the shaft and the distal end of the cable includes a first pulley portion, a wrap portion, and a second pulley portion. The first pulley portion of the cable is wrapped at least partially around a first portion of the drive surface of the drive pulley. The wrap portion of the cable is wrapped about the wrap surface of the coupling spool. The second pulley portion of the cable is wrapped at least partially around a second portion of the drive surface of the drive pulley.

In some embodiments, the wrap portion of the cable includes a first segment and a second segment and the wrap portion of the cable is wrapped about the coupling spool such that the second segment crosses over the first segment. In some embodiments, the wrap portion of the cable is wrapped at least two revolutions about the coupling spool. In some embodiments, a circular groove is defined within the coupling spool, and the wrap surface is within the circular groove. In some embodiments, the cable includes a polymer. In some embodiments, the wrap portion of the cable is devoid of a retention feature.

In some embodiments, a medical instrument includes a link configured to be coupled to a distal end portion of a shaft and a tool member that is rotatably coupled to the link about a rotation axis. The tool member includes a drive pulley and a coupling spool. The drive pulley includes a drive surface configured to engage a cable such that a tension force exerted by the cable along the drive surface produces a rotation torque about the rotation axis. The drive surface is at a first location along the rotation axis. The coupling spool includes a wrap surface to which the cable is configured to be secured to the tool member. The wrap surface is at a second location along the rotation axis. The second location is offset from the first location along the rotation axis.

In some embodiments, the medical instrument further includes the cable coupled to the tool member. The cable extends along the shaft and is routed about a first portion of the drive surface of the drive pulley. The cable is further wrapped at least one revolution about the wrap surface of the coupling spool and routed about a second portion of the drive surface of the drive pulley. In some embodiments, the cable is wrapped at least two revolutions about the wrap surface of the coupling spool. In some embodiments, the cable is wrapped about the wrap surface of the coupling spool such that a second segment of the cable crosses over a first segment of the cable.

In some embodiments of the medical instrument the drive pulley includes a jaw connection protrusion and the tool member includes a jaw that is constructed separately from the drive pulley. A connection opening is defined by the jaw; and the jaw connection protrusion of the drive pulley is coupled within the connection opening of the jaw. In some embodiments, the tool member is a first tool member, the medical instrument includes a second tool member rotatably coupled to the link about the rotation axis, and the drive pulley includes a rotation limit protrusion configured to engage a shoulder of the second tool member to limit rotation of the first tool member relative to the second tool member about the rotation axis.

In some embodiments, a medical instrument includes a shaft, a link a tool member and a cable. The shaft includes a distal end portion and a proximal end portion. The link is coupled to the distal end portion of the shaft and a tool member is rotatably coupled to the link about a rotation axis. The tool member includes a drive pulley and a coupling spool. The cable includes a proximal end and a distal end. The proximal end of the cable is routed along the shaft, and the distal end of the cable includes a first pulley portion, a wrap portion, and a second pulley portion. The first pulley portion of the cable is wrapped at least partially around a first portion of the drive pulley. The wrap portion of the cable is wrapped about the wrap surface of the coupling spool such that a first segment of the wrap portion of the cable crosses over a second segment of the wrap portion of the cable. The second pulley portion of the cable is wrapped at least partially around a second portion of the drive surface of the drive pulley of the tool member.

In some embodiments, the tool member includes a protrusion about which at least one of the first pulley portion, the wrap portion, or the second pulley portion is partially wrapped. In some embodiments, the tool member includes a side wall, a first protrusion, and a second protrusion and the side wall separates the drive pulley and the coupling spool. An opening is defined by the side wall between the first protrusion and the second protrusion, and the wrap portion of the cable is routed from the drive pulley to the coupling spool via the opening. The first pulley portion of the cable is partially wrapped about the first protrusion and the second pulley portion of the cable is partially wrapped about the second protrusion.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

DETAILED DESCRIPTION

Figure 1:
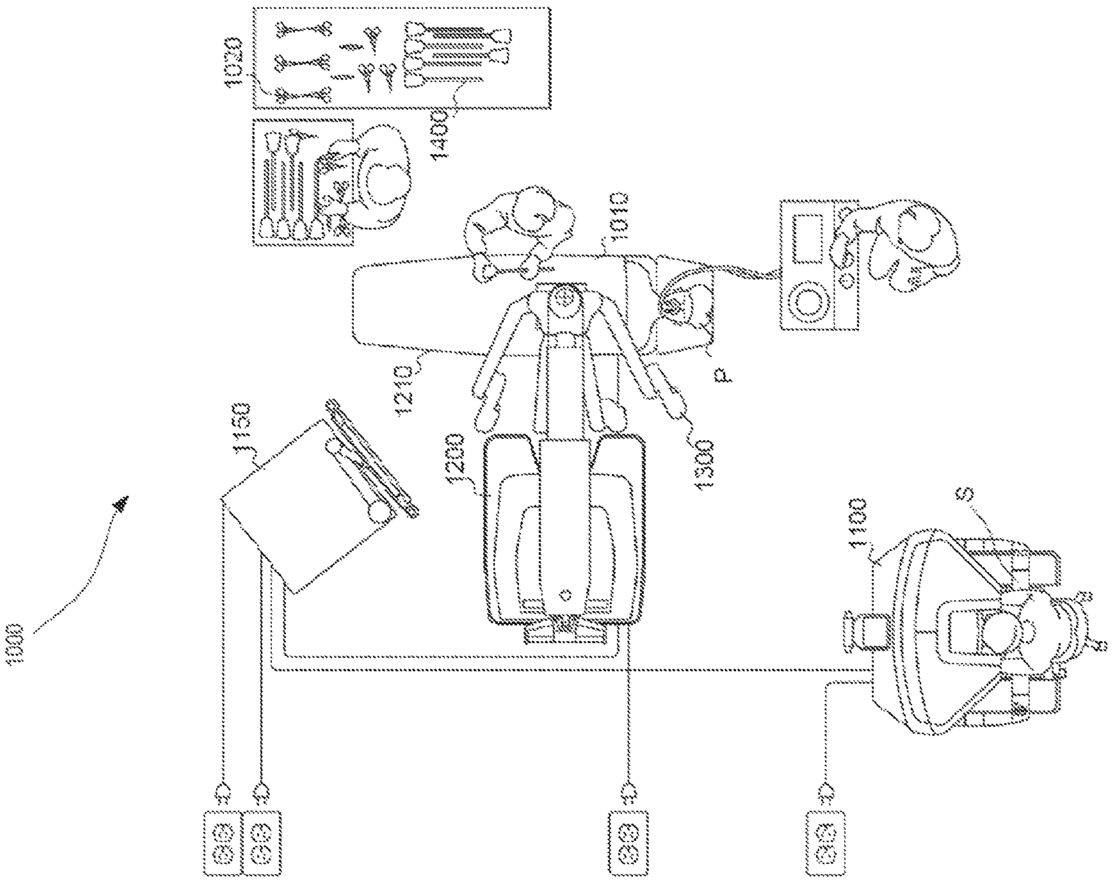
FIG. 1 is a plan view of a minimally invasive teleoperated medical system according to an embodiment being used to perform a medical procedure such as surgery.

The embodiments described herein can advantageously be used in a wide variety of grasping, cutting, and manipulating operations associated with minimally invasive surgery.

The medical instruments of the present application enable motion in three degrees of freedom (e.g., about a pitch axis, a yaw axis, and a grip axis) using only four cables, thereby reducing the total number of cables required, reducing the space required within the shaft and wrist, reducing overall cost, and enables further miniaturization of the wrist and shaft assemblies to promote MIS procedures. Moreover, the instruments described herein include one or more cables (which function as tension members) that are formed with a polymer material and that can be secured to a capstan of the backend mechanism without the need for a retention element or other securing feature. The capstans can be configured with grooves and a cable can be wrapped about a capstan and disposed at least partially within the grooves such that a first wrap portion of the cable crosses over a second wrap portion of the cable. The cross-over configuration assists in securing the cables to the capstans. The polymer material of the cable or a coating applied to the surface thereof also provides sufficient friction to further assist in maintaining the cable secured to the capstan without the need for any additional mechanisms for securing the cable to the capstan (e.g., placing cable crimps within a guide slot, securing the cable to the capstan with an adhesive, or the like).

Additionally, the instruments described herein can include a tool member (e.g., a grasper, blade, etc.) that include jaws having a coupling spool and a drive pulley that are offset from one another along a rotation axis of the tool member. Cables as described herein can be wrapped about the drive pulley and the coupling spool and held thereto by friction properties of the cable and by crossing a first portion of the cable over a second portion of the cable as described in more detail below.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000), da Vinci X® Surgical System (Model IS4200), and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, handoperated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instruments 1400 (also referred to herein as a "tool") through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
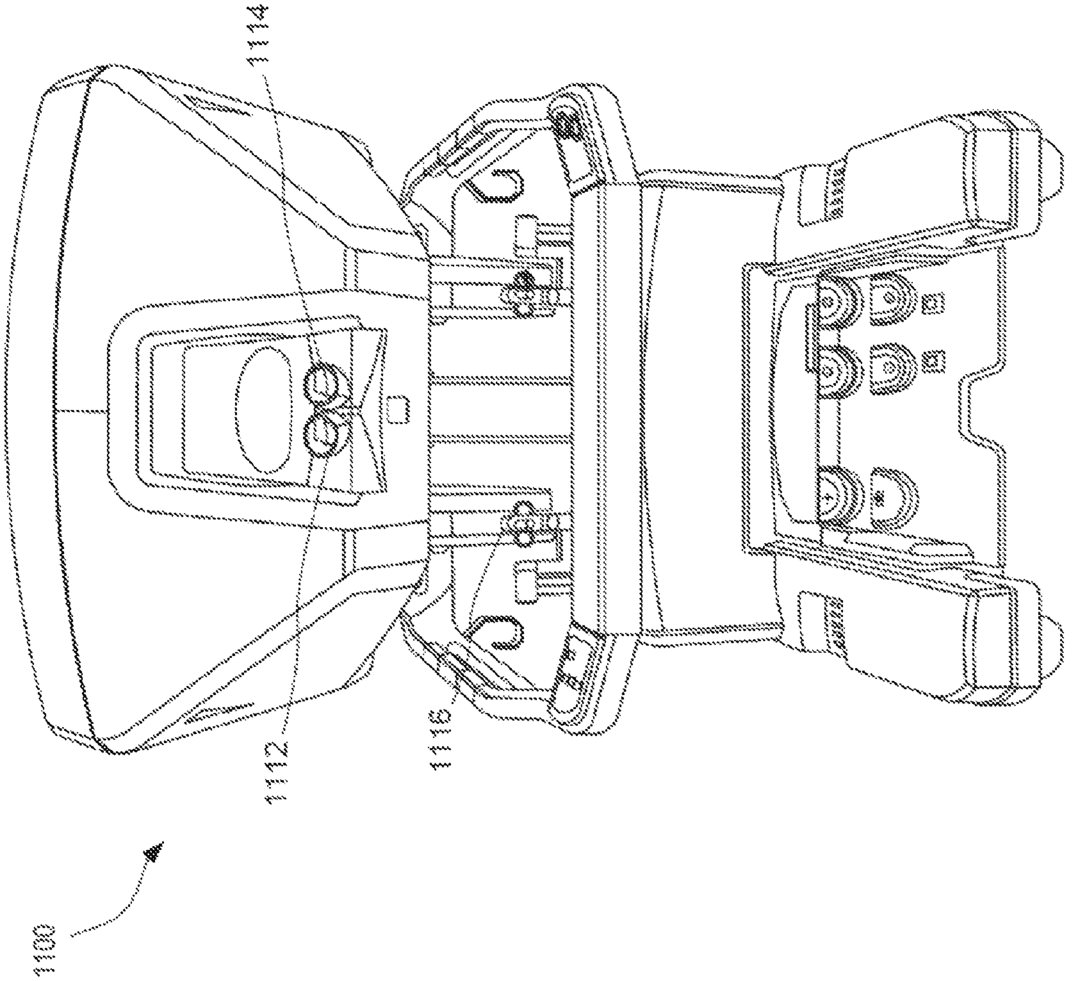
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
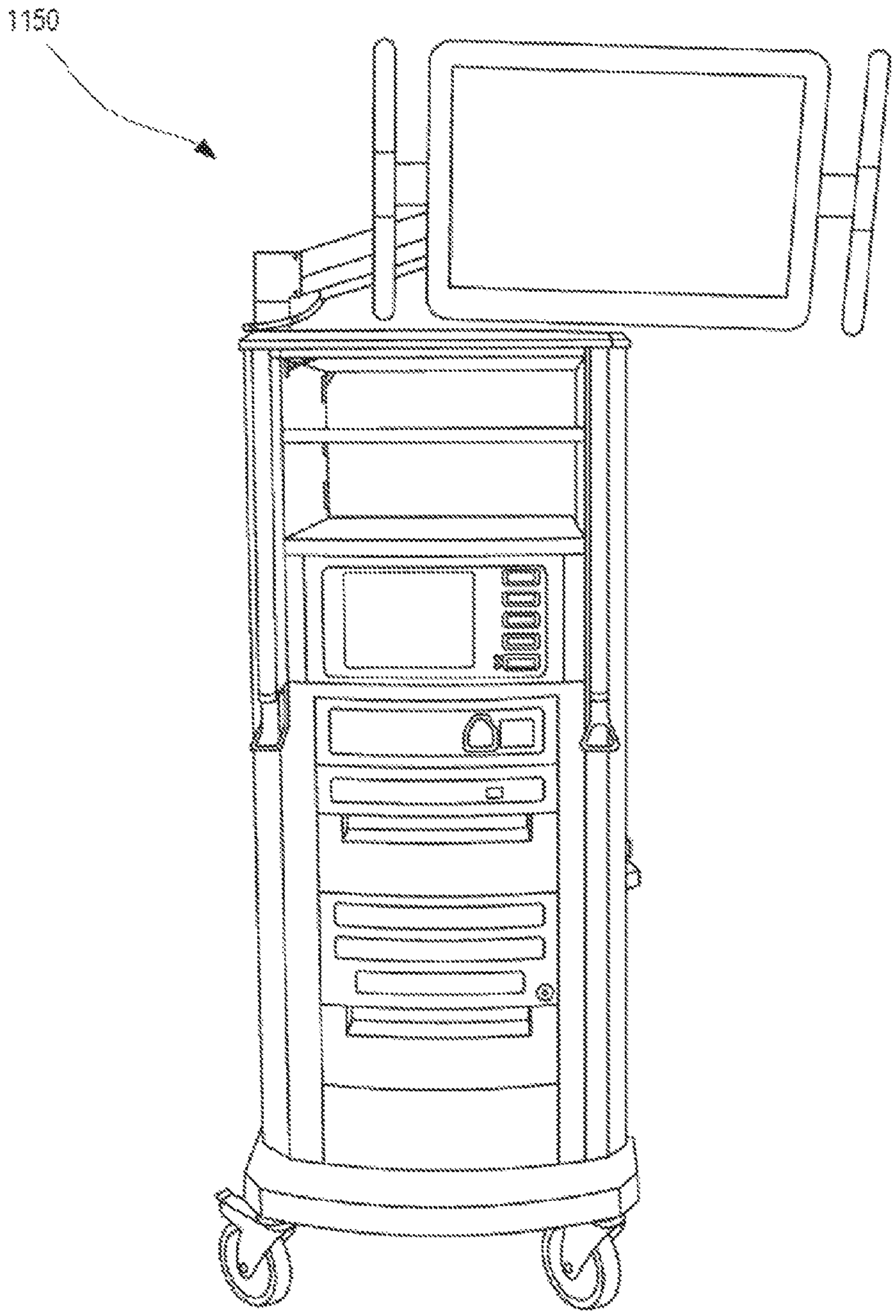
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
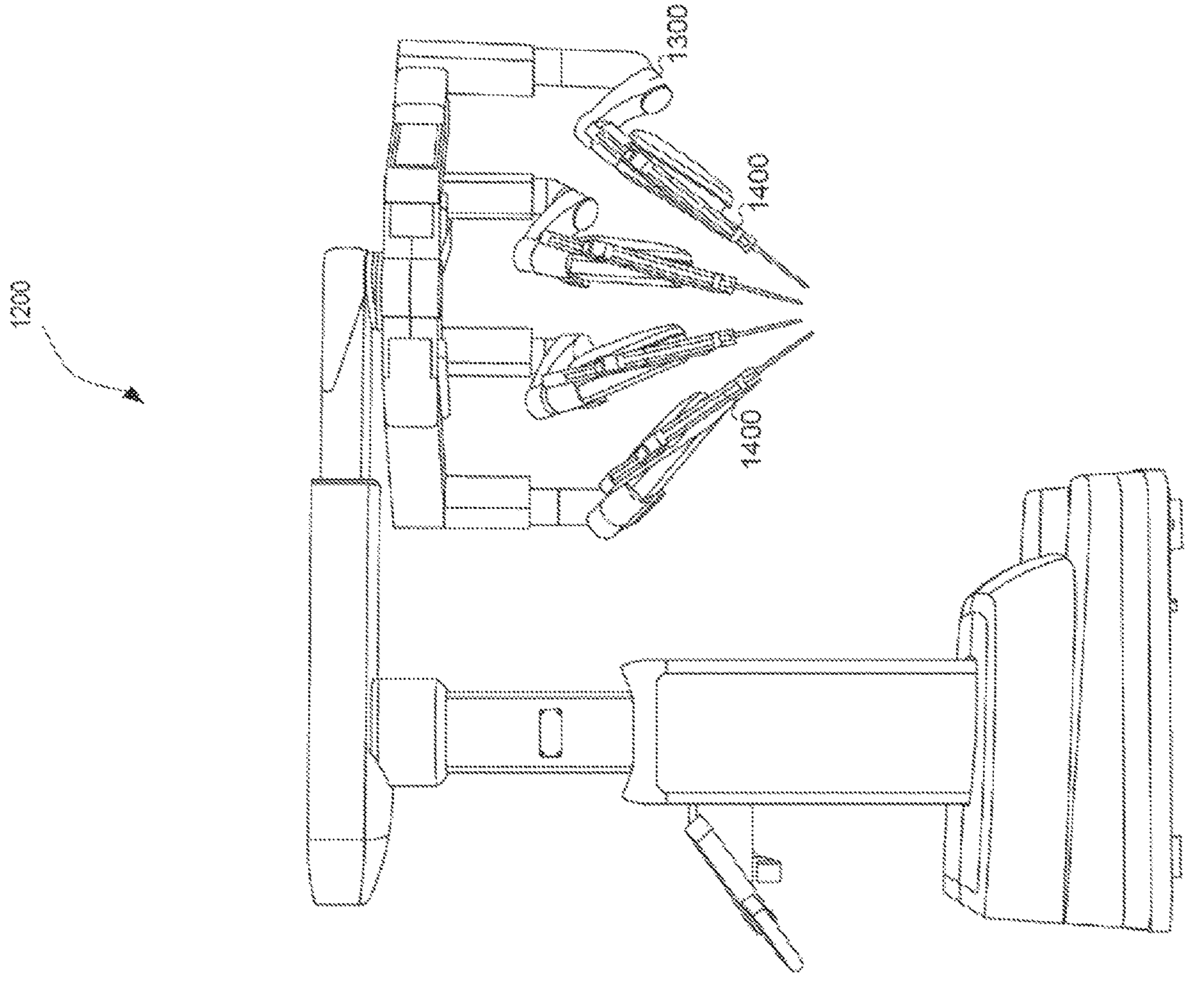
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a software and/or kinematic remote center of motion is maintained at the incision or orifice. In this manner, the incision size can be minimized.

FIGS. 5-7*b* are schematic illustrations of a portion of a medical instrument 2400 according to an embodiment. The instrument 2400 includes a shaft 2410, a cable 2420 (which acts as a first tension member), an end effector 2460, and a mechanical structure 2700. The mechanical structure 2700 can be configured to function as an "actuator" or a "transmission or a "transmission assembly" to move one or more components of the medical instrument 2400 and/or to interface with other portions of the surgical system, such as, for example, the manipulator unit 1200 described above. In some embodiments, the mechanical structure 2700 (and any of the mechanical structures described herein) can include one or more drive motors to produce the force or torque to move the components of the medical instrument 2400. In other embodiments, mechanical structure 2700 (and any of the mechanical structures described herein) is devoid of any motors therein. For example, in some embodiments, the mechanical structure 2700 (and any of the mechanical structures described herein) is coupled to a manipulator unit that includes one or more motors. The cable 2420 includes a first proximal portion 2421, a second proximal portion 2423 and a distal portion 2422. The first proximal end portion 2421 and the second proximal end portion 2423 are each coupled to the mechanical structure 2700, and the distal portion 2422 is coupled to the end effector 2460 as described in more detail below. The shaft 2410 includes a proximal end portion 2411 and a distal end portion 2412 and defines a lumen 2413.

The end effector 2460 is rotatably coupled to the distal end portion 2412 of the shaft 2410 and includes at least one tool member 2462. The instrument 2400 is configured such that movement of the first proximal portion 2421 and the second proximal portion 2423 of the cable 2420 produces movement of the tool member 2462 about a first axis of rotation $A_1$ (which functions as the yaw axis, the term yaw is arbitrary), in a direction of arrows AA. In some embodiments, the medical instrument 2400 can include a wrist assembly including one or more links (not shown in FIGS. 5-7*b*) that couples the end effector 2460 to the distal end portion 2412 of the shaft 2410. In such an embodiment, movement of the first proximal portion 2421 and the second proximal portion 2423 of the cable 2420 can also produce movement of the wrist assembly about a second axis of rotation (not shown in FIGS. 5-7*b*, but which functions as the pitch axis, the term pitch is arbitrary) or both movement of the wrist assembly and the end effector 2460. An embodiment with a wrist assembly is described herein with reference to FIGS. 21-36.

The tool member 2462 includes a contact portion 2464, a drive pulley 2470 and a coupling spool 2467. The contact portion 2464 is configured to engage or manipulate a target tissue during a surgical procedure. For example, in some embodiments, the contact portion 2464 can include an engagement surface that functions as a gripper, cutter, tissue manipulator, or the like. In other embodiments, the contact portion 2464 can be an energized tool member that is used for cauterization or electrosurgical procedures. The end effector 2462 is operatively coupled to the mechanical structure 2700 such that the tool member 2462 rotates relative to shaft 2410 about the first axis of rotation $A_1$ in the direction of the arrow AA. In this manner, the contact portion 2464 of the tool member 2462 can be actuated to engage or manipulate a target tissue during a surgical procedure. The tool member 2462 (or any of the tool members described herein) can be any suitable medical tool member. Moreover, although only one tool member 2462 is shown, in other embodiments, the instrument 2400 can include two or more moving tool members that cooperatively perform gripping or shearing functions.

The mechanical structure 2700 includes a housing 2760, a first capstan 2710, and a second capstan 2720. The housing 2760 (which functions as a chassis) provides the structural support for mounting and aligning the components of the mechanical structure 2700. For example, the housing 2760 can define openings, protrusions and/or brackets for mounting of shafts or other components. The first capstan 2710 is mounted to the mechanical structure 2700 (e.g., within the housing 2760) via a first capstan support member (not shown). For example, the first capstan support member can be a mount, shaft, or any other suitable support structure to secure the first capstan 2710 to the mechanical structure 2700.

Figure 7A:
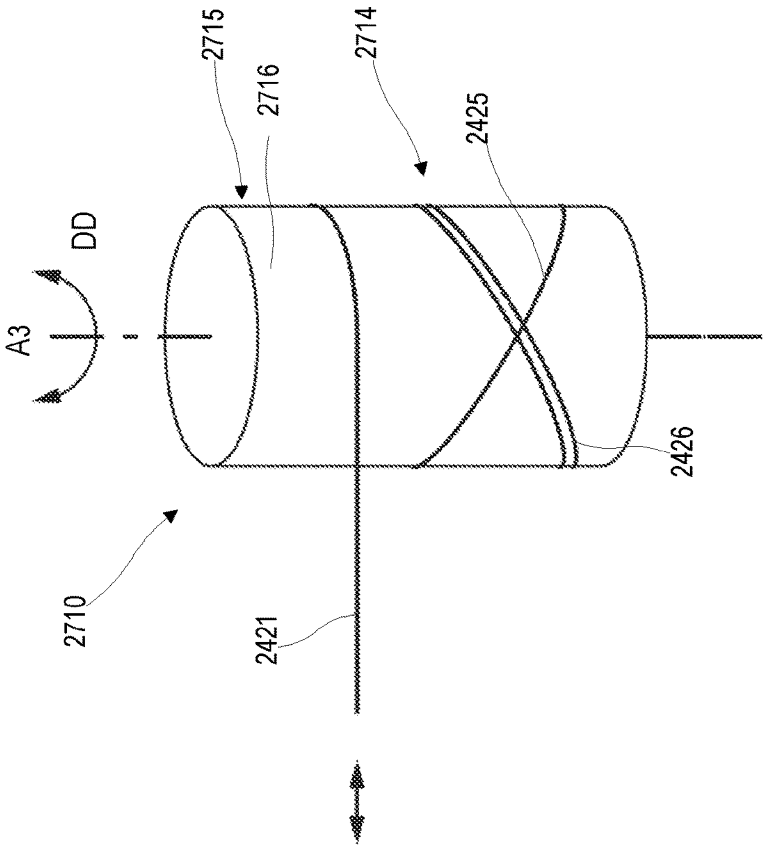
FIG. 7A is an enlarged perspective view of a capstan of the medical instrument of FIG. 5.

The second capstan 2720 is mounted to the mechanical structure 2700 (e.g., within the housing 2760) via a second capstan support member (not shown). For example, the second capstan support member can be a mount, shaft, or any other suitable support structure to secure the second capstan 2720 to the mechanical structure 2700. The first capstan 2710 and the second capstan 2720 can each be operable to be rotated about an axis A3 in a direction DD, as shown in FIG. 7A for first capstan 2710.

The cable 2420 is routed between the mechanical structure 2700 and the end effector 2460 and is coupled to the first capstan 2710 and the second capstan 2720 of the mechanical structure 2700. More specifically, the first proximal end portion 2421 of the cable 2420 is coupled to the first capstan 2710 of the mechanical structure 2700, the cable 2420 extends from the first capstan 2710 along the shaft 2410, and the distal portion 2422 of the cable 2410 is coupled to the end effector 2460, as described in more detail herein. Although the cable 2420 is shown extending within an interior lumen of the shaft 2410 in FIG. 5, in other embodiments, the cable 2420 can be routed exterior to the shaft 2410. The cable 2420 extends from the end effector 2460 along the shaft 2410 and the second proximal end portion 2423 is coupled to the second capstan 2720 of the mechanical structure 2700. In other words, the two ends of a single cable (e.g., 2420) are coupled to and actuated by two separate capstans of the mechanical structure 2700.

More specifically, the two ends of the cable 2420 that are associated with opposing directions of a single degree of freedom are connected to two independent drive capstans 2710 and 2720. This arrangement, which is generally referred to as an antagonist drive system, allows for independent control of the movement of (e.g., pulling in or paying out) each of the ends of the cable. The mechanical structure 2700 produces movement of the cable 2420, which operates to produce the desired articulation movements (pitch, yaw, or grip) at the end effector 2460. Accordingly, as described herein, the mechanical structure 2700 includes components and controls to move a first portion of the cable 2420 via the first capstan 2710 in a first direction (e.g., a proximal direction) and to move a second portion of the cable 2420 via the second capstan 2720 in a second opposite direction (e.g., a distal direction). The mechanical structure 2700 can also move both the first portion of the cable 2420 and the second portion of the cable 2420 in the same direction. In this manner, the mechanical structure 2700 can maintain the desired tension within the cables to produce the desired movements at the end effector 2460.

In other embodiments, however, any of the medical instruments described herein can have the two ends of the cable wrapped about a single capstan. This alternative arrangement, which is generally referred to as a self-antagonist drive system, operates the two ends of the cable using a single drive motor. In addition, in some alternative embodiments, the cable 2420 includes two cable segments, with each cable segment having a distal end portion that is coupled to the end effector 2460 and a proximal end portion wrapped about a capstan.

As described above, the cable 2420 is coupled to each of the first capstan 2710 and the second capstan 2720 and also to the end effector 2460. More specifically, the first proximal end portion 2421 and the second proximal end portion 2423 are each coupled to the respective first capstan 2710 and second capstan 2720 along a specific wrap path. The wrap path for the first proximal end portion 2421 of the cable 2420 on the first capstan 2710 is described herein, and it should be understood that the second proximal end portion 2423 can be coupled to the second capstan 2720 in the same manner. Further, specific details described below for the first capstan 2710 can also apply to the second capstan 2720.

Figure 7B:
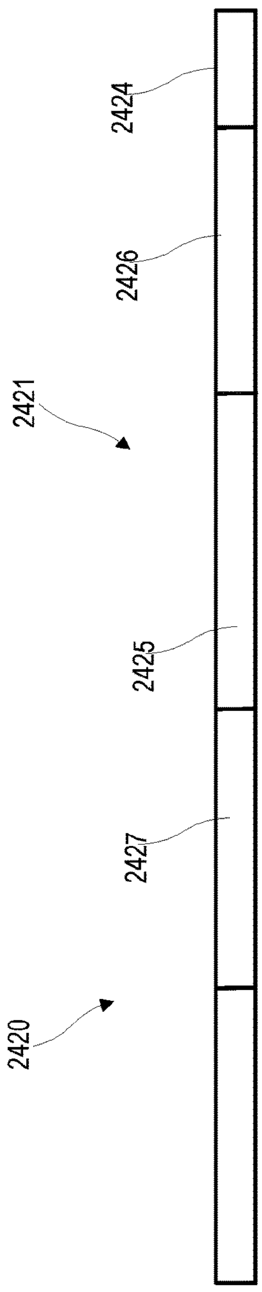
FIG. 7B is a side view of a portion of the cable of the medical instrument of FIG. 5.

As shown in FIG. 7A, the first capstan 2710 includes a first portion 2715 having a drive surface 2713, and a second portion 2714. The first portion 2715 functions as a spool portion and the second portion functions as an anchor portion to secure the cable 2420 to the capstan 2710). As shown in FIG. 7B, the first proximal end portion 2421 of the cable 2420 includes a drive portion 2427, a first wrap portion 2425, a second wrap portion 2426 and a termination portion 2424. The first proximal end portion 2421 is coupled to the first capstan 2710 such that a portion of the first proximal end portion 2421 wraps about the drive surface 2716 of the first portion 2715 of the first capstan 2710. The first proximal end portion 2421 is then wrapped about the second portion 2714 such that a portion of the first wrap portion 2425 of the cable 2420 crosses over a portion of the second wrap portion 2426 of the cable 2420. In some embodiments, at least one of the first wrap portion 2425 and the second wrap portion 2426 are wrapped about the first capstan 2710 at least two times (as shown in FIG. 7A), or in other words, makes at least two revolutions about the capstan 2710. In some embodiments, the first wrap portion 2524 and the second wrap portion 2426 need not be wrapped at least two times around the capstan 2710. As shown in FIG. 7A the first wrap portion 2425 is wrapped one time around (or makes one revolution about) the first capstan 2710, and the second wrap portion 2426 is wrapped two times around (or makes two revolutions about) the first capstan 2710. In some embodiments, at least one of the first wrap portion 2425 or the second wrap portion 2426 are wrapped about the first capstan 2710 three-times (e.g., makes 3 revolutions about the capstan). In some embodiments, at least one of the first wrap portion 2425 or the second wrap portion 2426 are wrapped about the first capstan 2710 more than three times. The multiple wraps or revolutions of the cable 2420 about the first capstan 2710 assist in maintaining the cable 2420 secured to the capstan 2710 without the use of a retention element (e.g., a crimp in the cable, a clamp or fastener to couple the cable to the capstan, or the like). In some embodiments, the termination portion 2424 of the cable is coupled to an opening or groove defined in the first capstan 2710 to assist in securing the cable 2420 to the first capstan 2710. In some embodiments, the opening or groove includes a pinch point or portion with a smaller width or diameter than the cable 2420 such that the termination portion 2424 is wedged therein.

Figure 5:
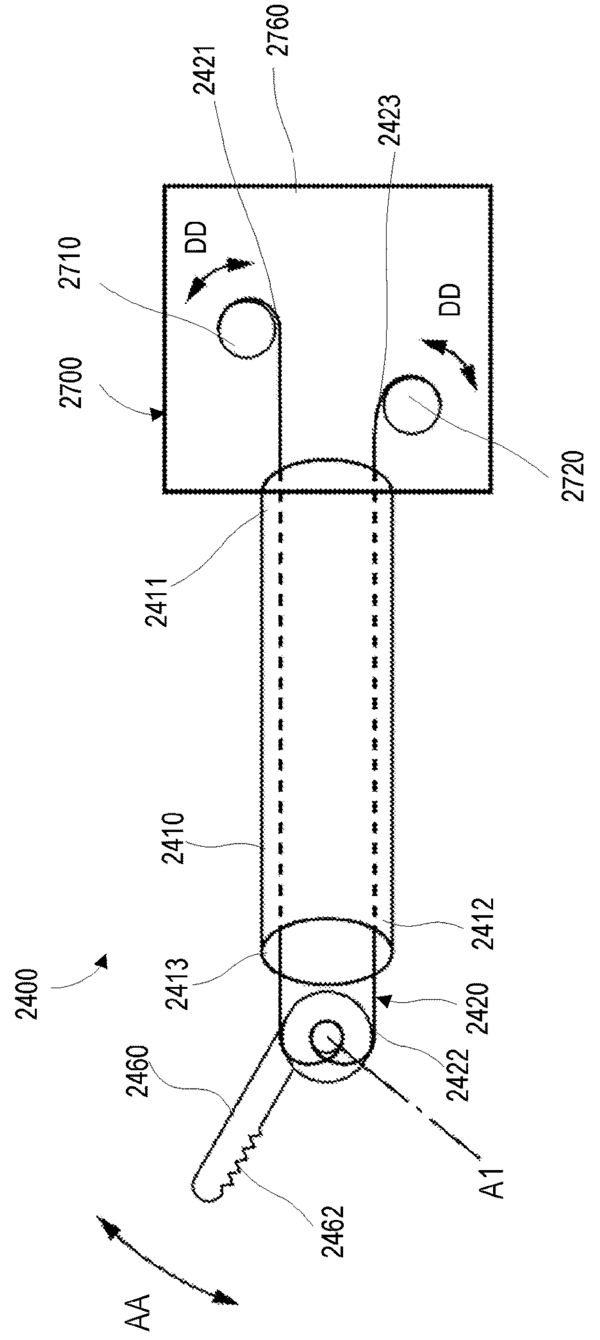
FIG. 5 is a diagrammatic illustration of a portion of a medical instrument according to an embodiment.
Figure 6:
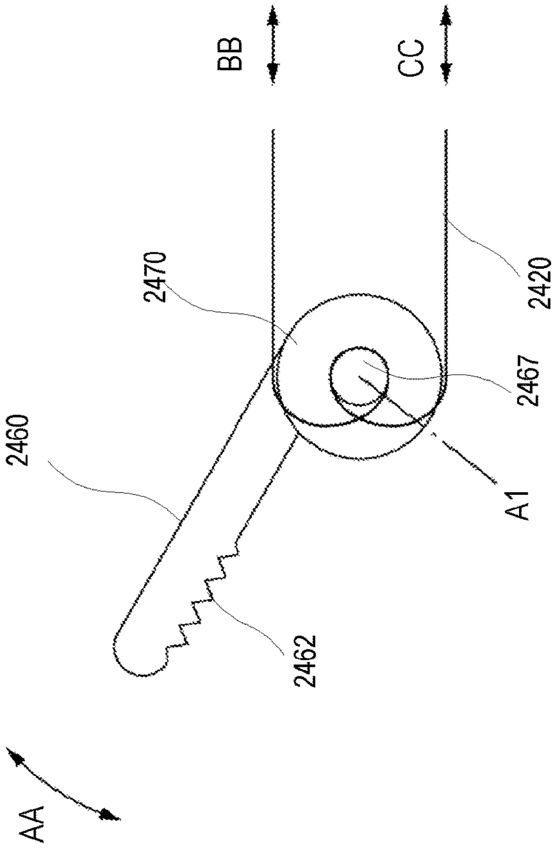
FIG. 6 is an enlarged view of a portion of the medical instrument of FIG. 5.

As described above, the distal end portion 2422 of the cable 2420 is coupled to the end effector 2460. More specifically, as shown in FIG. 5, the cable 2420 extends from the first capstan 2720 and is routed or wrapped about the end effector 2460. As shown in FIG. 6 the cable 2420 is first routed at least partially about a drive surface of the drive pulley 2470 and crosses over the drive pulley 2470 to start a wrap about the coupling spool 2467. The cable 2420 is wrapped at least one revolution about the coupling spool 2467 and then is crossed back over to the drive pulley 2470 before it exits and extends back to the mechanical structure 2700. In some embodiments, the cable 2420 is wrapped about the coupling spool 2467 more than one time or one revolution. For example, in some embodiments, the cable 2420 is wrapped about the coupling spool two times or three times and then is crossed back over to the drive pulley 2470. The second proximal end portion 2423 is then coupled to the second capstan 2720 in the same manner as the first proximal end portion 2421 is coupled to the first capstan 2710.

With the cable 2420 coupled to the mechanical structure 2700 and to the end effector 2460, rotational movement produced by the first capstan 2710 can cause the first proximal end portion 2421 of the cable 2420 to move in a direction BB, as shown in FIG. 6. Similarly, rotational movement about produced by the second capstan 2720 can cause the second proximal end portion 2423 of the cable 2420 to move in a direction CC as shown in FIG. 6. For example, the first capstan 2710 can be operable to produce rotational movement about the axis A3 as shown in FIG. 7A. The second capstan 2720 can similarly be operable to produce rotational movement about an axis (not shown) parallel to the axis A3. Thus, each of the first capstan 2710 and the second capstan 2720 can rotate in the direction of arrows DD in FIG. 5.

With each of the ends of the cable 2420 coupled to a separate capstan, the movement of a first portion of the cable 2420 can be controlled by one capstan (e.g., first capstan 2710) and movement of a second portion of the cable 2420 can be controlled by the other capstan (e.g., second capstan 2720). Thus, better control of the overall movement of the end effector 2460 can be achieved. For example, the first capstan 2710 can be actuated to produce a rotational movement about the axis $A_3$ in the direction of the arrow DD such that the first proximal end portion 2421 of the cable is moved in a first direction along arrows BB. Simultaneously, the second capstan 2720 can be actuated to produce rotational movement about an axis parallel to the axis A3 in an opposite direction as the first capstan 2710 such that the second proximal end portion 2723 of the cable 2420 is moved in an opposite direction as the first proximal end portion 2423 along arrows CC. Thus, the opposite movement of the first proximal end portion 2421 and the second proximal end portion 2423 causes the end effector 2460 to rotate (via the cable 2420 connection to the end effector 2460) about the rotational axis A1 (e.g., yaw movement).

Further, the first capstan 2710 can be actuated to produce a rotational movement about the axis $A_3$ in the direction of the arrow DD, while simultaneously, the second capstan 2720 can be actuated to produce rotational movement about an axis parallel to the axis A3 in the same direction as the first capstan 2710 such that the first proximal end portion 2421 of the cable and the second end portion 2423 of the cable 2420 are moved together in the same direction (along arrows BB and CC). The movement of the first proximal end portion 2421 and the second proximal end portion 2423 in the same direction causes the end effector 2460 to rotate (via the cable 2420 connection to the end effector 2460) about a second rotation axis (not shown) in the direction of arrow AA (e.g., pitch movement). Thus, the combination of the first capstan 2710, the second capstan 2720, and the single cable 2420 are operable to control the end effector 2460 of instrument 2400 in at least 2 DOFs (e.g., pitch and yaw).

The cable 2420, and any of the cables described herein can be formed from any suitable materials. For example, in some embodiments, any of the cables described herein can be formed from an ultra-high molecular weight polyethylene (UHMWPE) fiber. In some embodiments, any of the cables described herein can be constructed from a single strand or fiber. In other embodiments, any of the cables described herein can be constructed from multiple fibers woven or otherwise joined together to form the cable. In some embodiments, the cable 2420 or any of the cables described herein can include a coating or other surface treatment to enhance the frictional characteristics of the cable. Such enhanced frictional characteristics can help facilitate having the cable 2420 wrapped to the capstan without slipping and without the need for an additional retention feature.

In some embodiments, the cable 2420 and any of the cables described herein can be formed from a material having suitable temperature characteristics for use with cauterizing instruments. For example, such materials include Liquid crystal polymer (LCP), aramid, para-aramid and polybenzobisoxazole fiber (PBO). Such materials can provide frictional characteristics that enhance the ability for coupling and improve holding ability, for example, for coupling the cable 2420 to the capstan 2710 and end effector 2460. Such ability can also improve slip characteristics (e.g., help prevent the cable from slipping) during operation of the medical instrument. Such materials may or may not need a coating or other surface treatments to enhance the frictional characteristic.

Figure 8:
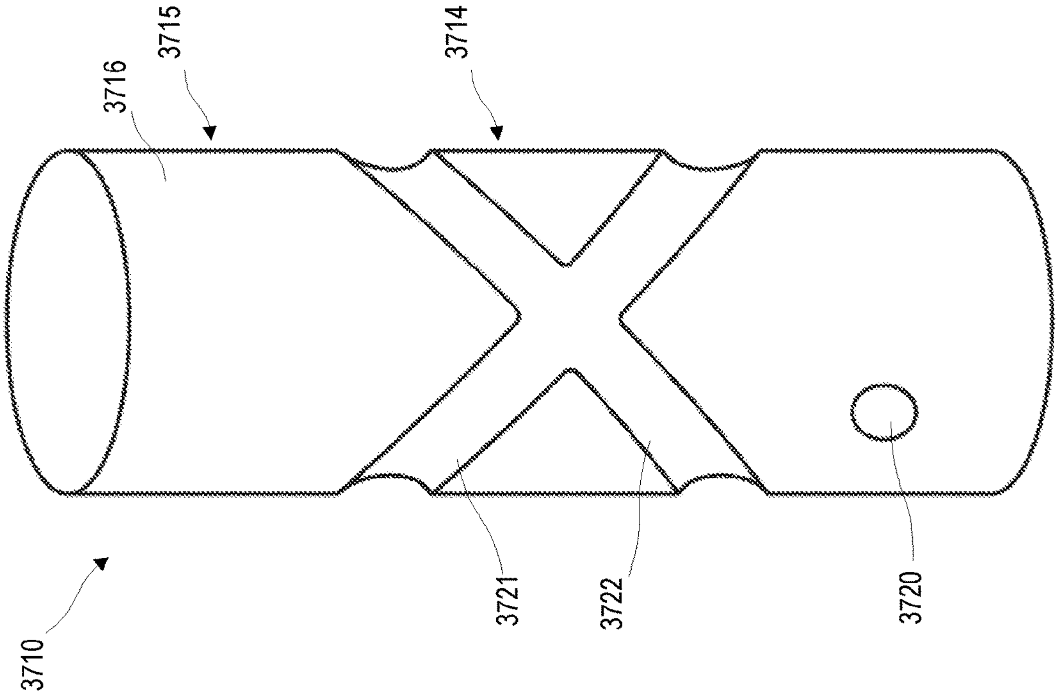
FIG. 8 is a perspective view of a capstan according to another embodiment.
Figure 9:
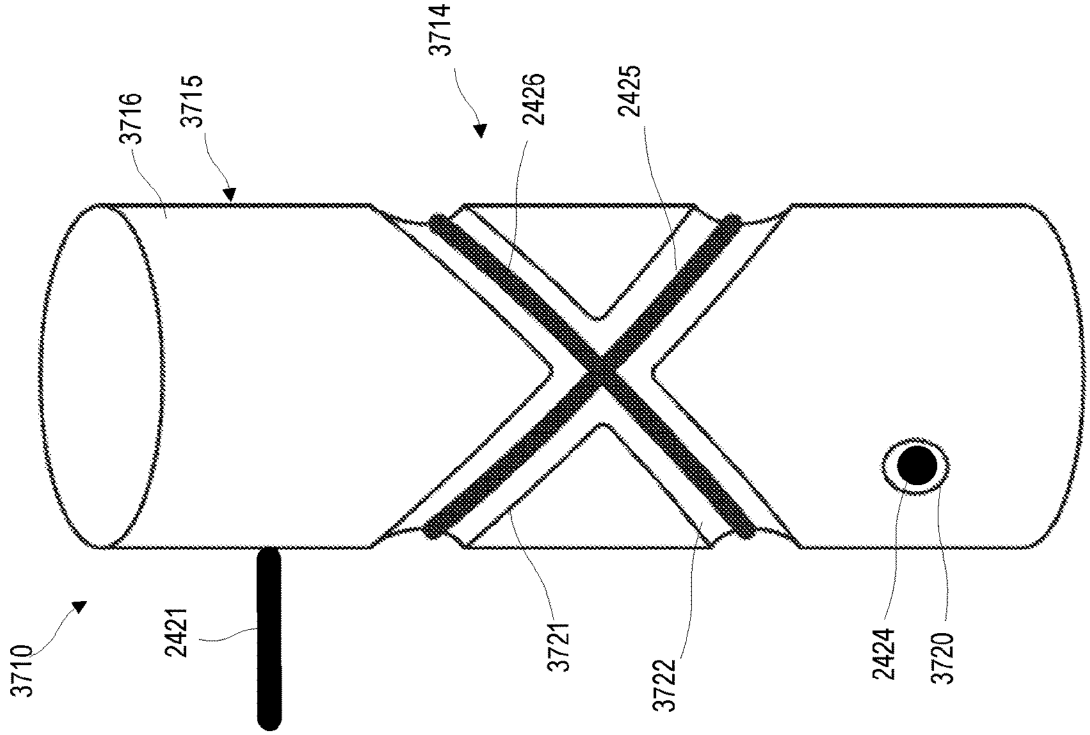
FIG. 9 is a perspective view of the capstan of FIG. 8 with a cable coupled thereto.
Figure 11:
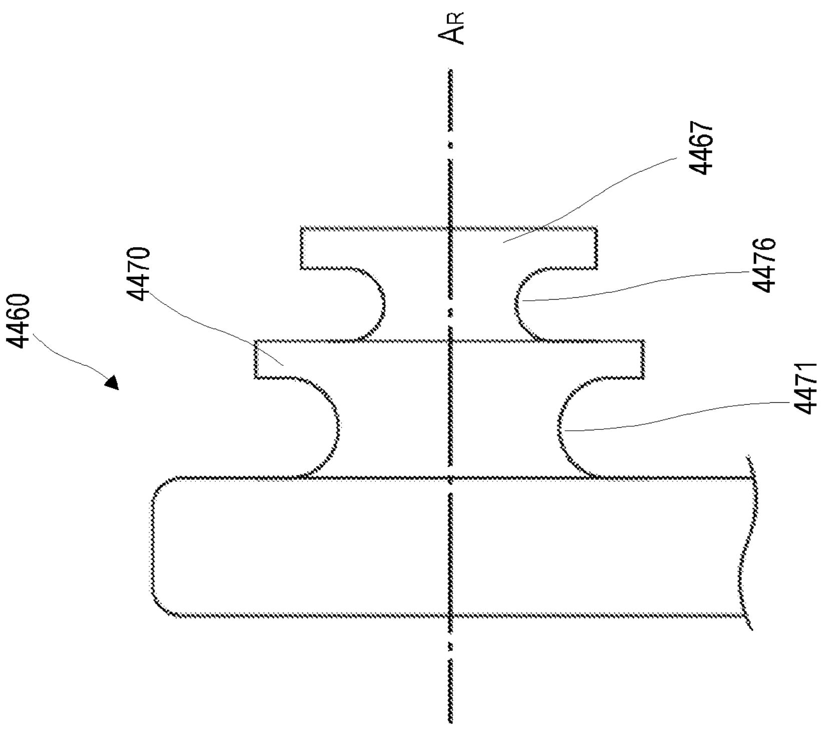
FIGS. 10 and 11 are a side view (FIG. 10) and an end view (FIG. 11) of a tool member according to an embodiment.
Figure 10:
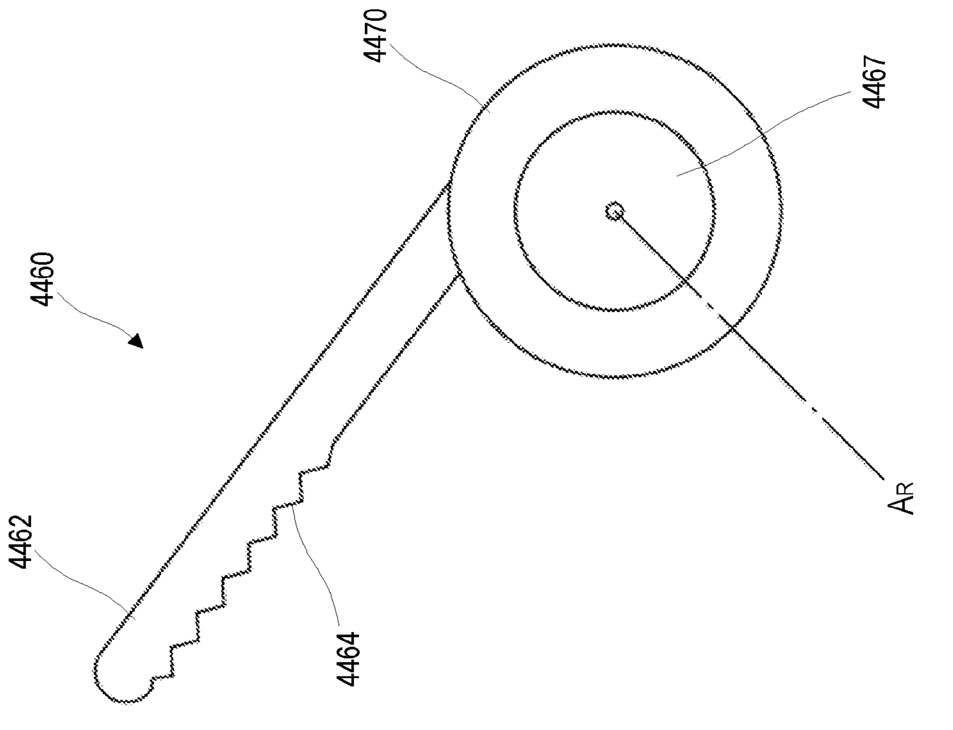

In some embodiments, a capstan can include one or more grooves or slots to facilitate wrapping of the cable to secure the cable to the capstan. For example, FIGS. 8 and 9 illustrate a capstan 3710 according to another embodiment. The capstan 3710 can be incorporated within any of the medical instruments described herein. The capstan 3710 includes a first portion 3715 (which functions as a spool portion) having a drive surface 3713, and a second portion 3714 (which functions as an anchor portion to secure the cable to the capstan 3710). In this embodiment, the second portion 3714 defines a first slot 3721 and a second slot 3722 that crosses the first slot 3721, and a termination opening 3720. Referring to the cable 2420 shown in FIG. 7B, FIG. 9 illustrates the cable 2420 coupled to the capstan 3710. More specifically, the first proximal end portion 2421 of the cable 2420 is coupled to the capstan 3710 such that a portion of the first proximal end portion 2421 wraps about the drive surface 3716 of the first portion 3715 of the capstan 3710, and is then wrapped about the second portion 3714 such that the first wrap portion 2425 of the cable 2420 is disposed within the first slot 3721, and a portion of the second wrap portion 2426 of the cable 2420 is disposed within the second slot 3722. As described above for capstan 2710, a portion of the first wrap portion 2425 crosses over a portion of the second wrap portion 2426 of the cable 2420. In addition, although not shown in FIG. 9, in some embodiments, at least one of the first wrap portion 2425 and the second wrap portion 2426 are wrapped about the capstan 3710 at least two times, or in other words, makes at least two revolutions about the capstan 3710. In some embodiments, at least one of the first wrap portion 2425 or the second wrap portion 2426 are wrapped about the capstan 3710 3 times (e.g., makes 3 revolutions about the capstan). In some embodiments, at least one of the first wrap portion 2425 or the second wrap portion 2426 are wrapped about the capstan 3710 more than 3 times. The multiple wraps or revolutions of the cable 2420 about the capstan 3710 assist in maintaining the cable 2420 secured to the capstan 3710 without the use of a retention element. In this embodiment, after wrapping about the second portion 3714, the termination portion 2424 of the cable 2420 is coupled within the termination opening 3720 defined in the capstan 3710 to assist in securing the cable 2420 to the capstan 3710.

FIGS. 10-13 illustrate an end effector 4460 according to an embodiment. The end effector 4460 can be incorporated within any of the medical instruments described herein, and can be configured the same or similar to, and function the same or similar to, other end effectors described herein. The end effector 4460 can be operatively coupled to a mechanical structure as described herein, such as mechanical structure 2700. For example, in some embodiments, the end effector 4460 can be coupled to a shaft of a medical instrument via a link.

The end effector 4460 includes at least one tool member 4462 that can include a contact portion 4464, a drive pulley 4470 and a coupling spool 4467. The contact portion 4464 is configured to engage or manipulate a target tissue during a surgical procedure. For example, in some embodiments, the contact portion 4464 can include an engagement surface that functions as a gripper, cutter, tissue manipulator, or the like. In other embodiments, the contact portion 4464 can be an energized tool member that is used for cauterization or electrosurgical procedures. The end effector 4462 can be operatively coupled to a mechanical structure (e.g., 2700) such that the tool member 4462 rotates about an axis of rotation $A_R$. For example, the drive pulley 4470 includes a drive surface 4471 configured to engage a cable 4420 (shown in FIGS. 12 and 13) such that a tension force exerted by the cable 4420 along the drive surface 4471 produces a rotation torque about the rotation axis $A_R$. In this manner, the contact portion 4464 of the tool member 4462 can be actuated to engage or manipulate a target tissue during a surgical procedure. In some embodiments, the tool member 4462 is coupled to the mechanical structure via a link coupled to a shaft.

The coupling spool 4467 includes a wrap surface 4476 to which a cable can be secured to the tool member 4462. The drive surface 4471 of the drive pulley 4470 is disposed at a first location on the tool member 4462 along the axis $A_R$, and the wrap surface 4476 is disposed at a second location offset from the first location along the axis $A_R$. In other words, the drive surface 4471 and the wrap surface 4476 are spaced apart from each other in a direction parallel to the axis $A_R$.

Figure 13:
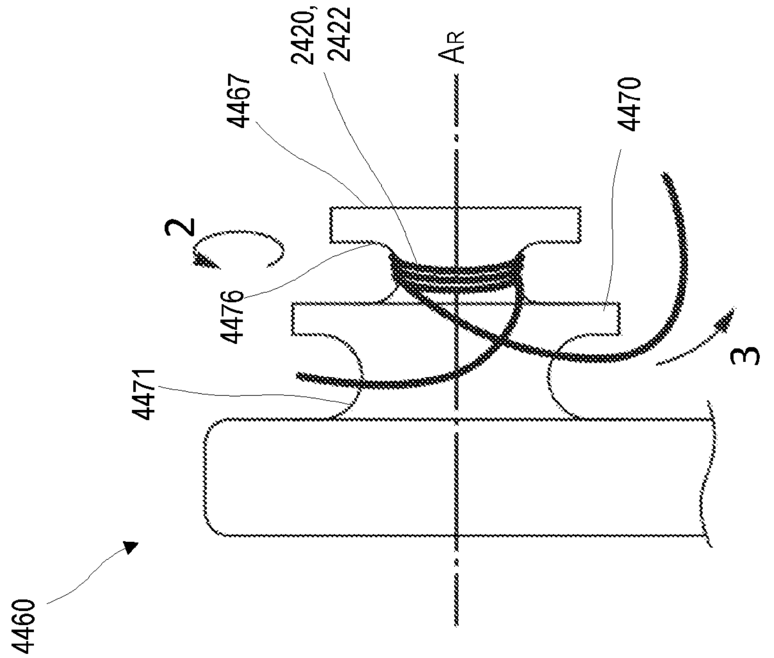
FIGS. 12 and 13 are end views of the tool member of FIG. 10 shown with a cable wrapped within the drive pulley (FIG. 12) of the tool member, and the cable further wrapped within the coupling spool (FIG. 13) of the tool member.
Figure 12:
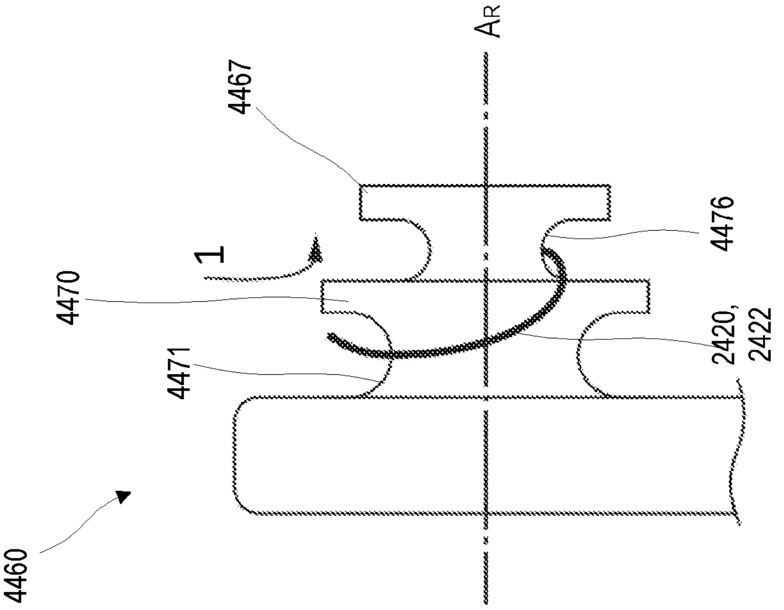
Figure 15:
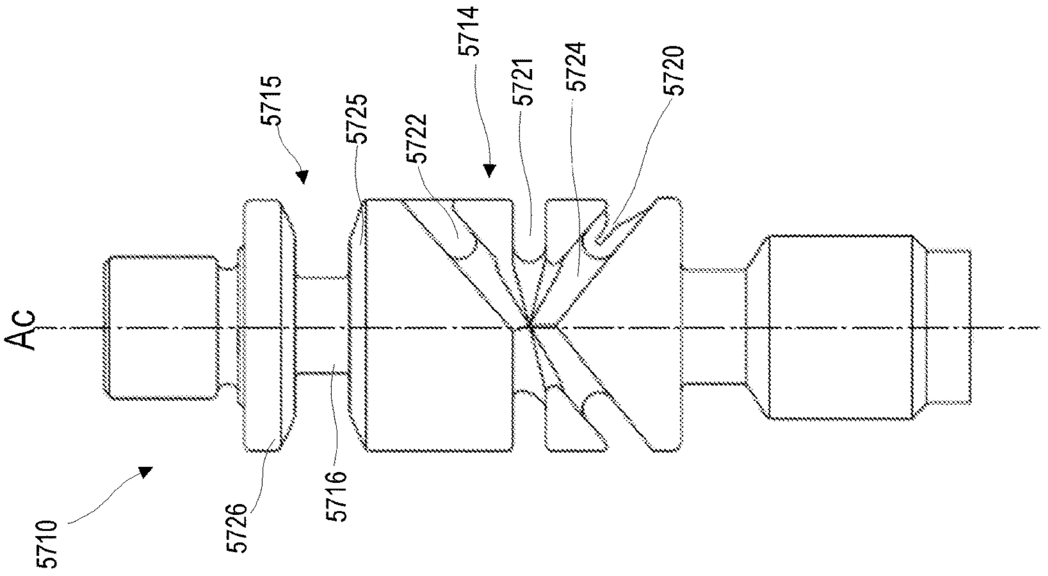
FIGS. 14 and 15 are each a different side view of a capstan according to another embodiment.

FIGS. 12 and 13 illustrate the routing path of the cable 2420 being coupled to the end effector 4460. More specifically, as described above for medical instrument 2400, the cable 2420 (described above with reference to FIG. 7B) can extend from a mechanical structure (not shown in FIGS. 10-13) along a shaft (not shown in FIGS. 10-13) and be routed about a first portion of the drive surface 4471 of the drive pulley 4470 as shown by arrow 1 in FIG. 12. The cable 2420 crosses over the drive pulley 4470 to start a wrap about the coupling spool 4467 as shown at arrow 2. The cable 2420 is wrapped at least one revolution about the wrap surface 4476 of the coupling spool 4467. In some embodiments, as shown in FIG. 13, the cable 4420 is wrapped about the coupling spool 4467 three times (shown at arrow 2). The cable 2420 is then crossed back over to the drive pulley 4470 where it is routed about a second portion of the drive surface 4471 before it exits the end effector 4460 and extends back to the mechanical structure as shown at arrow 3 in FIG. 13.

Figure 14:
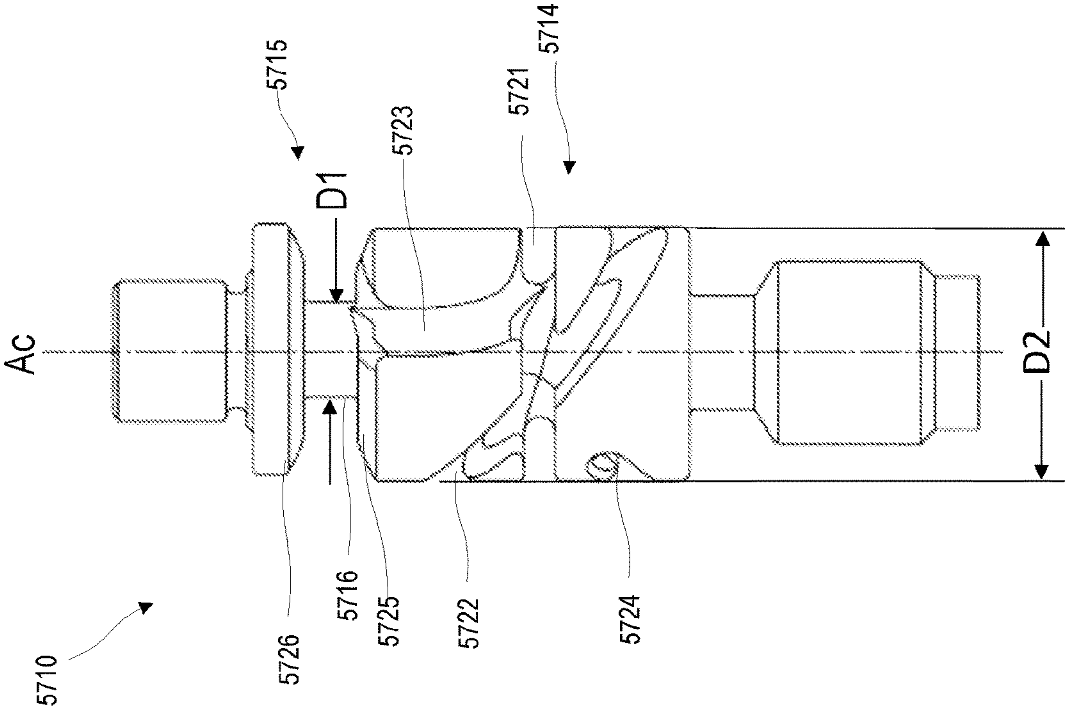
Figure 17:
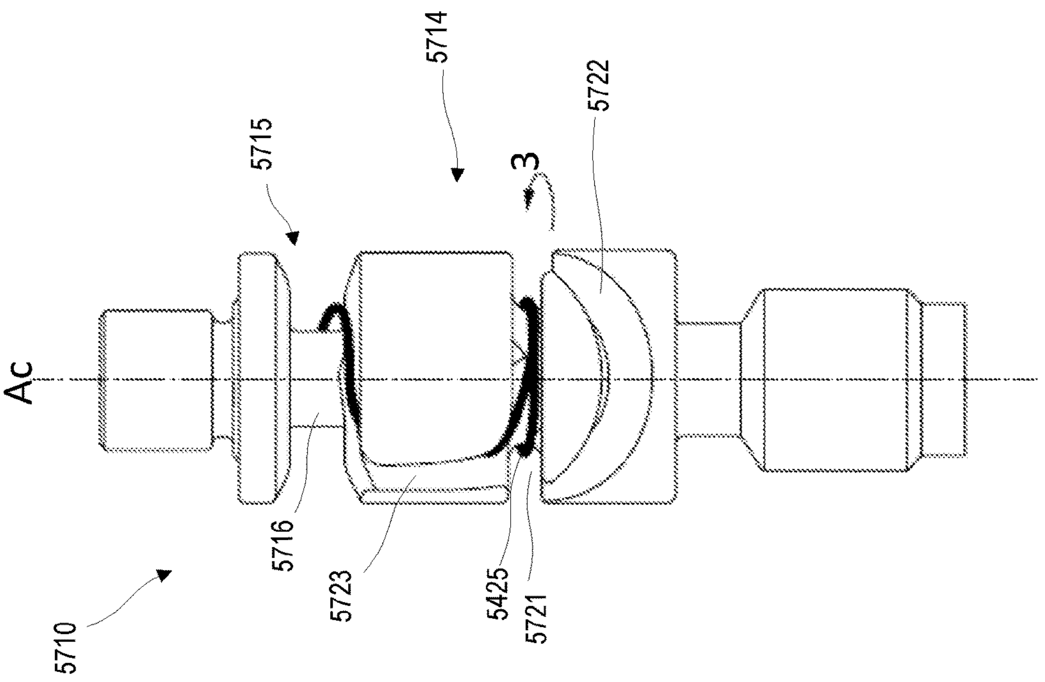
FIG. 17 is a side view of the capstan of FIGS. 14 through 16 rotated illustrating another side of the capstan with the cable further partially coupled thereto.
Figure 16:
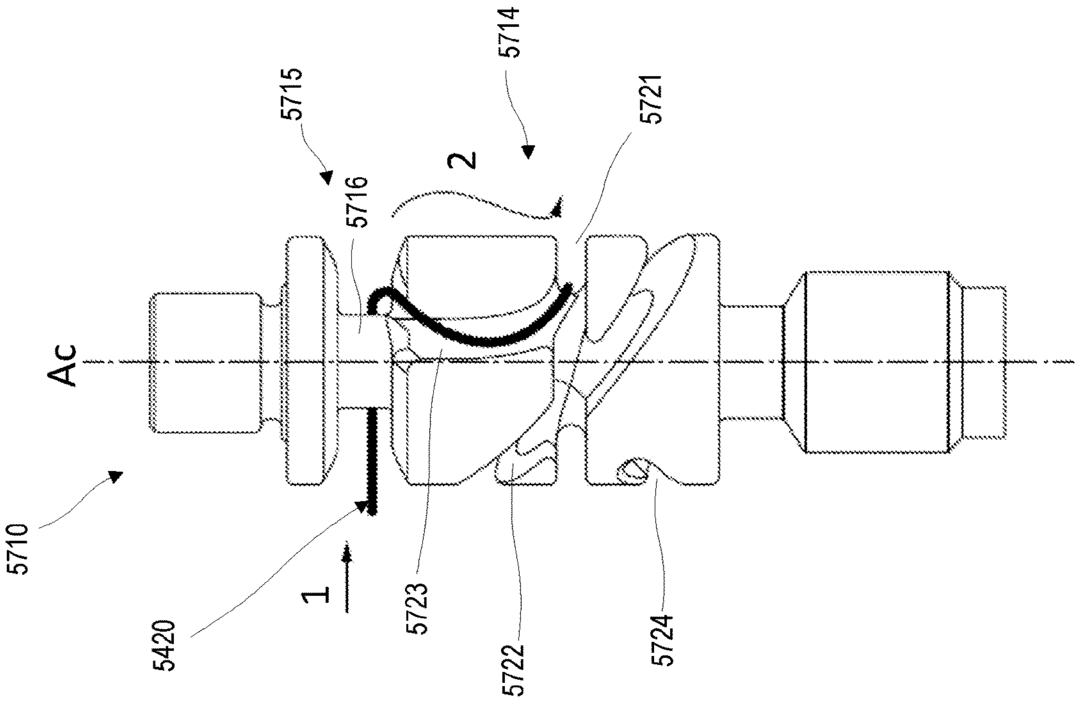
FIG. 16 is a side view of the capstan of FIGS. 14 and 15 rotated as shown in FIG. 14 and with a cable partially coupled thereto.
Figure 19:
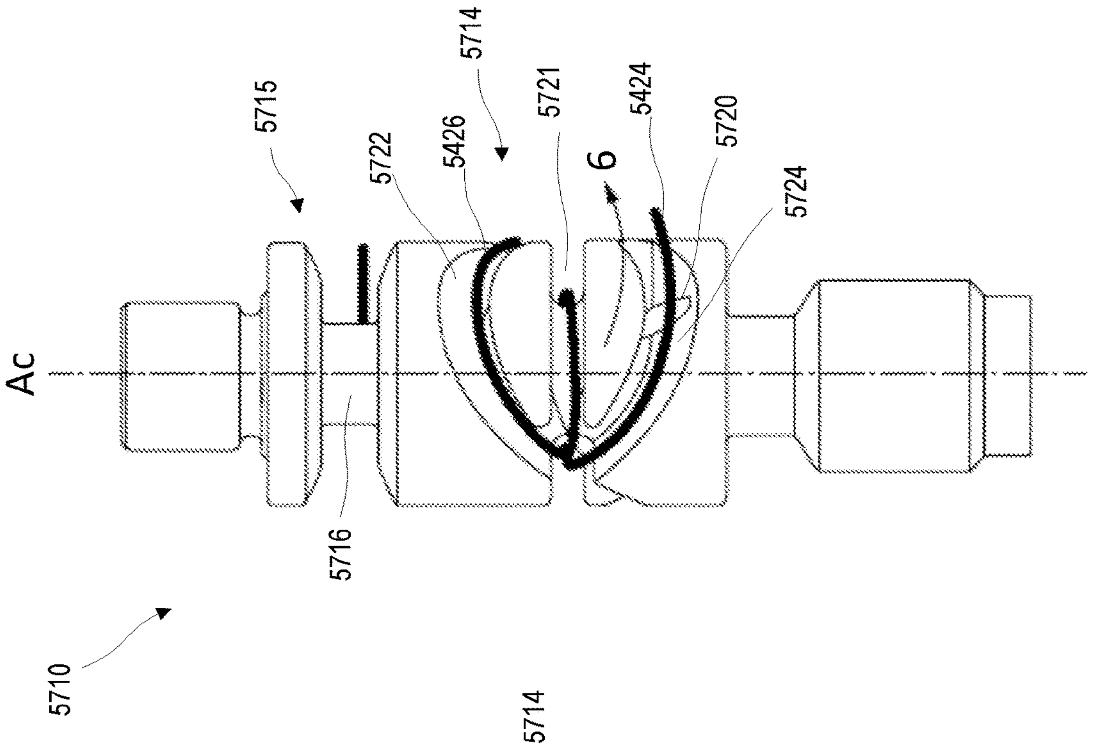
FIG. 19 is a side view of the capstan of FIGS. 14-18 rotated illustrating another side of the capstan with the cable of FIG. 14 coupled thereto.

FIGS. 14-19 illustrate a capstan 5710 according to an embodiment. The capstan 5710 can be incorporated within a mechanical structure 5700 (which can function as an "actuator" or a "transmission" or "transmission assembly" to move one or more components of a medical instrument) shown in FIG. 20 or in any of the medical instruments described herein. The capstan 5710 can be coupled to a cable 5420 (shown in FIGS. 16-19) in a similar manner as described above for capstans 2710 and 3710 and used to drive or actuate movement of an end effector (not shown) also coupled to the cable 5420. The capstan 5710 includes a first portion 5715 (which functions as a spool portion) having a drive surface 5716, and a second portion 5714 (which functions as an anchor portion to secure the cable to the capstan 5710). In this embodiment, the drive surface 5716 is a circular groove defined about a longitudinal axis Ac of the capstan 5710 between a first side wall 5725 and a second side wall 5726 of the capstan 5710. The circular groove defines a first diameter D1 as shown in FIG. 14.

The second portion 5714 of the capstan 5710 is cylindrical about the longitudinal axis Ac and defines a second diameter D2 that is greater than the first diameter D1 of the drive surface 5716. The second portion 5714 also defines a first slot 5721 and a second slot 5722 that crosses the first slot 5721, and a third slot 5724 that intersects the second slot 5722 and the first slot 5721. A passageway 5723 is defined within the first side wall 5725 and extends and intersects with the first slot 5721. Within the third slot 5724 a termination opening or groove 5720 is defined and configured to receive a termination portion of a cable as described in more detail below. The termination opening 5720 can have a width or diameter that is smaller than the width or diameter of the cable 5420 such that when a portion of the cable 5420 is disposed within the termination opening 5720 the friction fit will retain the cable 5420 thereto. For example, in some embodiments, the termination opening 5720 forms a pinch point to capture a portion of the cable 5420.

FIGS. 16-19 illustrate a cable 5420 being coupled to the capstan 5710. As described above for the cable 2420, the cable 5420 includes a first proximal portion 5421, a second proximal portion (not shown) and a distal portion (not shown). Although not shown in FIGS. 16-19, the distal portion can be coupled to any of the tool members described herein by any of the methods described herein. Although not shown, in FIGS. 16-19, the second proximal portion can be coupled to a second capstan in a similar manner as described below for the first proximal portion 5421. Thus, a detailed description is provided only for the attachment of the first proximal portion 5421 to the capstan 5710. The first proximal end portion 5421 includes a first wrap portion 5425, a second wrap portion 5426 and a termination portion 5424 (see FIGS. 18-19).

As described above for capstans 2710 and 3710, the first proximal end portion 5421 of the cable 5420 can be coupled to the capstan 5710 and routed along a particular path and secured thereto without the need for a separate retention element. More specifically, the first proximal end portion 5421 of the cable 5420 is routed about the drive surface 5716 of the first portion 5715 (as indicated at arrow 1 in FIG. 16) and through the passageway 5723 (as indicated by arrow 2 in FIG. 16). The first proximal end portion 5421 is then wrapped about the second portion 5714 such that the first wrap portion 5425 is disposed within the first slot 5721 as indicated by arrow 3 in FIG. 17. The first wrap portion 5425 is wrapped about the second portion 5714 within the first slot 5721 at least one time or in other words, the first wrap portion 5425 makes at least one revolution about the second portion 5714 within the first slot 5421. In some embodiments, the first wrap portion 5425 is wrapped about the second portion 5714 within the first slot 5721 at least two times or at least three times as indicated at arrow 3 in FIG. 17.

Figure 18:
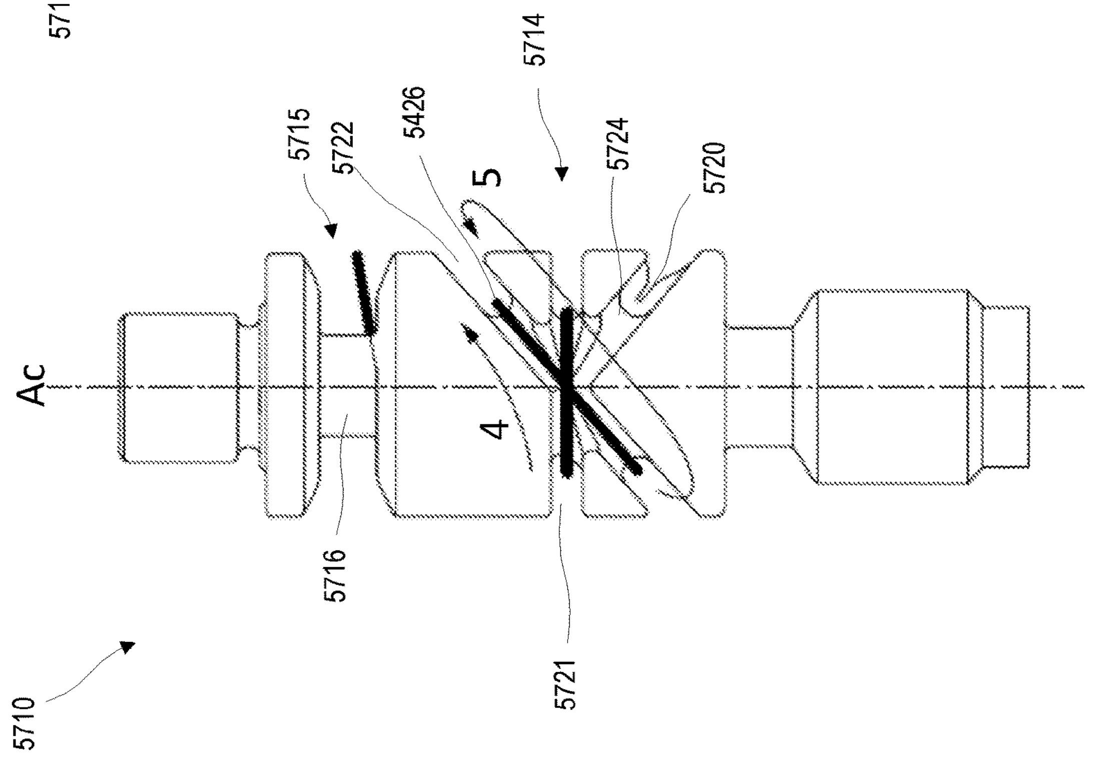
FIG. 18 is a side view of the capstan of FIGS. 14-17 rotated as shown in FIG. 15 and with the cable of FIG. 14 further partially coupled thereto.

The proximal end portion 5421 then passes up into the second slot 5722 (as indicated at arrow 4 in FIG. 18) and the second wrap portion 5426 is wrapped about the second portion 5714 within the second slot 5722 (as indicated at arrow 5 in FIG. 18) such that a portion of the second wrap portion 5426 crosses over a portion of the first wrap portion 5425 of the cable 5420, as shown in FIG. 18. The multiple wraps or revolutions of the cable 5420 about the capstan 5710 assist in maintaining the cable 5420 secured to the capstan 5710 without the use of a retention element. After wrapping about the second portion 5714 within the second slot 5722, the termination portion 5424 of the cable 5420 is routed into the third slot 5724 (as shown at arrow 6 in FIG. 19) and captured or disposed within the termination opening 5720 to further assist in securing the cable 5420 to the capstan 5710.

Figure 20:
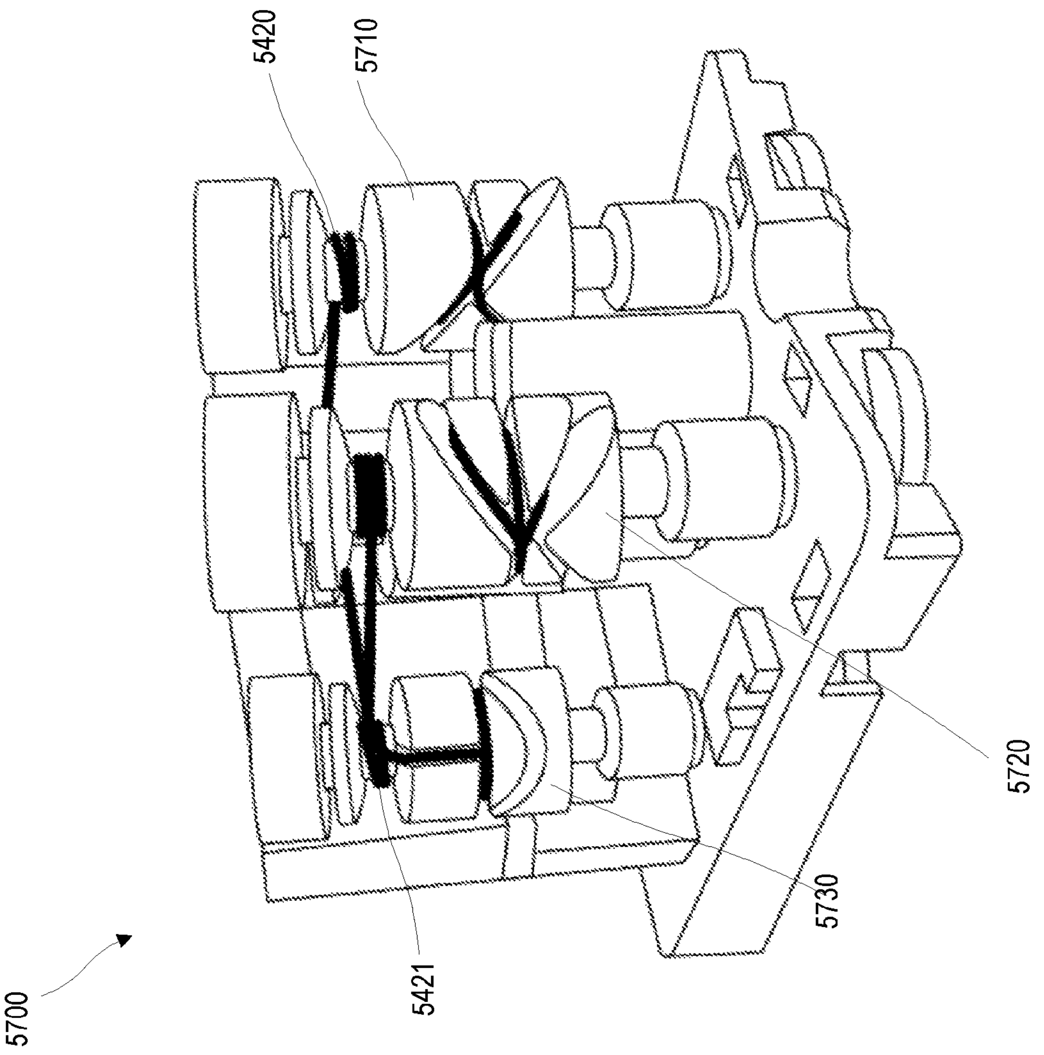
FIG. 20 is a perspective view of a portion of a mechanical structure, according to an embodiment.
Figure 21:
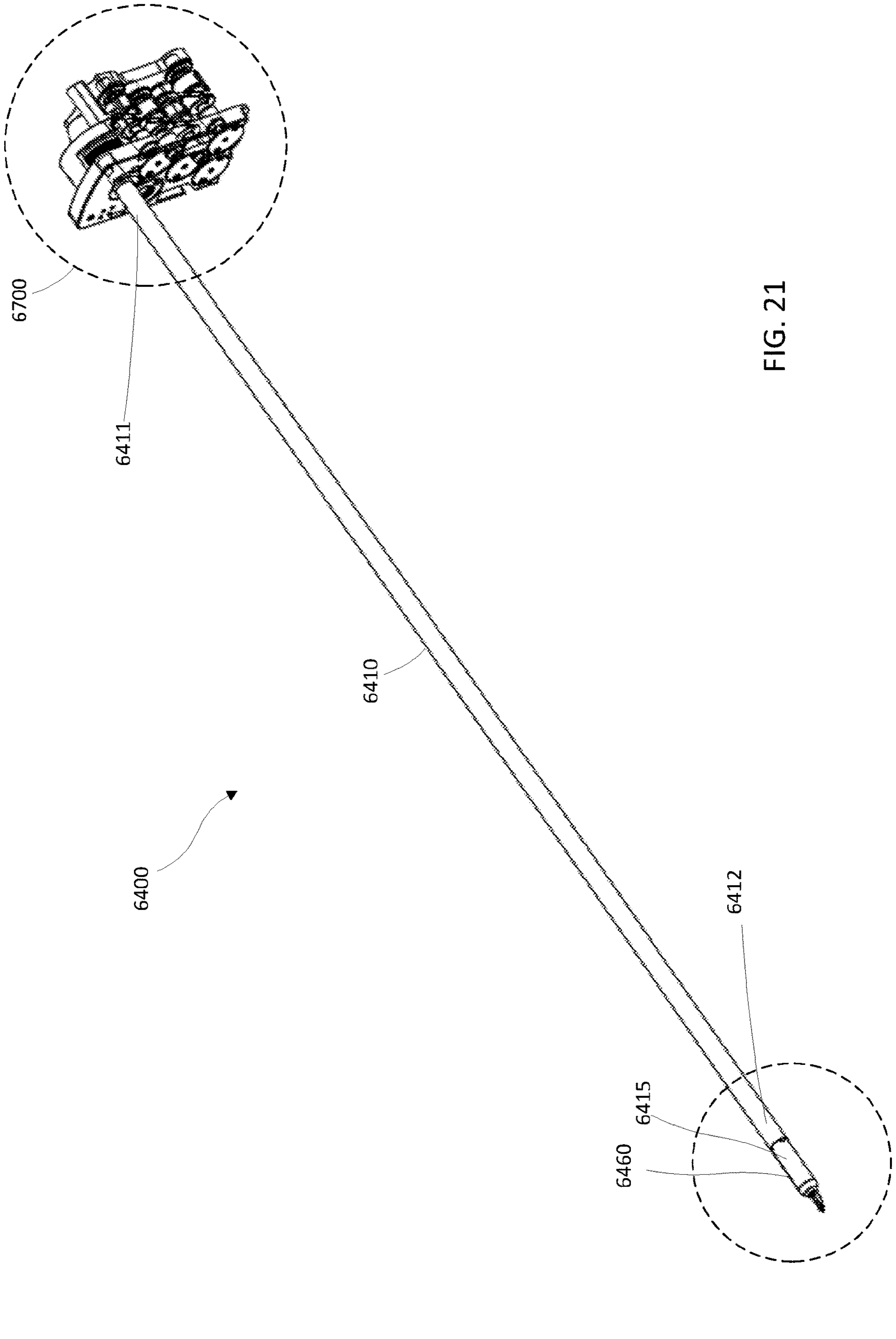
FIG. 21 is a perspective view of a medical instrument according to an embodiment.
Figure 22A:
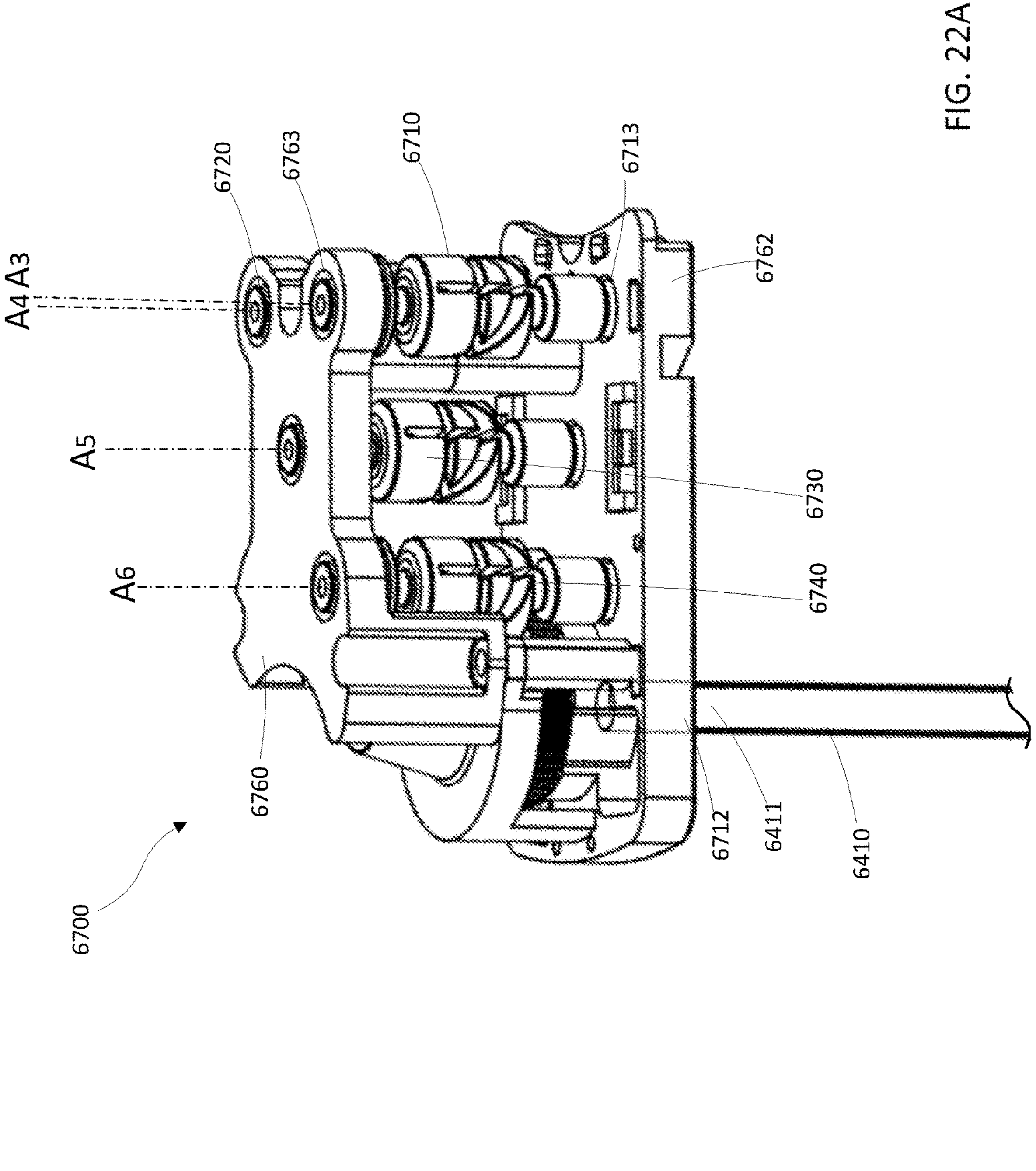
FIG. 22A is an enlarged perspective view of the mechanical structure and a portion of the shaft of the medical instrument of FIG. 21.
Figure 22B:
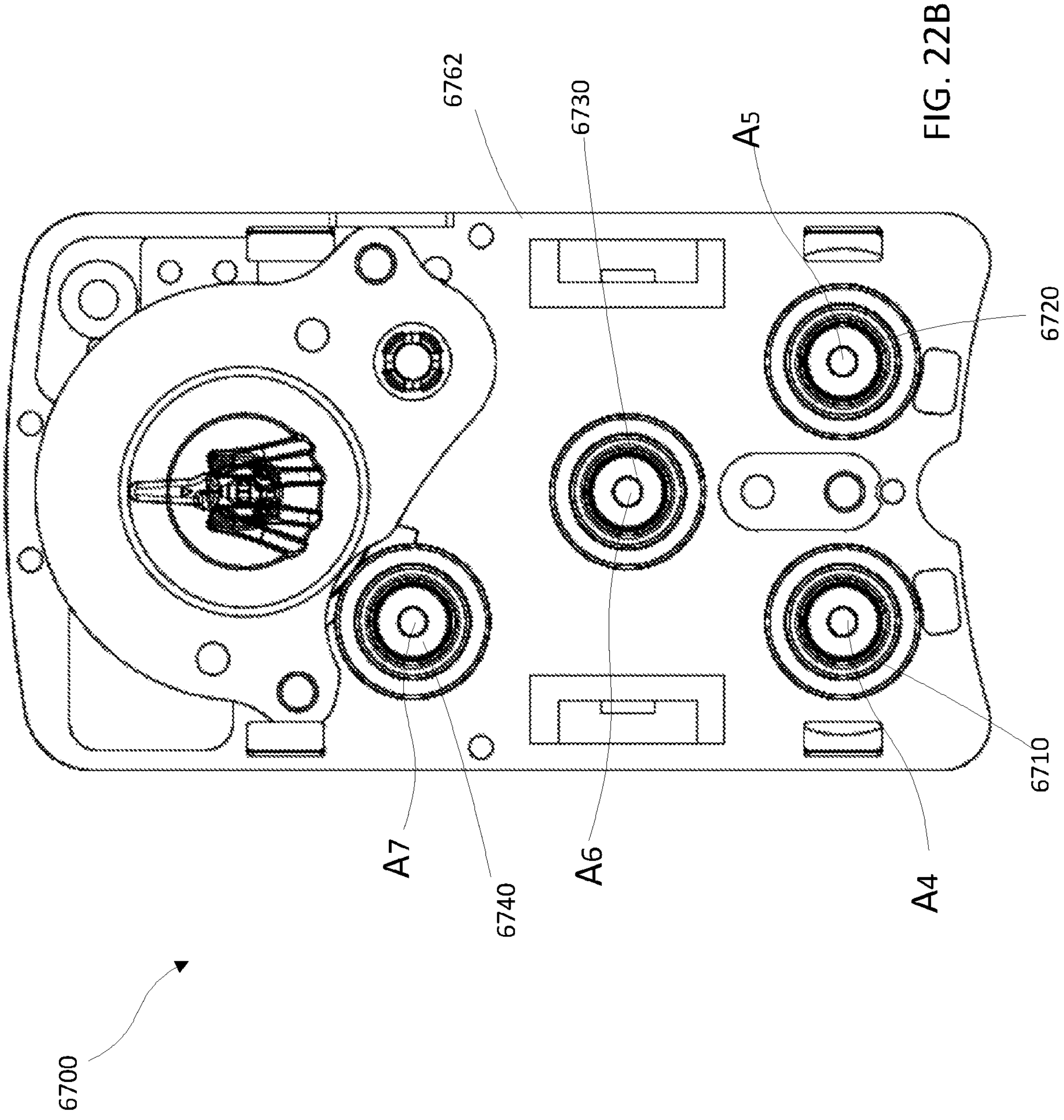
FIG. 22B is an end view of the mechanical structure of FIG. 22A with the housing removed.

FIG. 20 illustrates a portion of the mechanical structure 5700 according to an embodiment in which the capstan 5710 can be incorporated. The mechanical structure 5700 includes first pair of capstans: a first capstan 5710 and a second capstan 5720, and second pair of capstans: a third capstan 5730 and a fourth capstan (not shown in FIG. 20). Each pair of capstans are operatively coupled to a tool member of an end effector (not shown) and two proximal end portions of a single cable (e.g., a cable 5420) are connected to a different capstan of the pair of capstans.

The mechanical structure 5700 produces movement of the cable 5420 (via the capstans), which operates to produce the desired articulation movements (e.g., pitch, yaw, cut or grip) at the tool member of the end effector. For example, the mechanical structure 5700 includes components and controls to move a first portion of a first cable 5420 via the first capstan 5710 in a first direction (e.g., a proximal direction) and to move a second portion of the first cable 5420 via the second capstan 5720 in a second opposite direction (e.g., a distal direction). The mechanical structure 5700 can also move both the first portion of the first cable 5420 and the second portion of the first cable 5420 in the same direction. The mechanical structure 5700 can also include components and controls to move a first portion of a second cable via the third capstan 5730 and a second portion of the second cable via the fourth capstan (not shown in FIG. 20) in the same manner. In this manner, the mechanical structure 5700 can maintain the desired tension within the cables to produce the desired movements at the tool member of the end effector. For example, in some embodiments, an end effector can include two tool member portions that work together such as a jaw that is used to grip, in which a first pair of capstans controls movement of one of the two tool member portions and the second pair of capstans controls movement of the other tool member portion. In another example, an end effector can include more than one tool member in which one pair of capstans controls movement of a first tool member and the other pair of capstans controls movement of a second tool member.

FIGS. 21-36B are various views of an instrument 6400, according to an embodiment. In some embodiments, the instrument 6400 or any of the components therein are optionally parts of a surgical system that performs surgical procedures, and which can include a manipulator unit, a series of kinematic linkages, a series of cannulas, or the like. The instrument 6400 (and any of the instruments described herein) can be used in any suitable surgical system, such as the MIRS system 1000 shown and described above. The instrument 6400 includes a mechanical structure 6700, a shaft 6410, a wrist assembly 6500, an end effector 6460 and a cover 6415. Although not shown, the instrument 6400 also includes a first cable 6420 (a portion of which is shown in FIGS. 36A and 36B) and a second cable (not shown) that couple the mechanical structure 6700 to the wrist assembly 6500 and end effector 6460 as described in more detail below. The instrument 6400 is configured such that movement of the first cable 6420 and second cable produces rotation of the wrist assembly 6500 (i.e., pitch rotation) about a first axis of rotation $A_1$ (see FIGS. 27 and 28, which functions as a pitch axis, the term pitch is arbitrary), yaw rotation of the end effector 6460 about a second axis of rotation $A_2$ (see FIGS. 27 and 28, which functions as the yaw axis), a cutting rotation of the tool members of the end effector 6460 about the second axis of rotation $A_2$, or any combination of these movements. Changing the pitch or yaw of the instrument 6400 can be performed by manipulating the cables in a similar manner as that described above for the instrument 2400. Thus, the specific movement of each of the cables to accomplish the desired motion is not described below.

The shaft 6410 can be any suitable elongated shaft that couples the wrist assembly 6500 to the mechanical structure 6700. Specifically, the shaft 6410 includes a proximal end 6411 that is coupled to the mechanical structure 6700, and a distal end 6412 that is coupled to the wrist assembly 6500 (e.g., a proximal link of the wrist assembly 6500. The shaft 6410 defines a lumen (not shown) or multiple passageways through which the cables and other components (e.g., electrical wires, ground wires, or the like) can be routed from the mechanical structure 6700 to the wrist assembly 6500. The cover 6415 (see FIG. 26) is disposed over the wrist assembly 6500 and at least a portion of the end effector 6460.

Although not shown, the first cable 6420 and the second cable each include a first proximal portion, a second proximal portion and a distal portion. As described above for cable 2420, the first proximal end portion and the second proximal end portion are each coupled to the mechanical structure 6700 in the same manner as described above for mechanical structure 2700 of instrument 2400 and as described in more detail below. In some embodiments, the cables can be constructed from a polymer as described above for the cable 2420.

The mechanical structure 6700 includes a base 6762 and a housing 6760, and the housing 6760 can be attached to the base 6762 via one or more fastening members. In some embodiments, the base 6762 and housing 6760 may partially enclose or fully enclose components disposed within the mechanical structure 6700. The base 6762 and the housing 6760 provide structural support for mounting and aligning components in the mechanical structure 6700. For example, the base 6762 defines a shaft opening 6712 within which the proximal end 6411 of the shaft 6410 is mounted. The base 6762 further defines one or more bearing surfaces or openings 6713 within which the capstans (6710, 6720, 6730 and 6740) are mounted and rotatably supported. In some embodiments, the housing 6760 includes one more bearing surfaces or openings 6763 within which the capstans are mounted. The openings 6763 of the housing 6760 can be axially aligned with the openings 6713 of the base 6762. In addition to providing mounting support for the internal components of the mechanical structure 6700, the base 6762 can include external features (e.g., recesses, clips, etc.) that interface with a docking port of a drive device (not shown). The drive device can be, for example, a handheld system or a computer-assisted teleoperated system that can receive the instrument 6400 and manipulate the instrument 6400 to perform various surgical operations. The drive device can include one or more motors to drive capstans s of the mechanical structure 6700. In other embodiments, the drive device can be an assembly that can receive and manipulate the instrument 6400 to perform various operations.

The mechanical structure 6700 includes a first capstan 6710 a second capstan 6720 (see FIG. 22B which shows the mechanical structure 6700 with the housing 6760 removed for illustration purposes), a third capstan 6730 and a fourth capstan. Each of the capstans (6710, 6720, 6730 and 6740) is mounted to the mechanical structure 6700 (e.g., within the housing 6760) via a capstan support member (not shown). For example, the capstan support member can be a mount, shaft, or any other suitable support structure to secure the capstans to the mechanical structure 6700.

Each of capstans 6710, 6720, 6730, 6740 is rotatably supported within a corresponding opening, such as opening 6713 of the base 6762, and within a corresponding opening 6763 of the housing 6760 (as shown in FIG. 22). Each of capstans 6710, 6720, 6730, 6740 can be driven by a corresponding motor in the drive device. For example, the first capstan 6710 can be driven to rotate about a first capstan axis $A_3$, the second capstan 6720 can be driven to rotate about a second capstan axis $A_4$, the third capstan 6730 can be driven to rotate about a third capstan axis $A_5$, and the fourth capstan 6740 can be driven to rotate about a fourth capstan axis $A_6$.

The first cable 6420 is routed between the mechanical structure 6700, the wrist assembly 6500 and the end effector 6460 and is coupled to the first capstan 6710 and the second capstan 6720 of the mechanical structure 6700. The second cable is also routed between the mechanical structure 6700, the wrist assembly 6500 and the end effector 6460 and is coupled to the third capstan 6730 and the fourth capstan 6740 of the mechanical structure 6700. More specifically, with reference to the first cable 6420, the first proximal end portion of the first cable 6420 is coupled to the first capstan 6710 of the mechanical structure 6700, the first cable 6420 extends from the first capstan 6710 along the shaft 6410, is routed through the wrist assembly 6500, and the distal end portion of the cable 6410 is coupled to the end effector 6460, as described above for instrument 2400. The first cable 6420 can extend within the interior lumen of the shaft 6410 or can be routed exterior to the shaft 6410. The first cable 6420 then extends from the end effector 6460 back along the shaft 6410 and the second proximal end portion is coupled to the second capstan 6720 of the mechanical structure 6700. In other words, the two ends of a single cable (e.g., first cable 6420) are coupled to and actuated by two separate capstans (capstans 6710 and 6720) of the mechanical structure 6700.

More specifically, the two ends of the first cable 6420 that are associated with opposing directions of a single degree of freedom are connected to two independent drive capstans 6710 and 6720. This arrangement, which is generally referred to as an antagonist drive system, allows for independent control of the movement of (e.g., pulling in or paying out) each of the ends of the cable. The mechanical structure 6700 produces movement of the first cable 6420 and the second cable, which operates to produce the desired articulation movements (pitch, yaw, cutting or gripping) at the end effector 6460. Accordingly, as described herein, the mechanical structure 6700 includes components and controls to move a first portion of the first cable 6420 via the first capstan 6710 in a first direction (e.g., a proximal direction) and to move a second portion of the first cable 6420 via the second capstan 6720 in a second opposite direction (e.g., a distal direction). The mechanical structure 6700 can also move both the first portion of the first cable 6420 and the second portion of the first cable 6420 in the same direction. The mechanical structure 6700 also includes components and controls to move a first portion of the second cable via the third capstan 6730 in a first direction (e.g., a proximal direction) and to move a second portion of the second cable via the fourth capstan 6740 in a second opposite direction (e.g., a distal direction). The mechanical structure 6700 can also move both the first portion of the second cable and the second portion of the second cable in the same direction. In this manner, the mechanical structure 6700 can maintain the desired tension within the cables to produce the desired movements at the end effector 6460.

Figure 24:
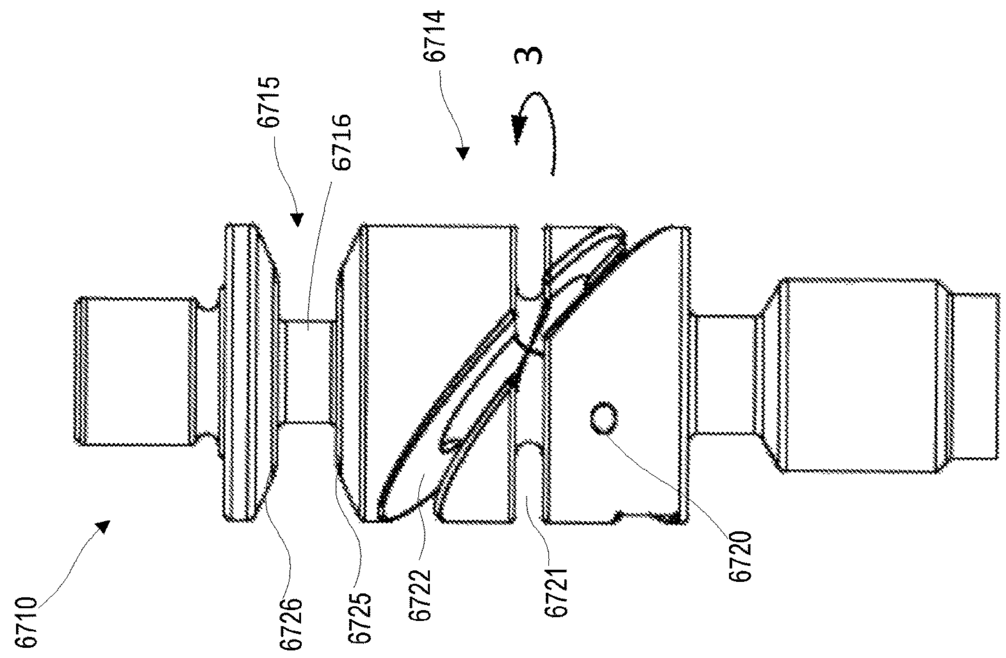
FIGS. 23-25 are each a different side perspective view of a capstan of the mechanical structure of FIGS. 22A and 22B.
Figure 23:
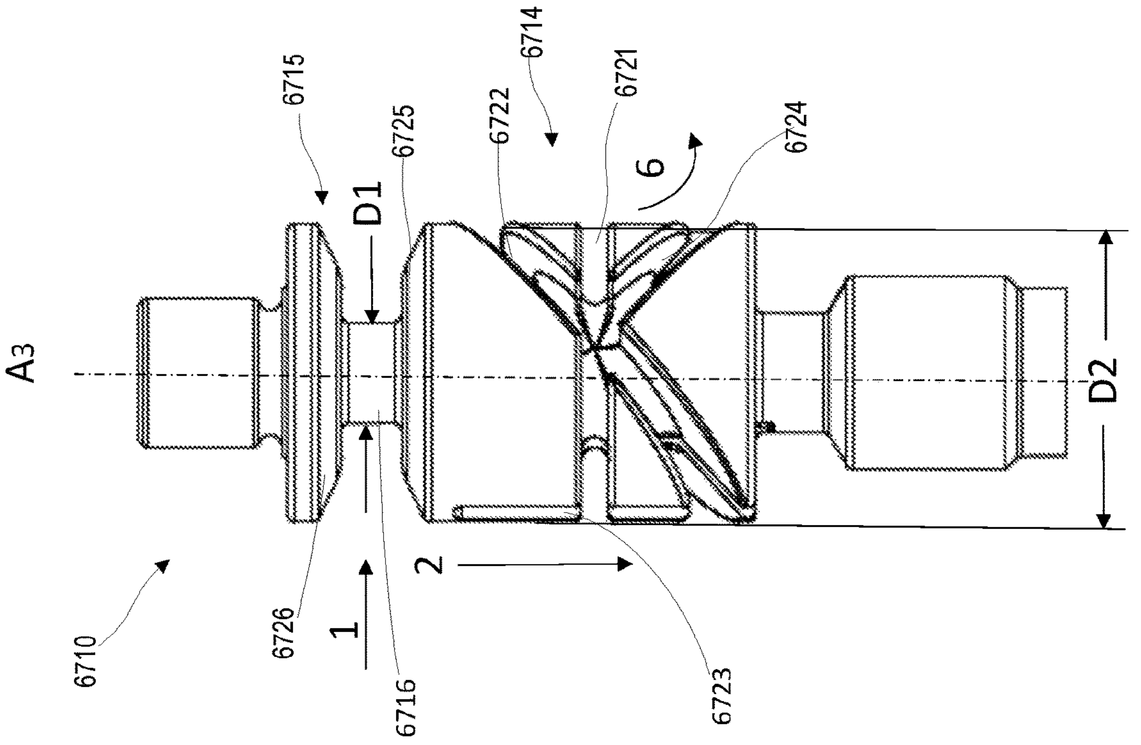
Figure 25:
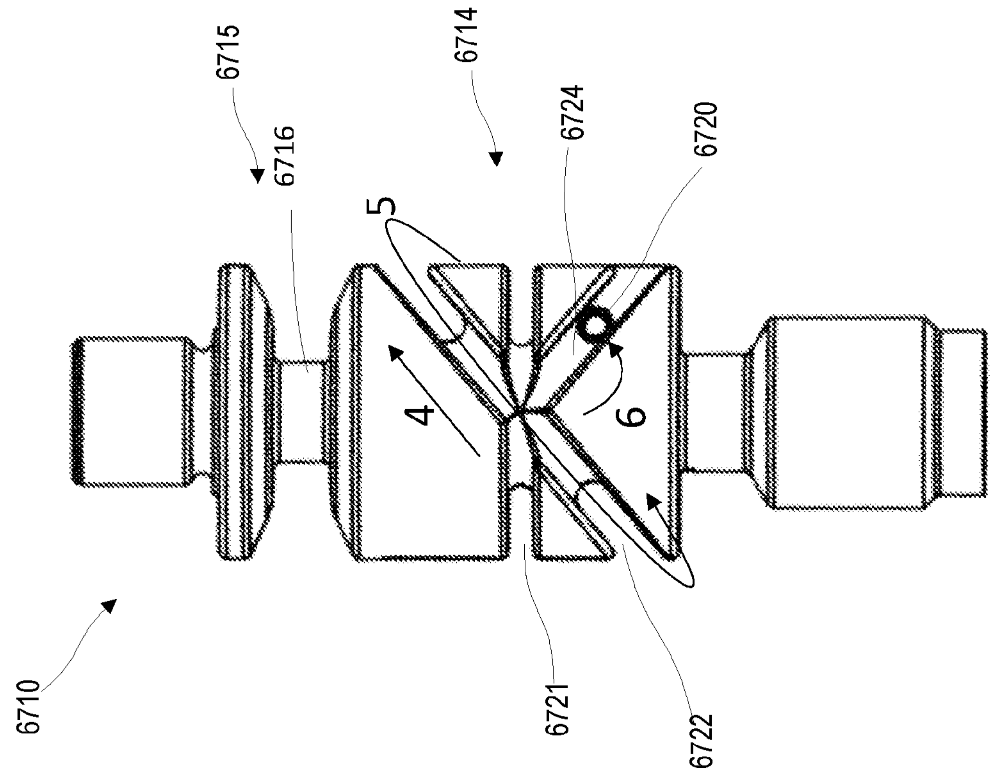
Figure 26:
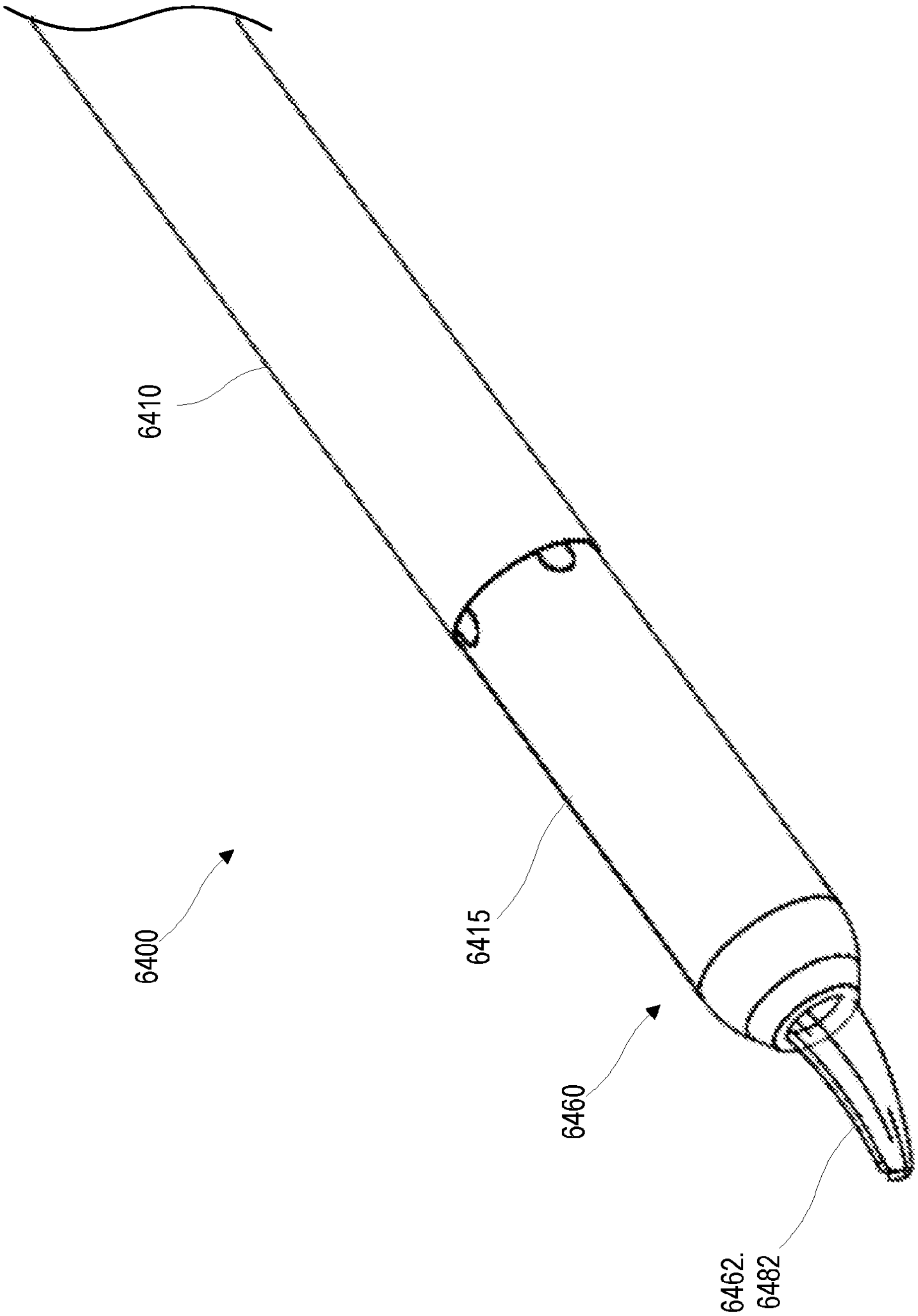
FIG. 26 is an enlarged perspective view of a distal end portion of the medical instrument of FIG. 21.

As shown in FIGS. 23-25, the first capstan 6710 includes a first portion 6715 (which functions as a spool portion) having a drive surface 6716, and a second portion 6714 (which functions as an anchor portion to secure the cable to the capstan 6710). In this embodiment, the drive surface 6716 is a circular groove defined about a longitudinal axis $A_3$ of the capstan 6710 between a first side wall 6725 and a second side wall 6726 of the capstan 6710. The circular groove defines a first diameter D1 as shown in FIG. 23.

The second portion 6714 of the first capstan 6710 is cylindrical about the longitudinal axis A3 and defines a second diameter D2 that is greater than the first diameter D1 of the drive surface 6716. The second portion 6714 also defines a first slot 6721 and a second slot 6722 that crosses the first slot 6721, and a third slot 5724 the intersects the second slot 6722 and the first slot 6721. A passageway 6723 is defined within the first side wall 6725 and extends and intersects with the first slot 6721. Within the third slot 6724 a termination opening 6720 is defined and configured to receive a termination portion of the first cable. The termination opening 6720 can have a portion of a width or diameter that is smaller than the width or diameter of the cable such that when a portion of the first cable 6420 is disposed within the termination opening 6720 the friction fit will retain the cable 6420 thereto. For example, in some embodiments, the termination opening 6720 forms a pinch point to capture a portion of the cable or is a tapered lumen.

As described above, the first cable 6420 is coupled to each of the first capstan 6710 and the second capstan 6720 and also to wrist assembly 6500 and the end effector 6460. More specifically, the first proximal end portion and the second proximal end portion are each coupled to the respective first capstan 6710 and second capstan 6720 along a specific wrap path. The wrap path for the first proximal end portion of the first cable 6420 on the first capstan 6710 and the second proximal end portion of the first cable 6420 on the second capstan 6720 can be the same or similar to the wrap path described above for capstan 5700. Further, specific details described below for the first capstan 6710 can also apply to the second capstan 6720, the third capstan 6730 and the fourth capstan 6740. In addition, the second cable can be coupled to the third capstan 6730, the wrist assembly 6500, the end effector 6460 and the fourth capstan 6740 in the same or similar manner as described for the first cable 6420.

Although not shown, the first proximal end portion of the first cable 6420 includes a first wrap portion, a second wrap portion and a termination portion similar to cable 2420 described above. As described above for capstan 5700, the first proximal end portion of the first cable 6420 can be coupled to the first capstan 6710 and routed along a particular path and secured thereto without the need for a separate retention element. More specifically, the first proximal end portion of the first cable 6420 is routed about the drive surface 6716 of the first portion 6715 (as indicated at arrow 1 in FIG. 23) and through the passageway 6723 (as indicated by arrow 2 in FIG. 23). The first proximal end portion is then wrapped about the second portion 6714 such that the first wrap portion of the first cable 6420 is disposed within the first slot 6721 as indicated by arrow 3 in FIG. 24. The first wrap portion is wrapped about the second portion 6714 within the first slot 6721 at least one time or in other words, the first wrap portion makes at least one revolution about the second portion 6714 within the first slot 6421. In some embodiments, the first wrap portion is wrapped about the second portion 6714 within the first slot 6721 at least two times or at least three times.

The proximal end portion of the first cable 6420 then passes up into the second slot 6722 (as indicated at arrow 4 in FIG. 24) and the second wrap portion is wrapped about the second portion 6714 within the second slot 6722 (as indicated at arrow 5 in FIG. 25) such that a portion of the second wrap portion crosses over a portion of the first wrap portion of the first cable 6420 in a similar manner as shown for capstan 5700 in FIG. 18. The multiple wraps or revolutions of the first cable 6420 about the first capstan 6710 assist in maintaining the first cable 6420 secured to the capstan 6710 without the use of a retention element. After wrapping about the second portion 6714 within the second slot 6722, the termination portion of the first cable 6420 is routed into the third slot 6724 and captured or disposed within the termination opening 6720 to further assist in securing the first cable 6420 to the first capstan 6710.

Figure 27:
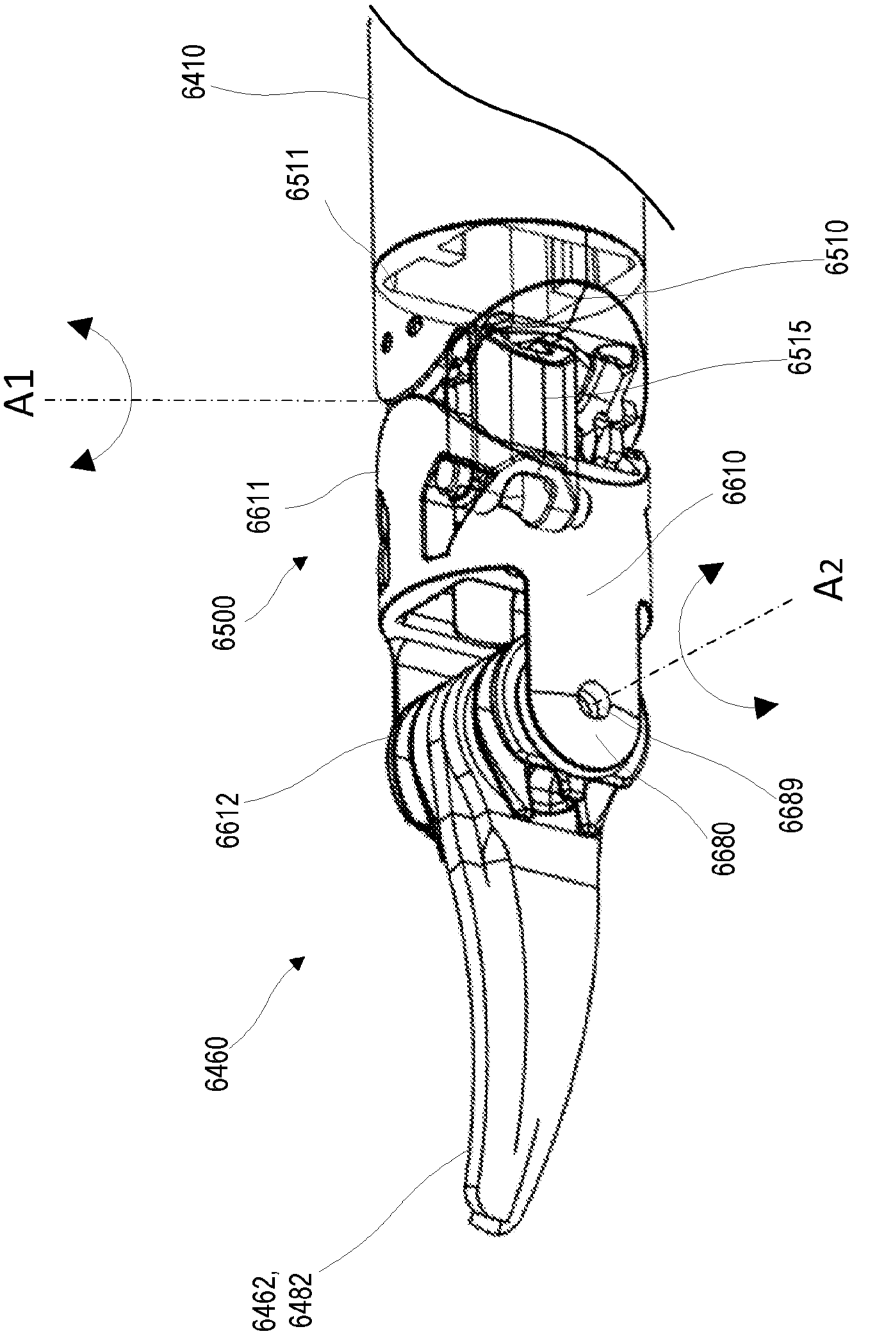
FIG. 27 is a perspective view of the distal end portion of the medical instrument of FIG. 21 with an outer cover removed and the tool member in a closed position.

Referring to FIG. 27, the wrist assembly 6500 (also referred to as a joint assembly) includes a first link 6510, a second link 6610 and a third link 6515. The first link 6510 has a proximal portion 6511 and a distal end portion 6512. The proximal end portion is coupled to the shaft 6410. The proximal portion 6511 can be coupled to the shaft 6410 via any suitable mechanism. For example, in some embodiments, the proximal portion 6511 can be matingly disposed within a portion of the shaft 6410 (e.g., via an interference fit). In some embodiments, the proximal portion 6511 can include one or more protrusions, recesses, openings, or connectors that couple the proximal portion 6511 to the shaft 6410. In some embodiments, the proximal portion 6511 can be welded, glued, or fused to the shaft 6410.

Figure 28:
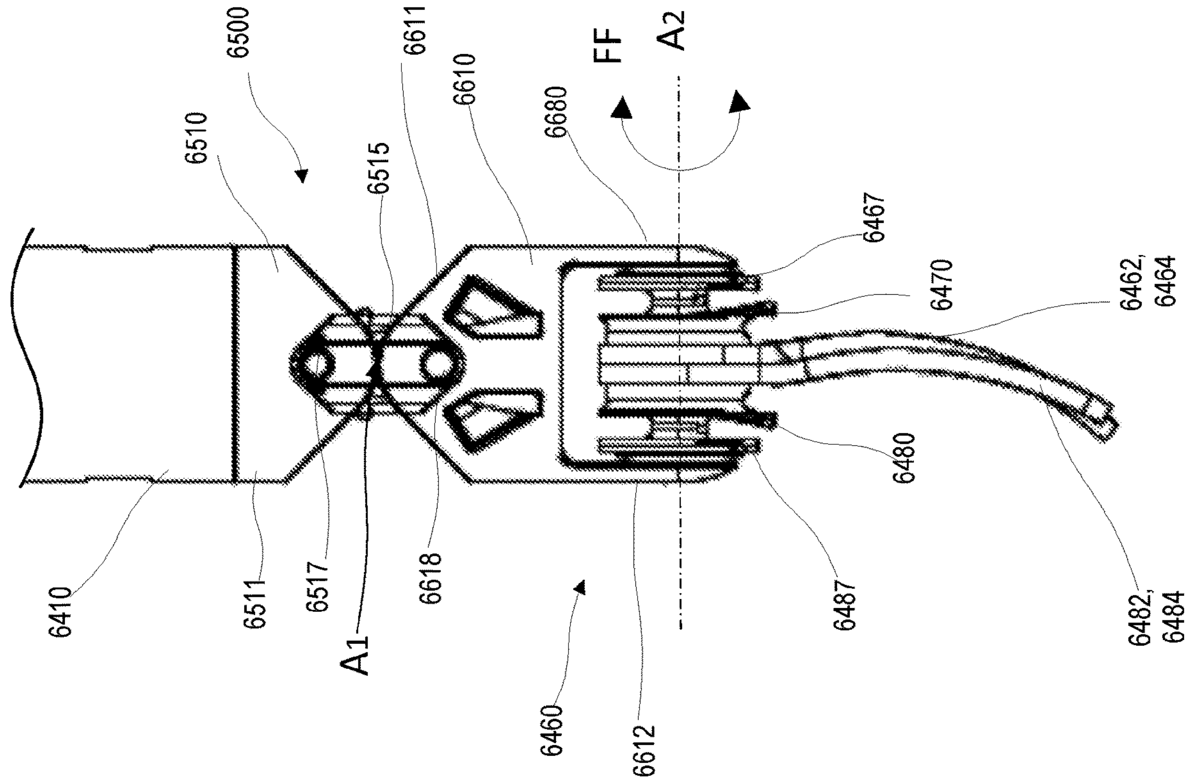
FIG. 28 is a top view of the distal end portion of the medical instrument of FIG. 21 with the outer cover removed and the end effector in the closed position.
Figure 29:
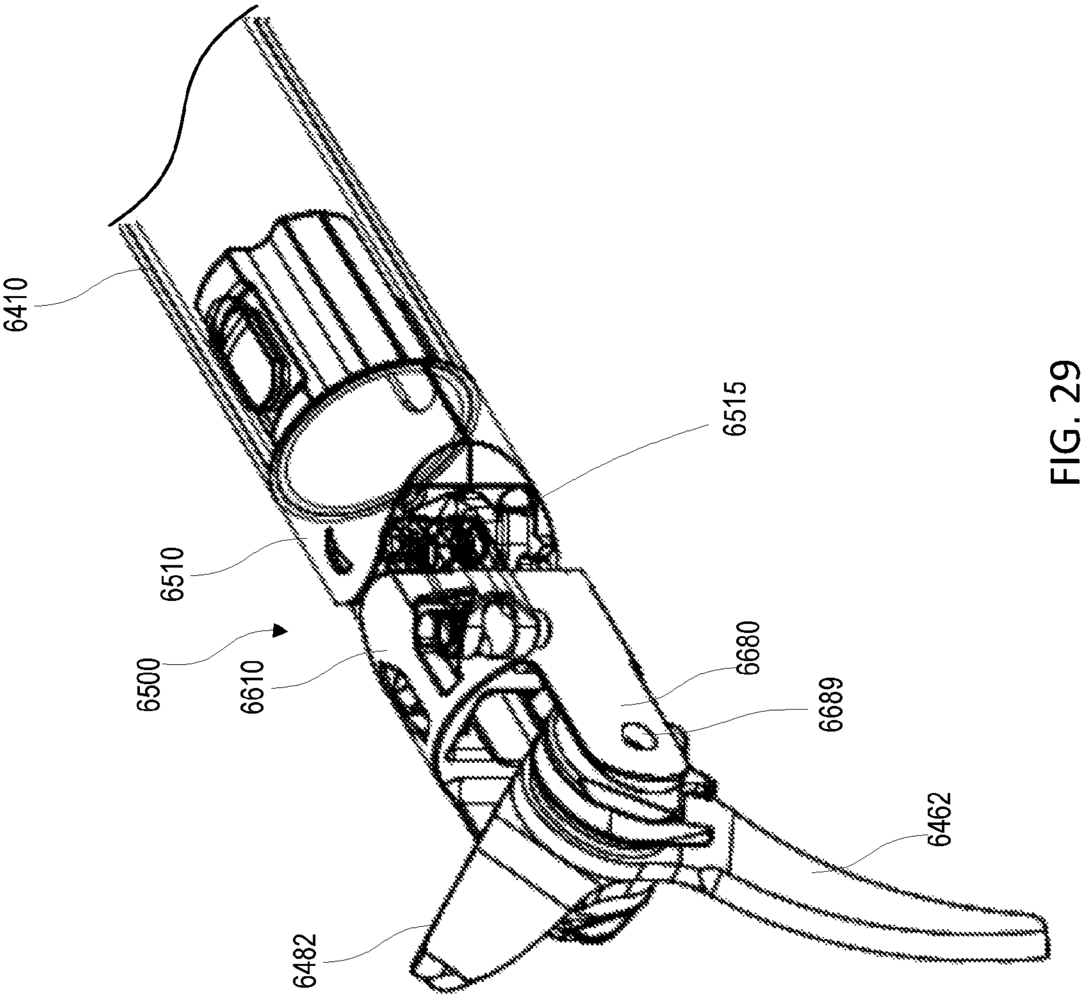
FIG. 29 is a perspective view of the distal end portion of the medical instrument of FIG. 21 with the outer cover removed with the end effector in an open position.
Figure 30:
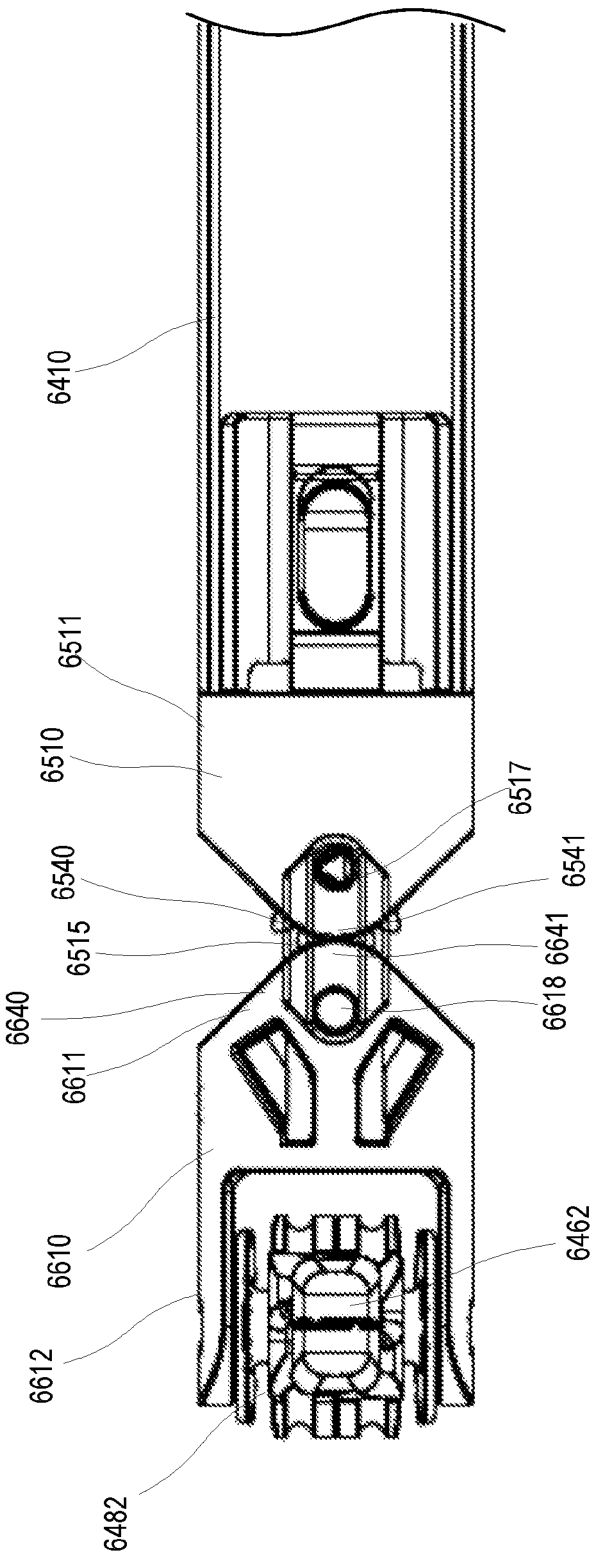
FIG. 30 is a top view of the distal end portion of the medical instrument of FIG. 21 with the outer cover removed and the end effector in the closed position and oriented pointing upwards (i.e., out of the page).
Figure 32:
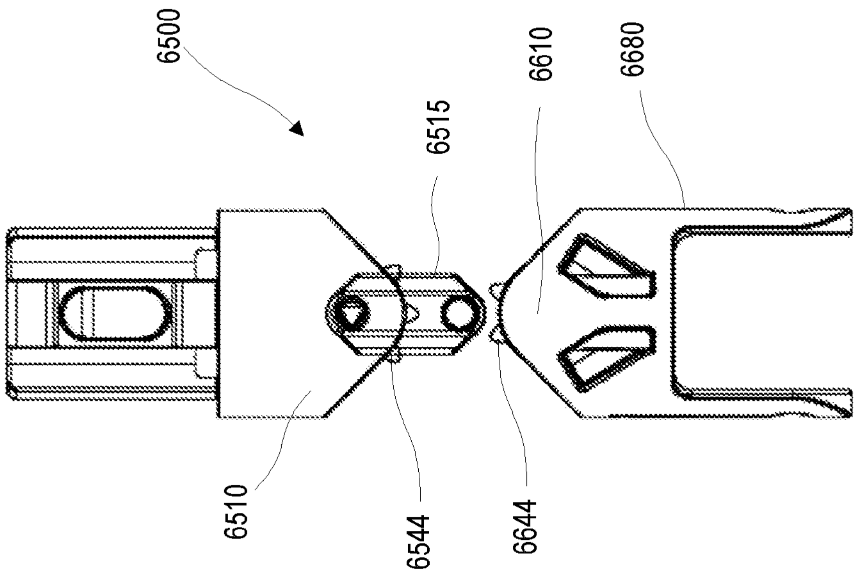
FIG. 32 is a partially exploded top view and FIGS. 33A and 33B are each a different partially exploded perspective view of the wrist assembly of the medical instrument of FIG. 21.
Figure 31:
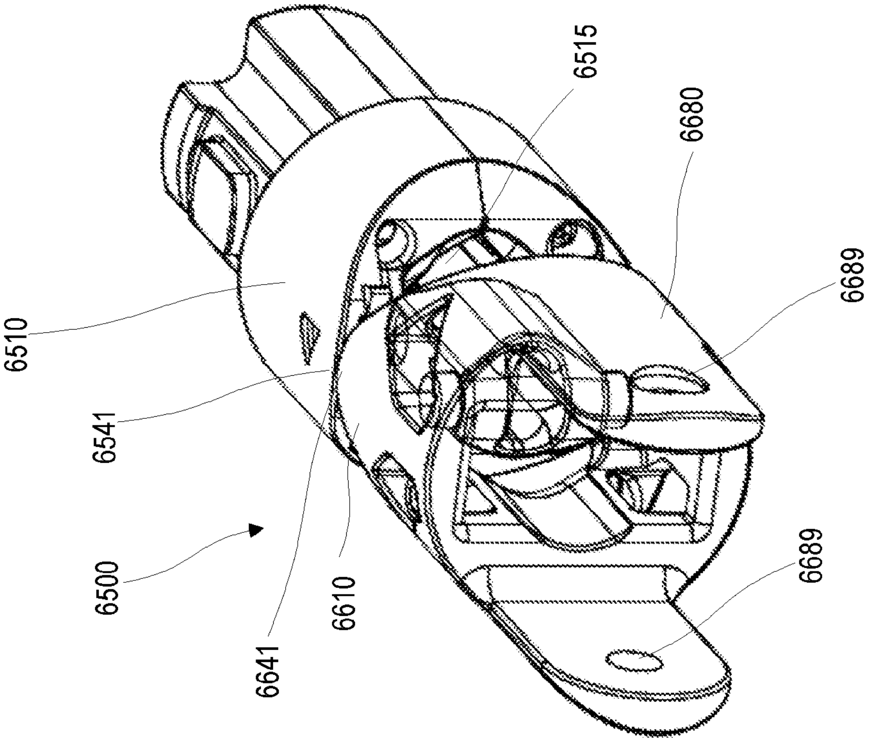
FIG. 31 is a perspective view of the wrist assembly of the medical instrument of FIG. 21.
Figure 33B:
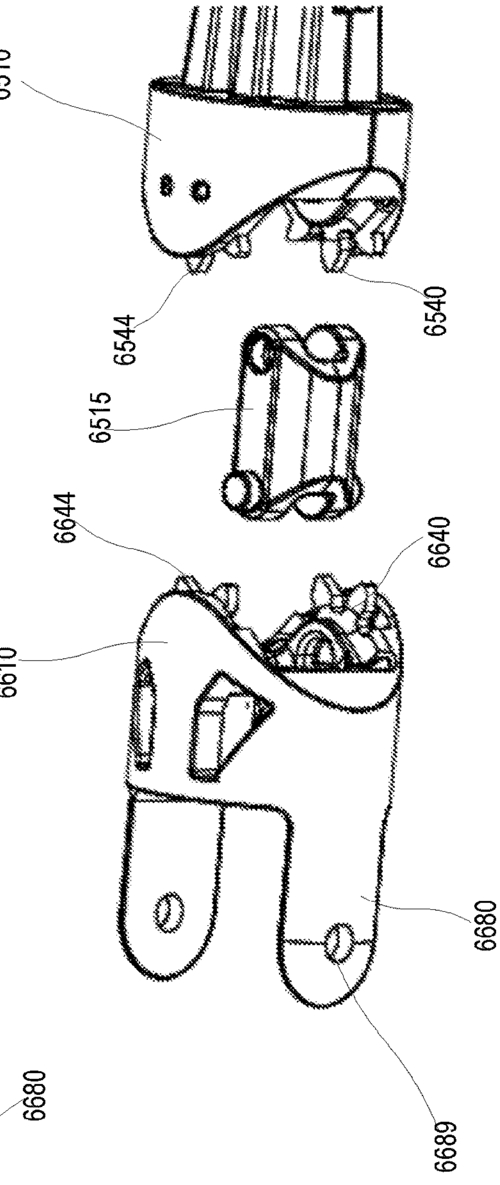
Figure 33A:
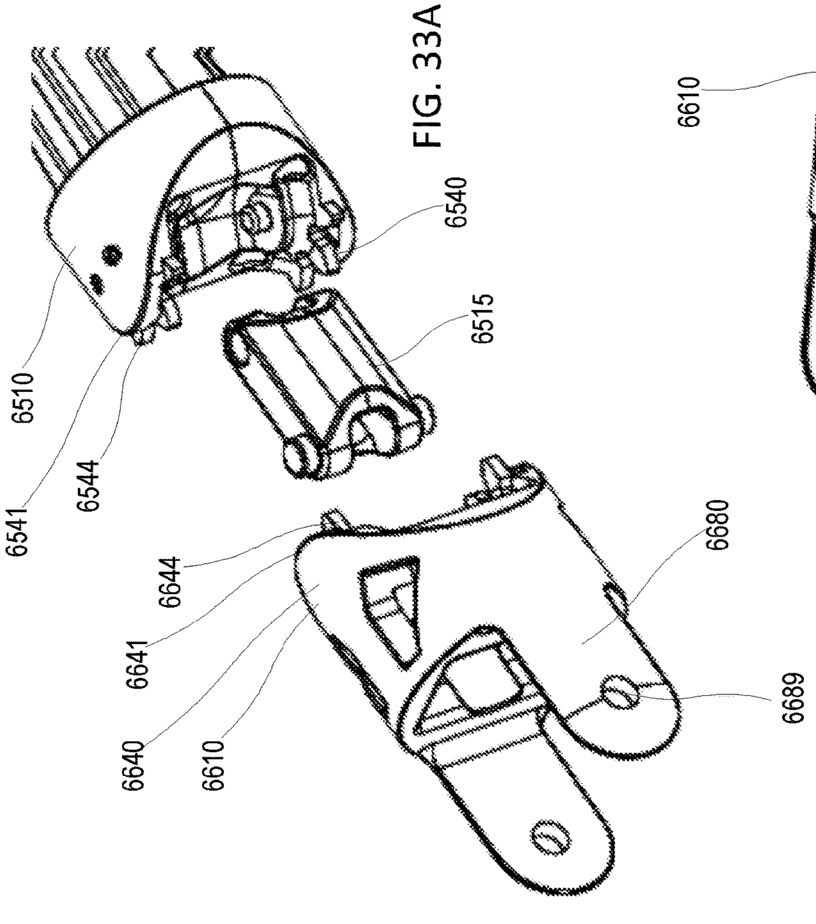

The distal end portion 6512 includes a joint portion 6540 that is rotatably coupled to a mating joint portion 6640 of the second link 6610 as described in more detail below. The second link 6610 has a proximal portion 6611 and a distal end portion 6612. The proximal portion 6611 includes a joint portion 6640 that is rotatably coupled to the joint portion 6540 of the first link 6510. to form the wrist assembly 6500 having a first axis of rotation $A_1$ about which the second link 6610 rotates relative to the first link as shown in FIGS. 27 and 28. The wrist assembly 6500 can include any suitable coupling mechanisms. In this embodiment, the first link 6510 is coupled to the third link 6515 via a pinned joint at 6517 and the second link 6610 is coupled to the third link 6515 via a pinned joint at 6618 (see, e.g., FIGS. 28 and 30). In this manner, the third link 6515 can assist in maintaining the coupling between the first link 6510 and the second link 6610 during rotation of the second link 6610 relative to the first link 6510.

Further, as described above, the distal end portion 6512 of the first link 6510 includes a joint portion 6540 that is rotatably coupled to a mating joint portion 6640 at the proximal end portion 6611 of the second link 6610. Specifically, the joint portion 6540 includes a series of teeth 6544 that are spaced apart by recesses and the joint portion 6640 includes a series of teeth 6644 that are spaced apart by recesses (see, e.g., FIGS. 33A and 33B). The series of teeth 6544 and 6644 and recesses can be similar to those shown and described in U.S. Patent Application Pub. No. US 2017/0120457 A1 (filed Feb. 20, 2015), entitled "Mechanical Wrist Joints with Enhanced Range of Motion, and Related Devices and Methods," or to those shown and described in International Application No. PCT/US18/64721 (filed Dec. 10, 2018), entitled "Medical Tools Having Tension Bands," each of which is incorporated herein by reference in its entirety. The teeth 6544 engage the teeth 6644 during rotation of the second link 6610 relative to the first link 6510. In addition, the joint portion 6540 has a curved surface 6541 that engages a curved surface 6641 of the joint portion 6640 during rotation of the second link 6610 relative to the first link 6510. Because the wrist joint (i.e., the joint between the first link 6510 and the second link 6610) is not a pinned joint, the pitch axis $A_1$ will move relative to the first link 6510 during rotation of the second link 6610. In other words, the location of the pitch axis $A_1$ will move (for example, as viewed in a top view) with the rolling movement of the second link 6610 relative to the first link 6510.

As shown in FIGS. 27-30, the end effector 6460 is coupled to the second link 6610. More specifically, the distal end portion 6612 of the second link 6610 includes a connector 6680 that is coupled to the end effector 6460 such that the end effector 6460 (e.g., tool members of the end effector described in more detail below) rotates relative to the wrist assembly 6500 about the second axis of rotation $A_2$ (see, e.g., FIGS. 27 and 28). The second axis of rotation $A_2$ is non-parallel to the first axis of rotation $A_1$. The axis $A_2$ functions both as a yaw axis (the term yaw is arbitrary), and also as a cutting axis as tool members rotate in opposition to each other as described in more detail below. Thus, the instrument 6400 provides at least three degrees of freedom (i.e., pitch motion about the first axis of rotation $A_1$, a yaw rotation about the second axis of rotation $A_2$, and a cutting motion about the second axis of rotation $A_2$). The connector 6680 can be any suitable connector to rotatably couple the end effector 6460 to the wrist assembly 6500. For example, in some embodiments, the first link 6510 can include a clevis and a pin, such as the pinned joints shown and described in U.S. Pat. No. 9,204,923 B2 (filed Jul. 16, 2008), entitled "Medical Instrument Electronically Energized Using Drive Cables," which is incorporated herein by reference in its entirety.

As shown in FIGS. 27-29 and 34-36B, the end effector 6460 includes a first tool member 6462 and a second tool member 6482. The first tool member 6462 includes a contact portion 6464, a drive pulley 6470 and a coupling spool 6467. The contact portion 6464 is configured to engage or manipulate a target tissue during a surgical procedure. For example, in this embodiment, the contact portion 6464 includes an engagement surface that functions as a cutter (e.g., a cutting blade). In other embodiments, the contact portion 6464 can function as a gripper, tissue manipulator, or the like, or can be an energized tool member that is used for cauterization or electrosurgical procedures. The second tool member 6482 includes a contact portion 6484, a drive pulley 6480 and a coupling spool 6487. The contact portion 6484 is configured to engage or manipulate a target tissue during a surgical procedure. For example, in this embodiment, the contact portion 6484 includes an engagement surface that functions as a cutter (e.g., a cutting blade). In other embodiments, the contact portion 6484 can function as a gripper, tissue manipulator, or the like, or can be an energized tool member that is used for cauterization or electrosurgical procedures. In this embodiment (as shown in FIG. 35A), the drive pulley 6470 and coupling spool 6467 can be formed as an integral or monolithic component that is welded (or otherwise coupled) to the engagement portion 6464, and the drive pulley 6480 and coupling spool 6487 can be formed as an integral or monolithic component that is welded (or otherwise coupled) to the engagement portion 6484. In some embodiments, the engagement portions 6464 and 6484 can each be formed as two parts—a stamped component and a ground spine with opposing cutting edges and the drive pulleys 6470, 6480 and coupling spools 6467, 6487 are formed with a metallic material and machined or formed through a metal injection molding process.

Figure 34:
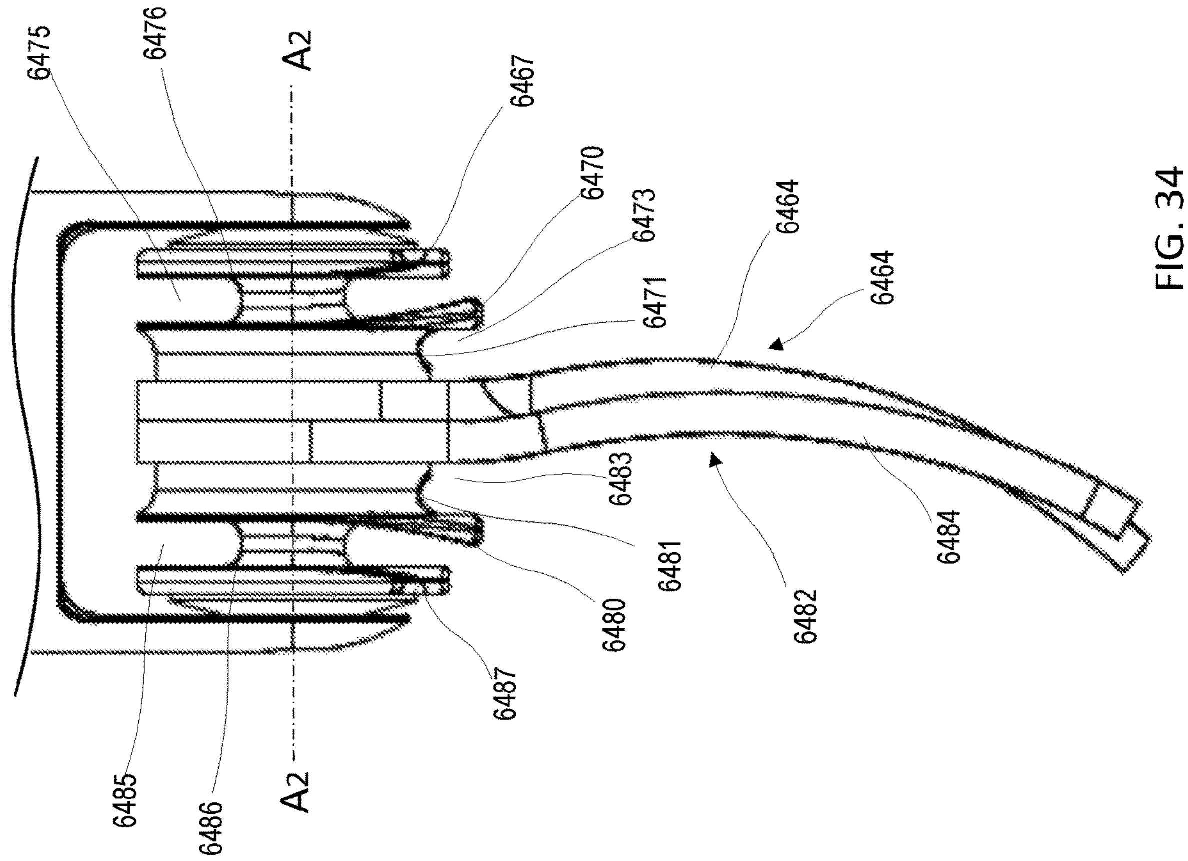
FIG. 34 is an enlarged top view of a portion of the end effector of the medical instrument of FIG. 21.

The drive pulley 6470 of the first tool member 6462 defines a guide channel 6473 with a drive surface 6471 and the coupling spool 6467 defines a spool channel 6475 with wrap surface 6476 as shown, for example, in FIGS. 34 and 36A. Similarly, the drive pulley 6480 of the second tool member 6482 defines a guide channel 6483 with a drive surface 6481 and the coupling spool 6487 defines a spool channel 6485 with a wrap surface 6486 (see, e.g., FIG. 34). The guide channel 6473 and spool channel 6475 are configured to receive a distal end portion of the first cable 6420, and the guide channel 6483 and spool channel 6485 are configured to receive a distal end portion of the second cable, as described in more detail below. As shown in FIGS. 28 and 34, for first tool member 6462, the drive pulley 6470 is disposed at a first location along the axis $A_2$ and the coupling spool 6467 is disposed at a second location along the axis $A_2$. In other words, the drive pulley 6470 and the coupling spool 6467 are disposed at a spaced distance from each other along the same rotational axis. The drive pulley 6480 and the coupling spool 6487 of tool member 6482 are similarly disposed.

Figure 35A:
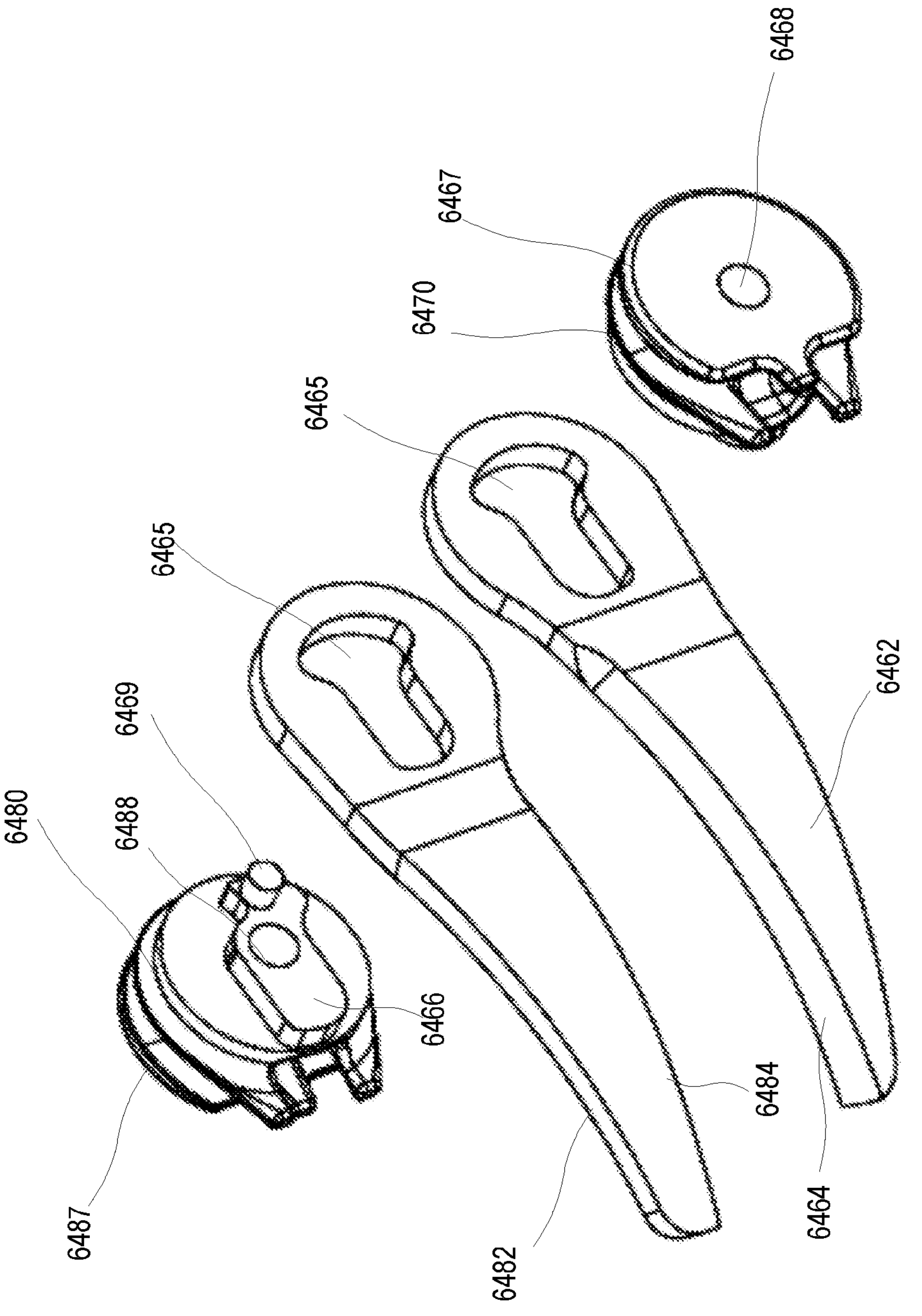
FIG. 35A is a partially exploded perspective view of the end effector of the medical instrument of FIG. 21.
Figure 35B:
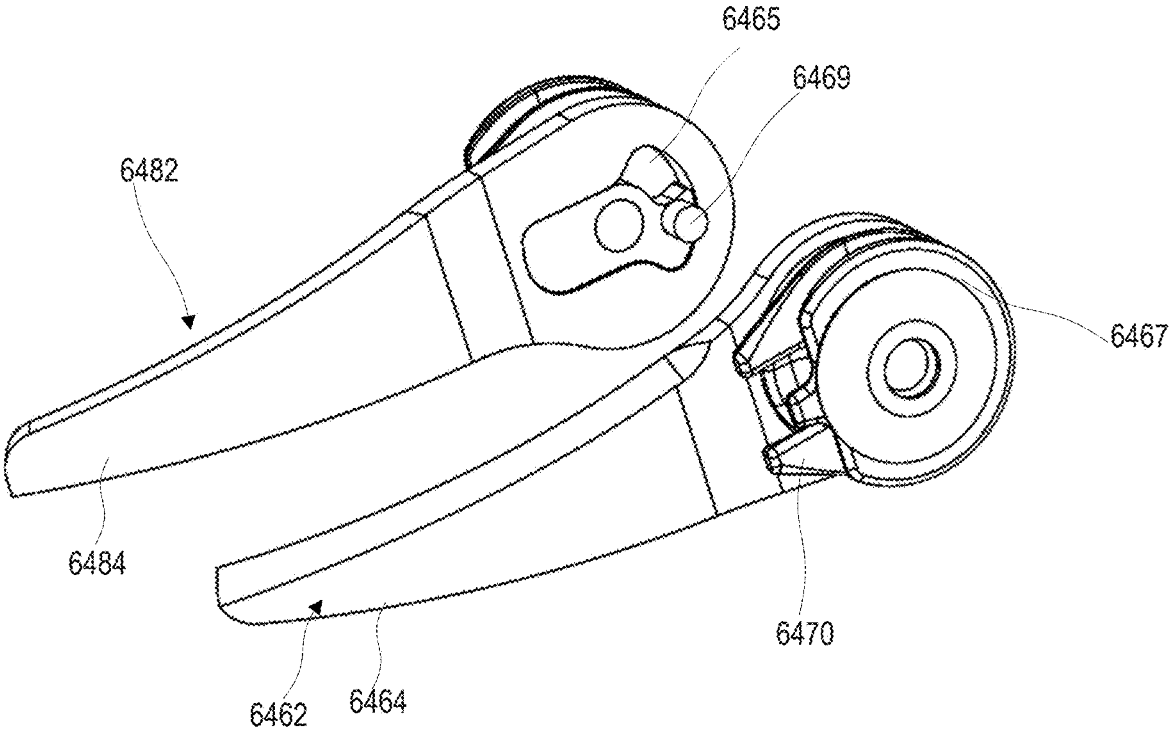
FIGS. 35B and 35C are each a partially exploded perspective view of the end effector of the medical instrument of FIG. 21, with FIG. 35C illustrating an opposite side of the end effector than FIG. 35B.
Figure 35C:
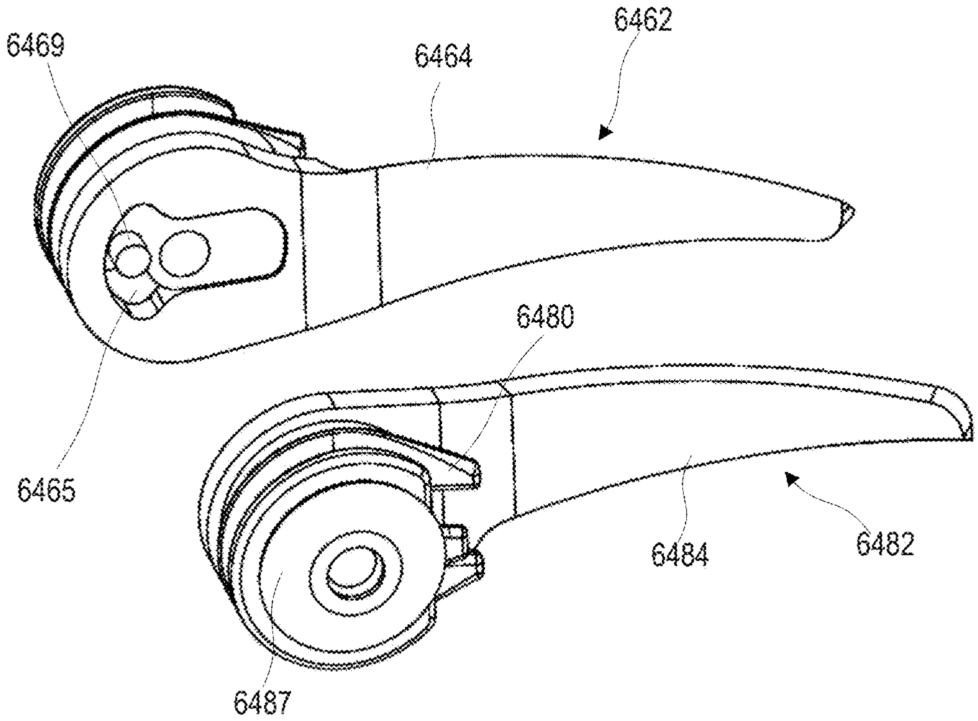
Figure 36B:
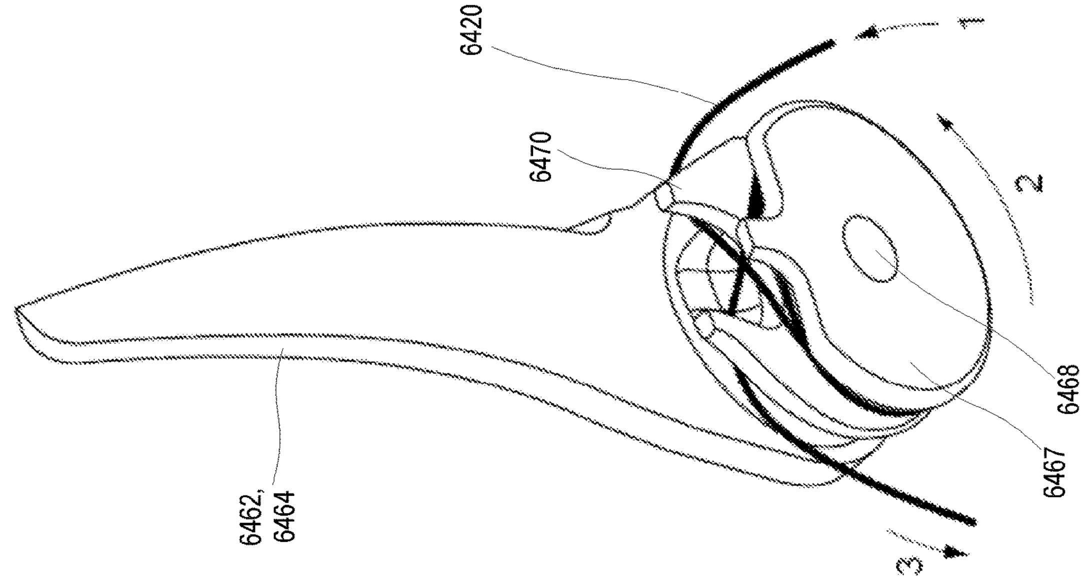
FIGS. 36A and 36B are a side view (FIG. 36A) and a perspective view (FIG. 36B) of a single tool member of the end effector of FIGS. 34 and 35A-35C.
Figure 36A:
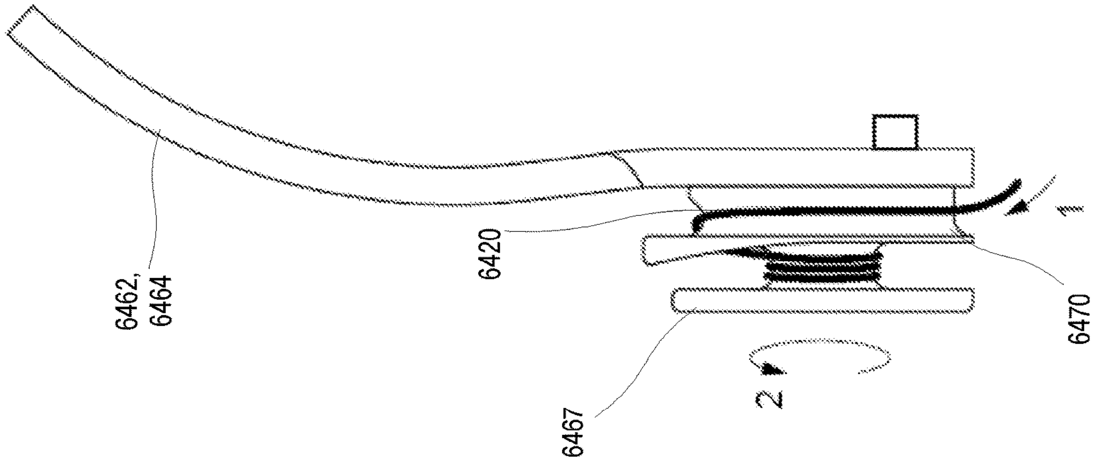

As shown in FIG. 35A, each of the first tool member 6462 and second tool member 6482 includes a guide slot 6465 formed with a particular shape that receives a guide block 6466 that is coupled to the respective drive pulleys 6470 and 6480. In this manner, the contact portion 6464 can be formed separately from and can be later attached to the drive pulley 6470 and the coupling spool 6467. Similarly, the contact portion 6484 can be formed separately from and can be later attached to the drive pulley 6490 and the coupling spool 6487. This arrangement allows the contact portion 6464 and the contact portion 6484 to have the same design, regardless of whether being used as the right (or "lower") tool member or the left (or "upper") tool member. Each tool member is formed by coupling the guide block 6466 within the respective guide slot 6465. As shown in FIGS. 35B and 35C, the guide block 6466 and the guide slot 6465 are shaped such that the contact portion 6464 is maintained in a fixed position with respect to the drive pulley 6470 and the coupling spool 6467 and the contact portion 6484 is maintained in a fixed position with respect to the drive pulley 6490 and the coupling spool 6487. The guide block 6466 includes a pin 6469 that is configured to travel along a path defined by the guide slot 6465 to limit the angle through which the first tool member 6462 rotates relative to the second tool member 6482. The tool members 6462 and 6482 are rotatably coupled to the second link 6610 via a respective pin (not shown), which is disposed within a central opening 6468 of the tool members 6462 and a central opening 6488 of tool member 6482, which are aligned with openings 6689 of the second link 6610.

The end effector 6460 can be operatively coupled to the mechanical structure 6700 such that the tool members 6462 and 6482 rotate about the axis of rotation $A_2$. For example, the drive surface 6471 of the drive pulley 6470 is configured to engage the first cable 6420 such that a tension force exerted by the first cable 6420 along the drive surface 6471 produces a rotation torque about the rotation axis $A_2$. Similarly, the drive surface 6481 of the drive pulley 6480 is configured to engage the second cable such that a tension force exerted by the second cable along the drive surface 6481 produces a rotation torque about the rotation axis A2. In this manner, the contact portion 6464 of the tool member 6462 and the contact portion 6484 of the tool member 6482 can be actuated to engage or manipulate a target tissue during a surgical procedure.

As described above, both the first cable 6420 and the second cable extend from the mechanical structure 6700 and are coupled to the end effector 6460. More specifically, the distal end portion of the first cable is coupled to the first tool member 6462 of the end effector 6460 and a distal end portion of the second cable is couple to the second tool member 6482 of the end effector 6460. FIGS. 36A and 36B illustrate the cable routing for the first cable 6420 on the first tool member 6462 and it should be understood that the second cable can be routed and coupled to the second tool member 6482 is the same manner.

As described above, the first cable 6420 can extend from the mechanical structure 6700, where a first proximal end portion of the first cable 6420 is coupled (as described above), extend along the shaft 6410 and is routed about a first portion of the drive surface 6471 of the drive pulley 6470, as shown by arrow 1 in FIGS. 36A and 36B. The first cable 6420 crosses over the drive pulley 6470 to start a wrap about the coupling spool 6467 as shown at arrow 2 in FIGS. 36A and 36B. In this embodiment, the cable 6420 is wrapped three revolutions about the wrap surface 6476 of the coupling spool 6467. In alternative embodiments, the cable

6420 is wrapped about the coupling spool 6467 less or more than three times. The cable 6420 is then crossed back over to the drive pulley 6470 (as best shown in FIG. 36B) where it is routed about a second portion of the drive surface 6471 before it exits the end effector 6460 and extends back to the mechanical structure 6700 as shown at arrow 3 in FIG. 36B. After exiting the end effector 6460, the second proximal end portion of the cable 6420 is then extended back along the shaft 6410, and is coupled to the second capstan 6720 in the same manner as the first proximal end portion of the cable 6420 is coupled to the first capstan 6710.

With the cable 6420 coupled to the mechanical structure 6700 and to the end effector 6460, rotational movement produced by the first capstan 6710 and the second capstan 6720 can cause movement at the first tool member 6462 and the second tool member 6482, respectively. Thus, as described previously, better control of the overall movement of the end effector 6460 (and tool members 6462 and 6482) can be achieved. For example, the first capstan 6710 can be operable to produce rotational movement about the axis $A_3$ (shown in FIG. 22A) and cause the first proximal end portion of the first cable 6420 to move in a first direction. The second capstan 6720 can similarly be operable to produce rotational movement about the axis $A_4$, parallel to the axis $A_5$ and cause the second proximal end portion of the cable 6420 to move in an opposite direction. Thus, the opposite movement of the first proximal end portion and the second proximal end portion of the cable 6420 causes the first tool member 6462 to rotate (via the cable 6420 connection) about the rotational axis $A_2$ (e.g., yaw movement). The movement of the first proximal end portion and the second proximal end portion of the cable 6420 in the same direction causes the first tool member 6462 to rotate about the rotation axis $A_1$ (e.g., pitch movement). Similar movements of the second tool member 6482 can be made by rotation of the third capstan 6730 and fourth capstan 6740, which are coupled to the second tool member 6482 via the second cable.

FIGS. 37-40 illustrate another embodiment of an end effector that can be used with or incorporated within any of the medical instruments described herein. The end effector 7460 is shown coupled to a wrist assembly 7500 and a shaft 7410. The wrist assembly 7500 and the shaft 7410 can be constructed the same as or similar to and function the same as or similar to the wrist assembly 6500 and shaft 6510. Thus, specific details regarding the wrist assembly 7500 and shaft 7410 are not described.

The end effector 7460 includes a first tool member 7462 and a second tool member 7482. The first tool member 7462 includes a contact portion 7464, a drive pulley 7470 and a coupling spool 7467. The contact portion 7464 is configured to engage or manipulate a target tissue during a surgical procedure. For example, in this embodiment, the contact portion 7464 includes an engagement surface that functions as a gripper. In other embodiments, the contact portion 7464 can function as a cutter, tissue manipulator, or the like, or can be an energized tool member that is used for cauterization or electrosurgical procedures. The second tool member 7482 includes a contact portion 7484, a drive pulley 7480 and a coupling spool 7487. The contact portion 7484 is configured to engage or manipulate a target tissue during a surgical procedure. For example, in this embodiment, the contact portion 7484 includes an engagement surface that functions as a gripper. In other embodiments, the contact portion 7484 can function as a cutter, tissue manipulator, or the like, or can be an energized tool member that is used for cauterization or electrosurgical procedures. In this embodiment, the drive pulley 7470 and coupling spool 7467 can be formed as an integral or monolithic component with the engagement portion 7464, and the drive pulley 7480 and coupling spool 7487 can be formed as an integral or monolithic component that is welded (or otherwise coupled) to the engagement portion 7484. In other embodiments, the engagement portions 7464 and 7484 can each be formed as separate parts—a stamped component, and the drive pulleys 7470, 7480 and second portions 7467, 7487 are formed with a metallic material and machined or formed through a metal injection molding process.

Figure 39B:
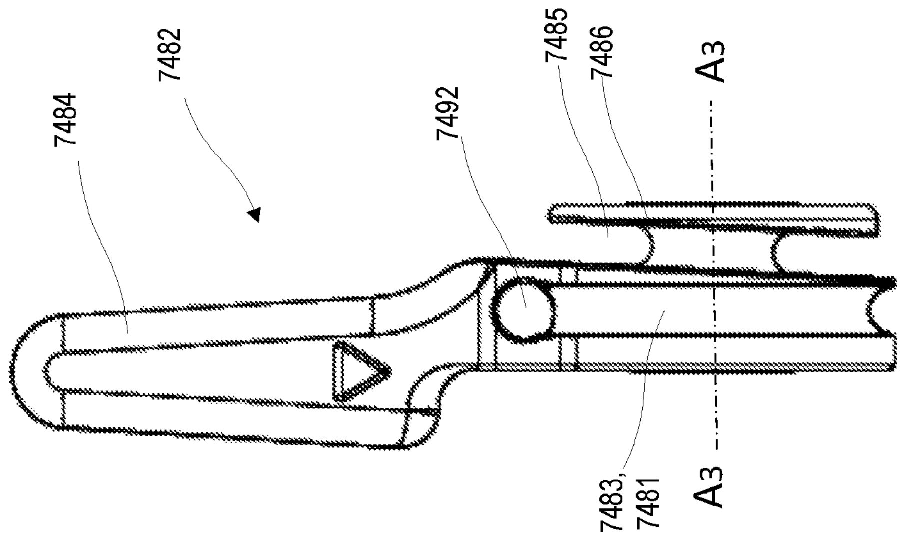
FIGS. 39A and 39B are each a side view of a different tool member of the end effector of FIG. 38A.
Figure 39A:
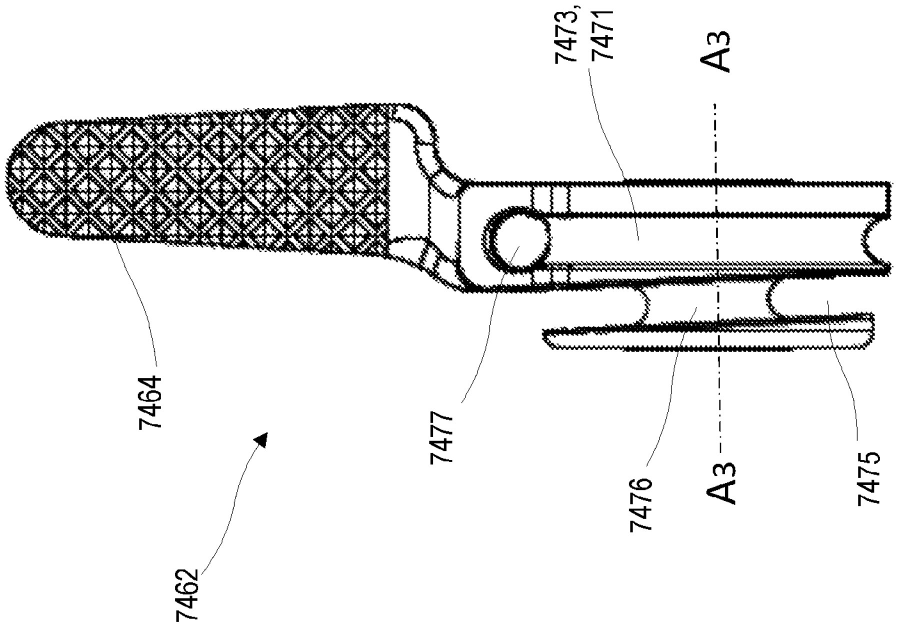
Figure 40:
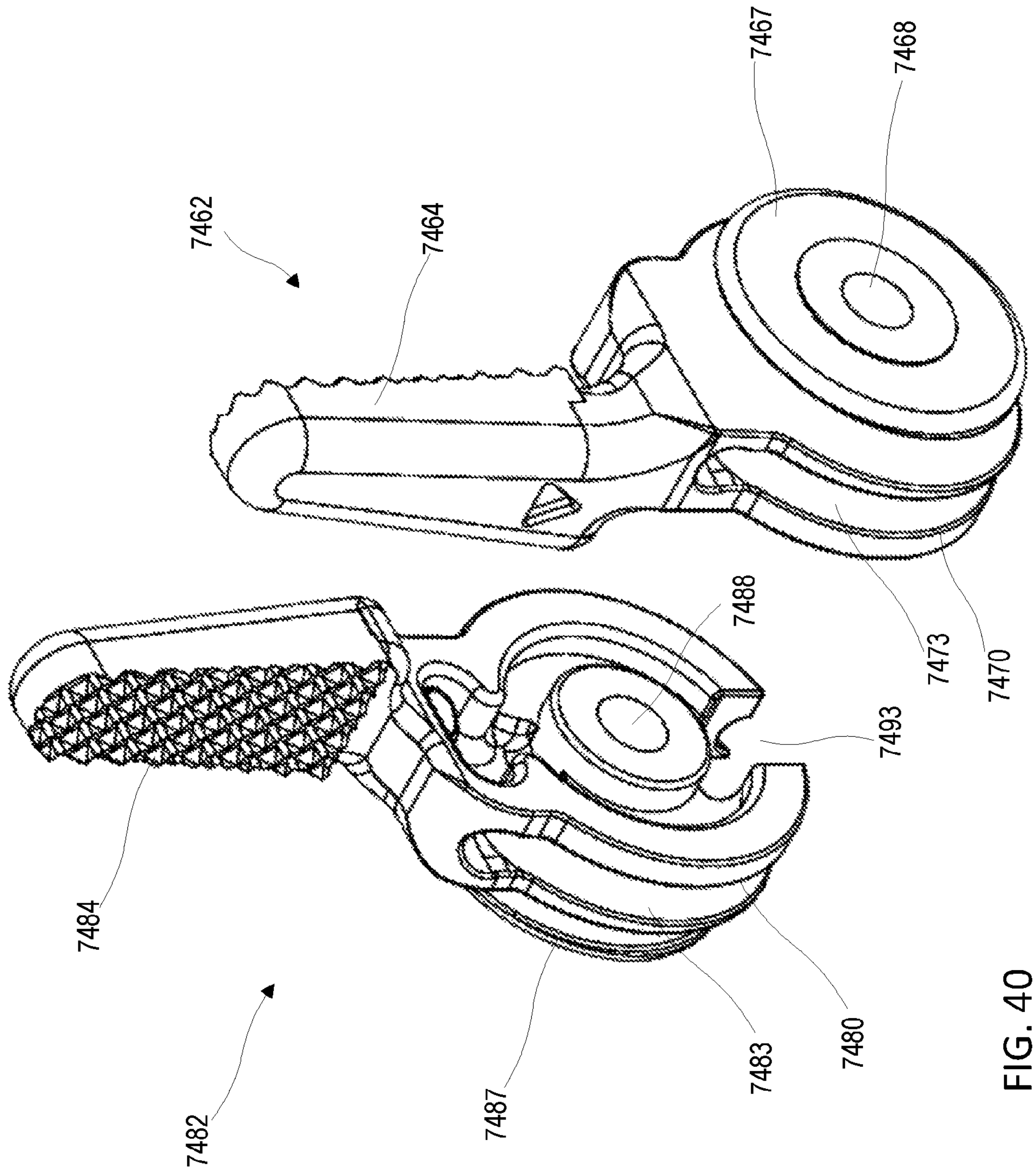
FIG. 40 is a partial exploded view of the end effector of FIG. 38A.

As shown, for example, in FIGS. 39A and 39B, the drive pulley 7470 of the first tool member 7462 defines a guide channel 7473 with a drive surface 7471 and the coupling spool 7467 defines a spool channel 7475 with wrap surface 7476. Similarly, the drive pulley 7480 of the second tool member 7482 defines a guide channel 7483 with a drive surface 7481 and the coupling spool 7487 defines a spool channel 7485 with a wrap surface 7486. The guide channel 7473 and spool channel 7475 are configured to receive a distal end portion of a first cable (not shown), and the guide channel 7483 and spool channel 7485 are configured to receive a distal end portion of a second cable (now shown). As shown in FIGS. 39A and 39B, the drive pulley 7470 is disposed at a first location along an axis $A_2$ and the coupling spool 7467 is disposed at a second location along the axis $A_2$. In other words, the drive pulley 7470 and the coupling spool 7467 are disposed at a spaced distance from each other along the same rotational axis. The drive pulley 7480 and the coupling spool 7467 of tool member 7482 are similarly disposed at a first and second location, respectively, along the same rotational axis (i.e., axis $A_2$).

Figure 37:
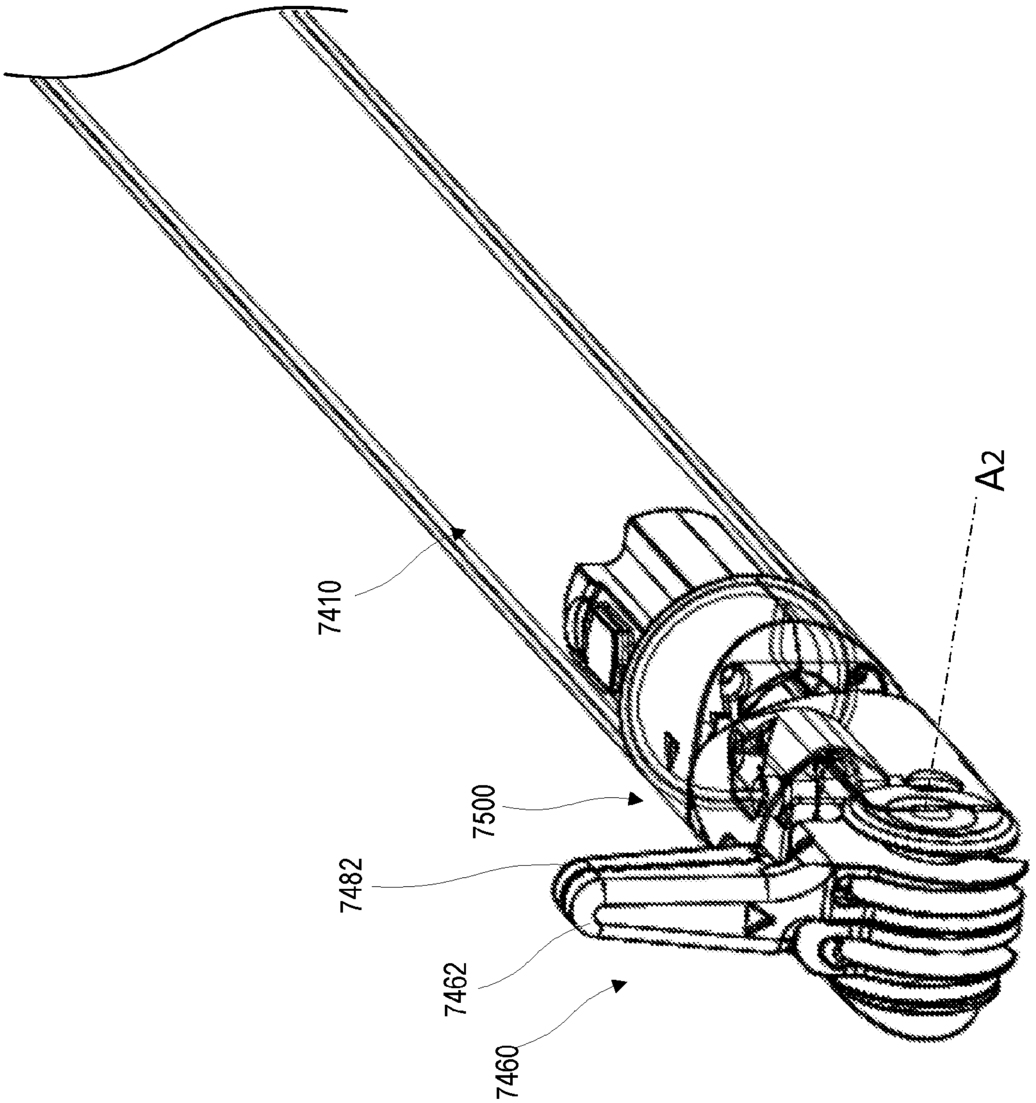
FIG. 37 is a perspective view of a portion of a medical instrument according to an embodiment.
Figure 38A:
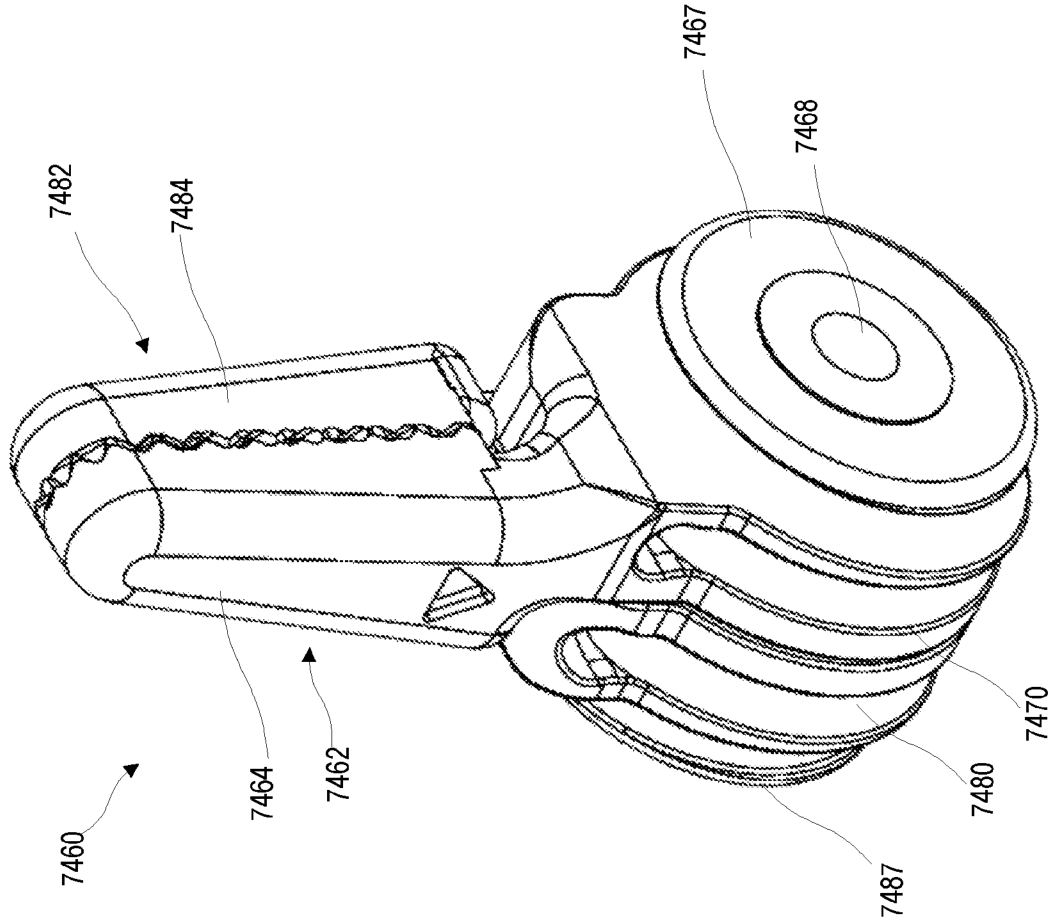
FIG. 38A is a perspective view of an end effector of the medical instrument of FIG. 37.
Figure 38B:
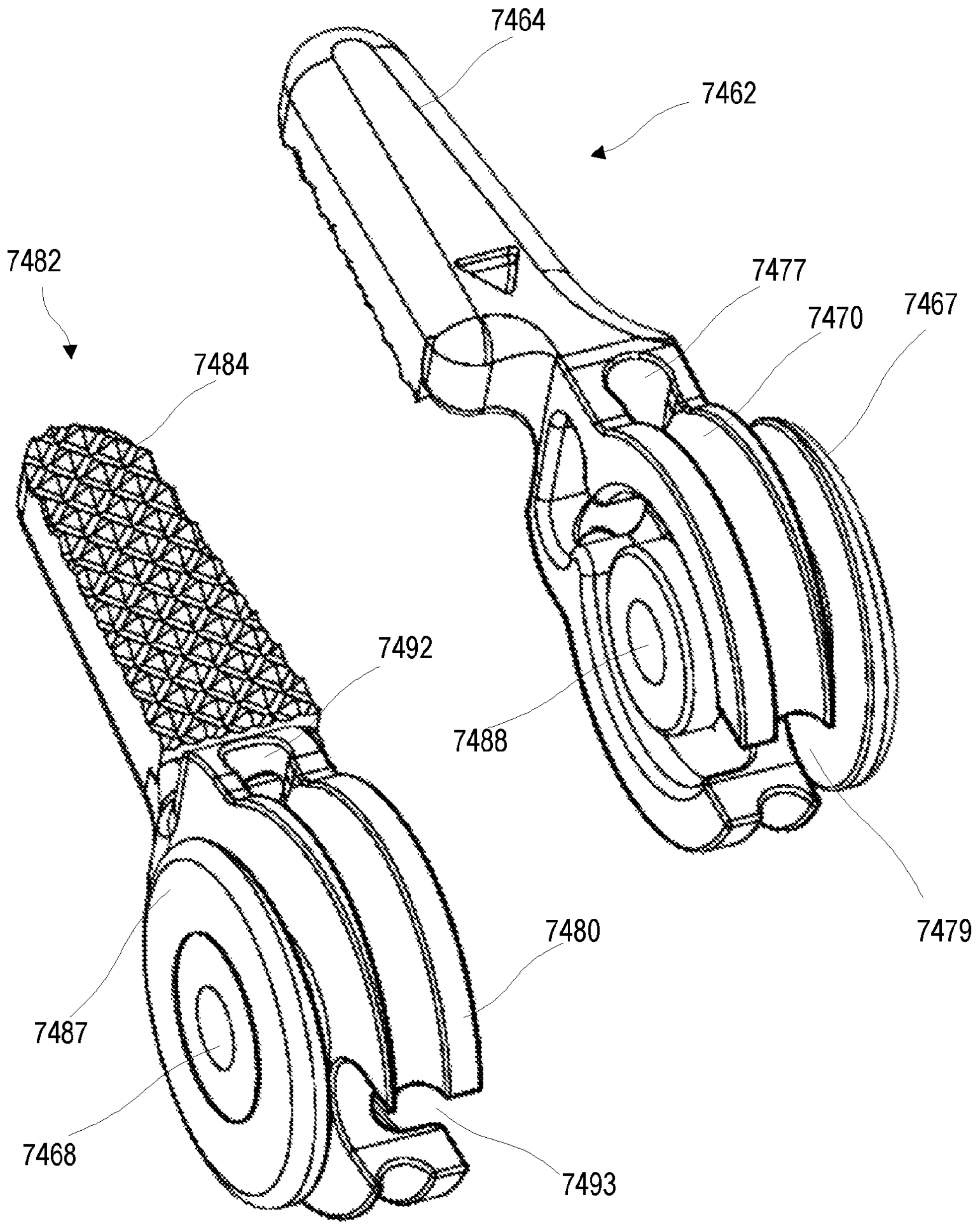
FIG. 38B is a partial exploded view of the end effector of FIG. 38A.

As shown in FIG. 37, the tool members 7462, 7482 are rotatably coupled to the second link 7610 of the wrist assembly 7500 via a respective pin (not shown), which is disposed within a central opening 7468 of the tool member 7462 and a central opening 7488 of the tool member 7482, which are aligned with openings 7689 (see FIG. 37) of wrist assembly 7500.

The end effector 7460 can be operatively coupled to a mechanical structure in the same or similar manner as described for previous embodiments, such that the tool members 7462 and 7482 rotate about the axis of rotation $A_2$. For example, the drive surface 7471 of the drive pulley 7470 is configured to engage the first cable (not shown) such that a tension force exerted by the first cable along the drive surface 7471 produces a rotation torque about the rotation axis $A_2$. Similarly, the drive surface 7481 of the drive pulley 7480 is configured to engage the second cable (not shown) such that a tension force exerted by the second cable along the drive surface 7481 produces a rotation torque about the rotation axis $A_2$. In this manner, the contact portion 7464 of the tool member 7462 and the contact portion 7484 of the tool member 7482 can be actuated to engage or manipulate a target tissue during a surgical procedure.

As described above for previous embodiments, both the first cable (not shown) and the second cable (not shown) can extend from a mechanical structure (as described herein) and are coupled to the end effector 7460. More specifically, a distal end portion of the first cable is coupled to the first tool member 7462 of the end effector 7460 and a distal end portion of the second cable is coupled to the second tool member 7482 of the end effector 7460.

As described above for end effector 6460 and cable 6420, the first cable can extend from a mechanical structure, where a first proximal end portion of the first cable is coupled thereto (as described above), extends along the shaft 7410 and is routed about a first portion of the drive surface 7471 within the guide channel 7473 of the drive pulley 7470. In this embodiment, the first cable is passed through an opening 7477 and wrapped partially around the drive pulley 7470, then passes through a passageway 7479 (see FIG. 38B) which is in communication with the spool channel 7475 of the coupling spool 7467. The cable is then wrapped about the wrap surface 7476 of the coupling spool 7467 within the spool channel 7475 at least one revolution. The cable then passes back through opening 7479 and into the guide channel 7473 of the drive pulley 7470, and then out through an opposite end of the opening 7477 and extends along the shaft 7410 and back to the mechanical structure. The second tool member 7482 can similarly include an opening 7492 (see FIG. 39B) and passageway 7493 (see FIG. 40) and the second cable (not shown) can be coupled to the second tool member 7482 in the same manner.

Figure 41:
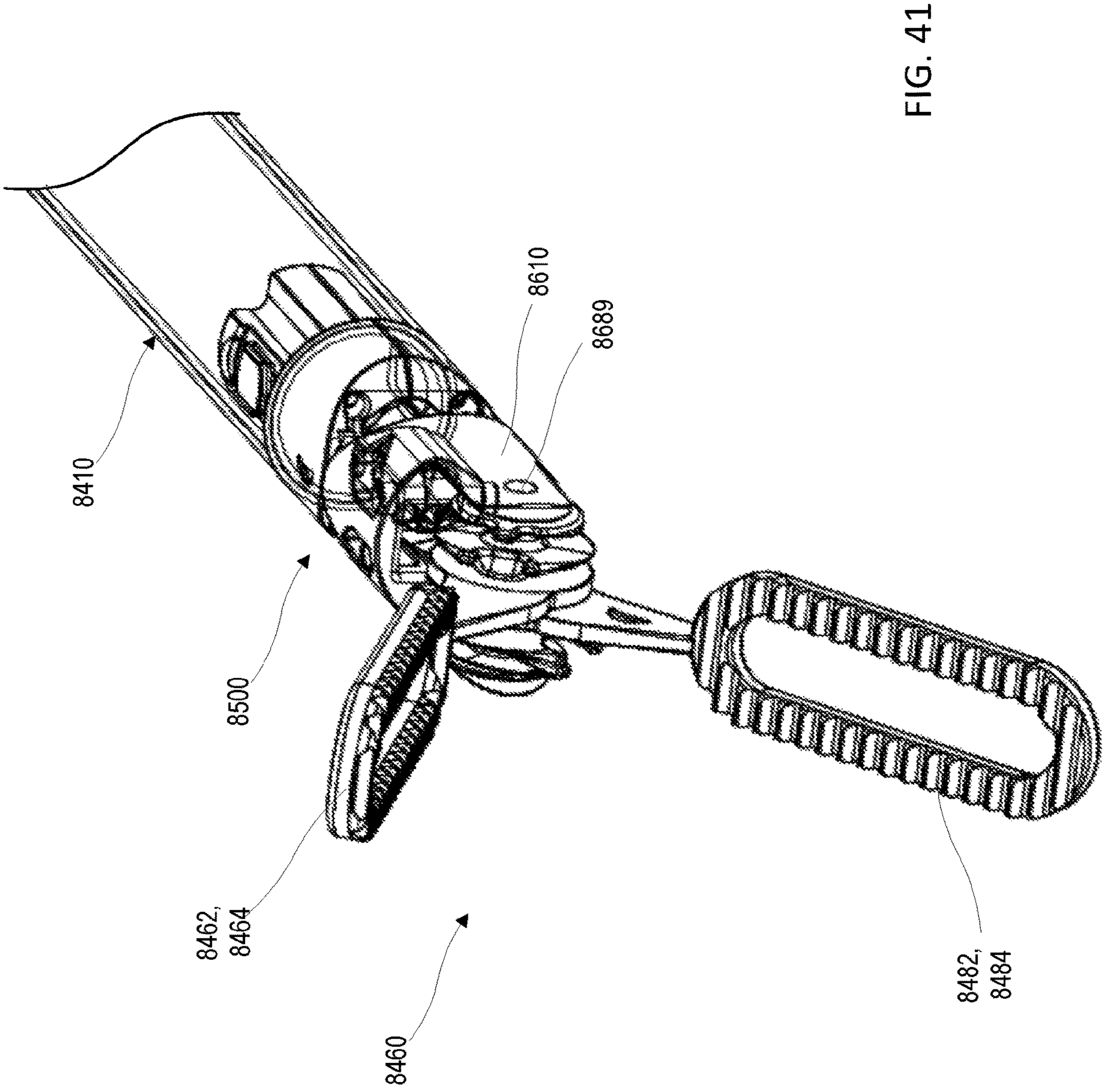
FIG. 41 is a perspective view of a portion of a medical instrument according to an embodiment.
Figure 43:
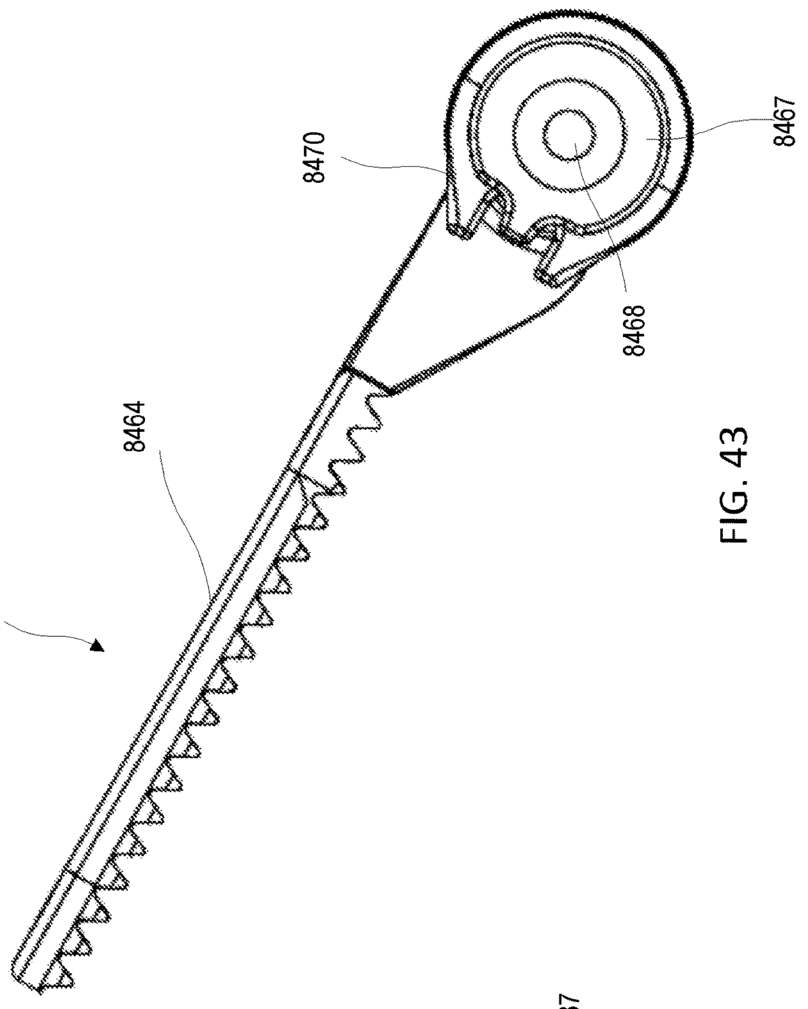
FIG. 43 is a side view of a tool member of the end effector of FIG. 42.
Figure 42:
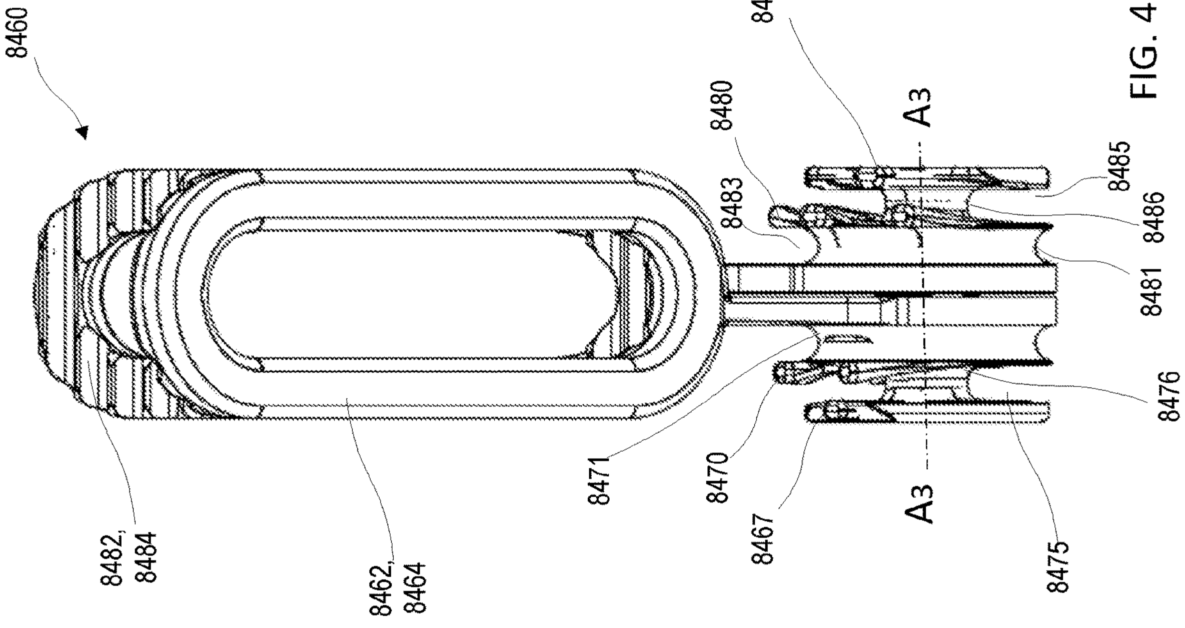
FIG. 42 is a side view of the end effector of the medical instrument of FIG. 41.
Figure 44:
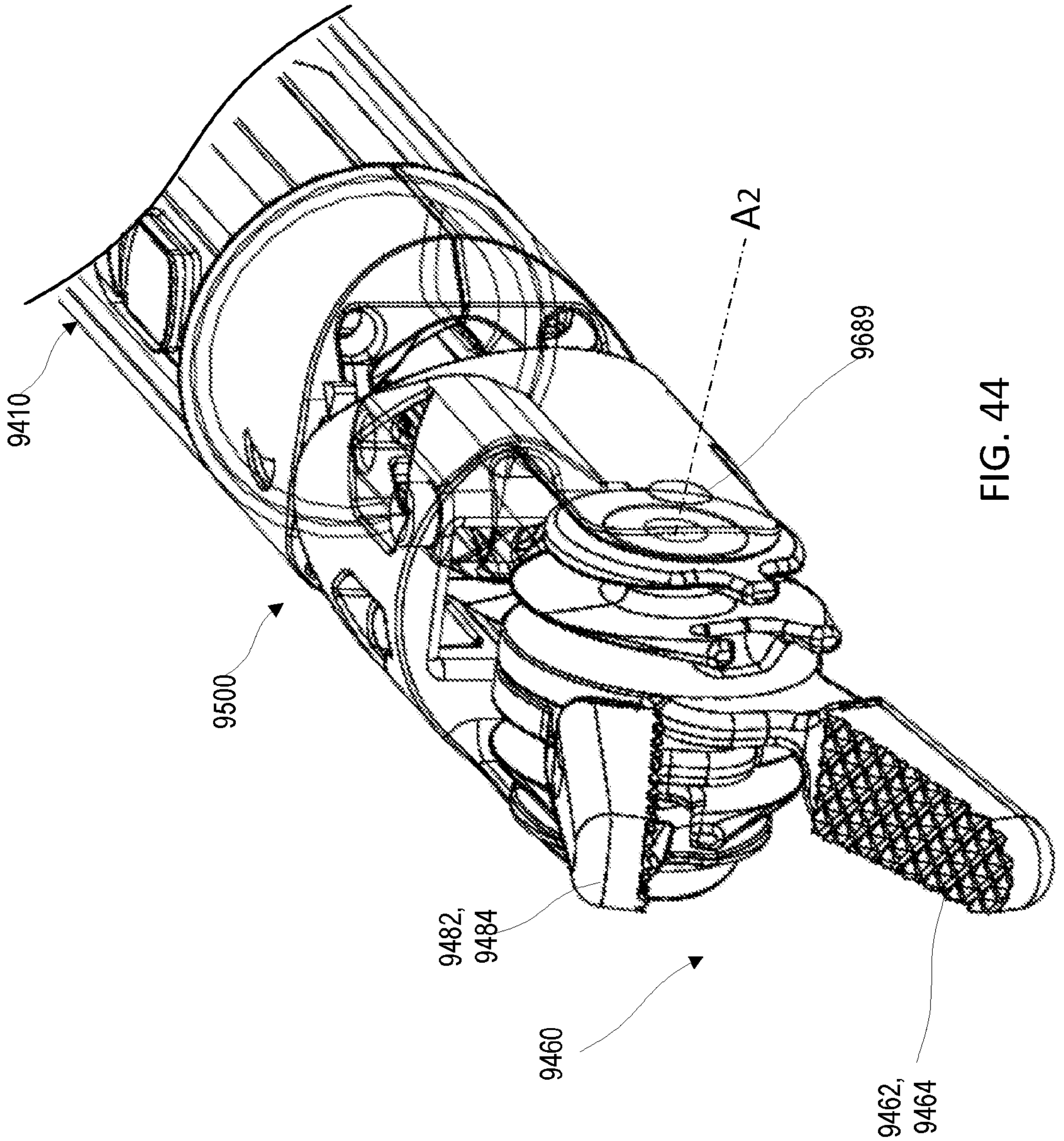
FIG. 44 is perspective view of a portion of a medical instrument according to an embodiment.

FIGS. 41-43 illustrate another embodiment of an end effector that can be used with or incorporated within any of the medical instruments described herein. The end effector 8460 is shown coupled to a wrist assembly 8500 and a shaft 8410. The wrist assembly 8500 and the shaft 8410 can be constructed the same as or similar to and function the same as or similar to the wrist assembly 6500 and shaft 6510. Thus, specific details regarding the wrist assembly 8500 and shaft 8410 are not described.

The end effector 8460 includes a first tool member 8462 and a second tool member 8482. The first tool member 8462 includes a contact portion 8464, a drive pulley 8470 and a coupling spool 8467. The contact portion 8464 is configured to engage or manipulate a target tissue during a surgical procedure. For example, in this embodiment, the contact portion 8464 includes an engagement surface that functions as a gripper. In other embodiments, the contact portion 8464 can function as a cutter, tissue manipulator, or the like, or can be an energized tool member that is used for cauterization or electrosurgical procedures. The second tool member 8482 includes a contact portion 8484, a drive pulley 8480 and a coupling spool 8487. The contact portion 8484 is configured to engage or manipulate a target tissue during a surgical procedure. For example, in this embodiment, the contact portion 8484 includes an engagement surface that functions as a gripper. In other embodiments, the contact portion 8484 can function as a cutter, tissue manipulator, or the like, or can be an energized tool member that is used for cauterization or electrosurgical procedures. In this embodiment, the drive pulley 8470 and coupling spool 8467 can be formed as an integral or monolithic component that is welded (or otherwise coupled) to the engagement portion 8464, and the drive pulley 8480 and coupling spool 8487 can be formed as an integral or monolithic component with the engagement portion 8484. In other embodiments, the engagement portions 8464 and 8484 can each be formed separately—a stamped component, and the drive pulleys 8470, 8480 and second portions 8467, 8487 are formed with a metallic material and machined or formed through a metal injection molding process.

As shown in FIG. 42, the drive pulley 8470 of the first tool member 8462 defines a guide channel 8473 with a drive surface 8471 and the coupling spool 8467 defines a spool channel 8475 with wrap surface 8476. Similarly, the drive pulley 8480 of the second tool member 8482 defines a guide channel 8483 with a drive surface 8481 and the coupling spool 8487 defines a spool channel 8485 with a wrap surface 8486. As with previous embodiments, the guide channel 8473 and spool channel 8467 are configured to receive a distal end portion of a first cable (not shown), and the guide channel 8481 and spool channel 8485 are configured to receive a distal end portion of a second cable (now shown). As shown in FIG. 42, the drive pulley 8470 is disposed at a first location along an axis $A_2$ and the coupling spool 8467 is disposed at a second location along the axis $A_2$. In other words, the drive pulley 8470 and the coupling spool 8467 are disposed at a spaced distance from each other along the same rotational axis. The drive pulley 8480 and the coupling spool 8467 of tool member 7482 are similarly disposed at a first and second location, respectively, along the same rotational axis (i.e., axis $A_2$).

The tool members 8462, 8482 are rotatably coupled to the second link 8610 of the wrist assembly 8500 via a respective pin (not shown), which is disposed within a central opening 8468 of the tool member 8462 and a central opening (not shown) of the tool member 8482, which are aligned with openings 8689 of wrist assembly 7500.

The end effector 8460 can be operatively coupled to a mechanical structure in the same or similar manner as described for previous embodiments, such that the tool members 8462 and 8482 rotate about the axis of rotation $A_2$. For example, the drive surface 8471 of the drive pulley 8470 is configured to engage the first cable (not shown) such that a tension force exerted by the first cable along the drive surface 8471 produces a rotation torque about the rotation axis $A_2$. Similarly, the drive surface 8481 of the drive pulley 8480 is configured to engage the second cable (not shown) such that a tension force exerted by the second cable along the drive surface 8481 produces a rotation torque about the rotation axis $A_2$. In this manner, the contact portion 8464 of the tool member 8462 and the contact portion 8484 of the tool member 8482 can be actuated to engage or manipulate a target tissue during a surgical procedure.

As described above for previous embodiments, both the first cable (not shown) and the second cable (not shown) can extend from a mechanical structure (as described herein) and are coupled to the end effector 8460. More specifically, a distal end portion of the first cable is coupled to the first tool member 8462 of the end effector 8460 and a distal end portion of the second cable is couple to the second tool member 8482 of the end effector 8460 in the same manner as described above for tool members 6462 and 6482.

FIGS. 44-48 illustrate another embodiment of an end effector that can be used with or incorporated within any of the medical instruments described herein. The end effector 9460 is shown coupled to a wrist assembly 9500 and a shaft 9410. The wrist assembly 9500 and the shaft 9410 can be constructed the same as or similar to and function the same as or similar to the wrist assembly 6500 and shaft 6510. Thus, specific details regarding the wrist assembly 9500 and shaft 9410 are not described.

The end effector 9460 includes a first tool member 9462 and a second tool member 9482. The first tool member 9462 includes a contact portion 9464, a drive pulley 9470 and a coupling spool 9467. The contact portion 9464 is configured to engage or manipulate a target tissue during a surgical procedure. For example, in this embodiment, the contact portion 9464 includes an engagement surface that functions as a gripper. In other embodiments, the contact portion 9464 can function as a cutter, tissue manipulator, or the like, or can be an energized tool member that is used for cauterization or electrosurgical procedures. The second tool member 9482 includes a contact portion 9484, a drive pulley 9480 and a coupling spool 9487. The contact portion 9484 is configured to engage or manipulate a target tissue during a surgical procedure. For example, in this embodiment, the contact portion 9484 includes an engagement surface that functions as a gripper. In other embodiments, the contact portion 9484 can function as a cutter, tissue manipulator, or the like, or can be an energized tool member that is used for cauterization or electrosurgical procedures. In this embodiment, the drive pulley 9470 and coupling spool 9467 can be formed as an integral or monolithic component that is welded (or otherwise coupled) to the contact portion 9464, and the drive pulley 9480 and coupling spool 9487 can be formed as an integral or monolithic component that is welded (or otherwise coupled) to the contact portion 9484. In some embodiments, the contact portions 9464 and 9484 can each be formed as two parts—a stamped component, and the drive pulleys 9470, 9480 and coupling spools 9467, 9487 are formed with a metallic material and machined or formed through a metal injection molding process.

Figure 46:
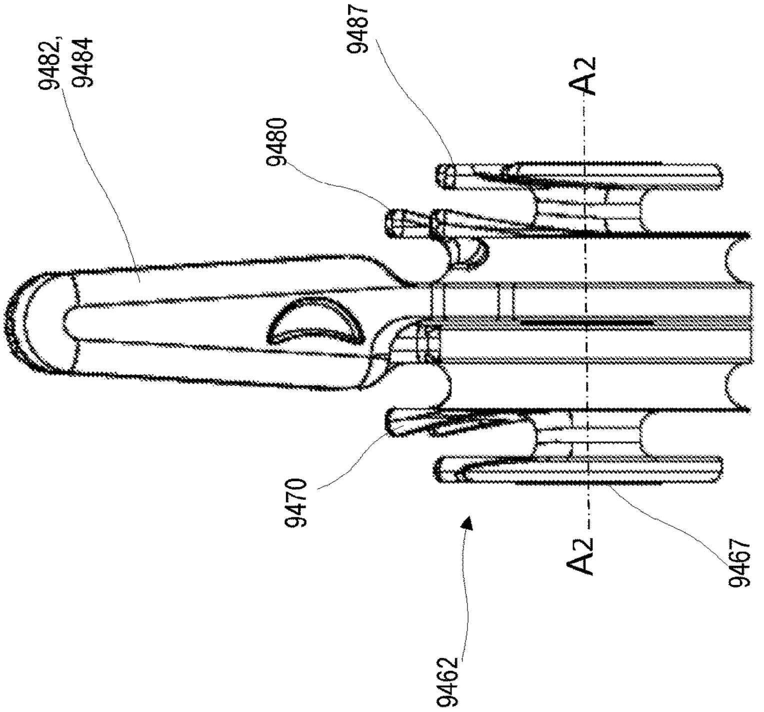
FIGS. 45 and 46 are a perspective view (FIG. 45) and a side view (FIG. 46) of the end effector of the medical instrument of FIG. 44.
Figure 45:
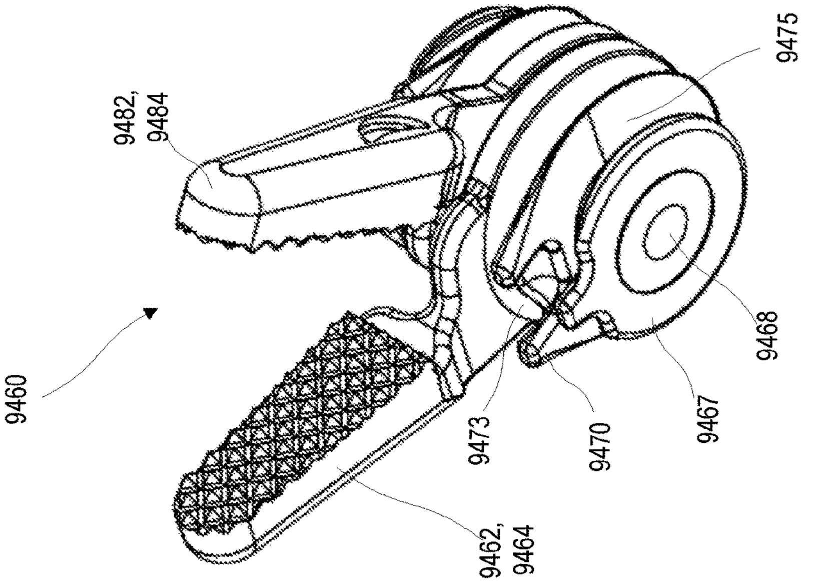
Figure 48:
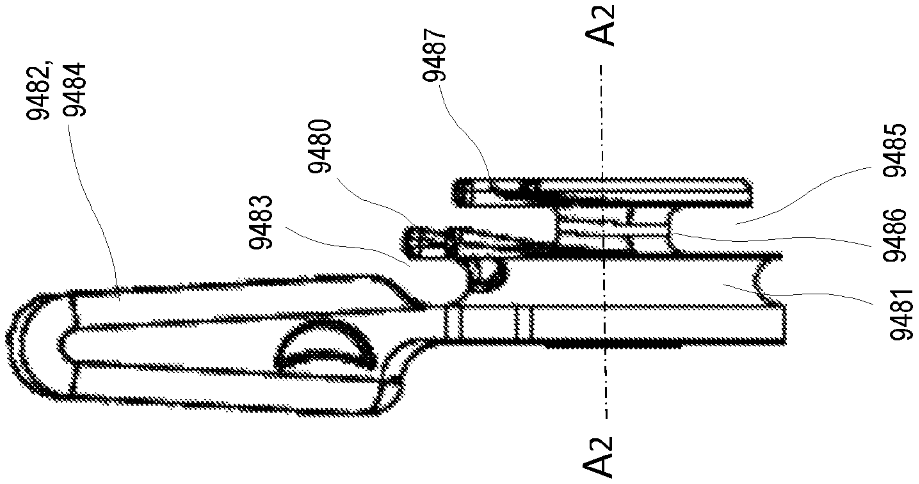
FIGS. 47 and 48 each a side view of a different tool member of the end effector of FIGS. 45 and 46.
Figure 47:
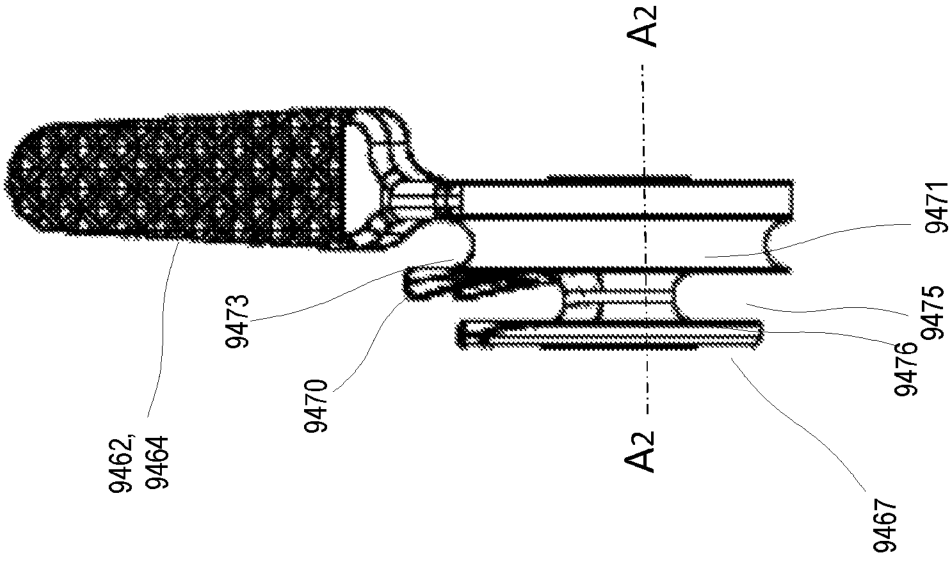

As best shown in FIGS. 47-48, the drive pulley 9470 of the first tool member 9462 defines a guide channel 9473 with a drive surface 9471 and the coupling spool 9467 defines a spool channel 9475 with wrap surface 9476. Similarly, the drive pulley 9480 of the second tool member 9482 defines a guide channel 9483 with a drive surface 9481 and the coupling spool 9487 defines a spool channel 9485 with a wrap surface 9486. As with previous embodiments, the guide channel 9473 and spool channel 9467 are configured to receive a distal end portion of a first cable (not shown), and the guide channel 9481 and spool channel 9485 are configured to receive a distal end portion of a second cable (now shown). As shown in FIGS. 46 and 47, the drive pulley 9470 is disposed at a first location along an axis $A_2$ and the coupling spool 9467 is disposed at a second location along the axis $A_2$. In other words, the drive pulley 9470 and the coupling spool 9467 are disposed at a spaced distance from each other along the same rotational axis. The drive pulley 9480 and the coupling spool 9467 of tool member 9482 are similarly disposed at a first and second location, respectively, along the same rotational axis (i.e., axis $A_2$) as shown in FIGS. 46 and 48.

The tool members 9462, 9482 are rotatably coupled to the second link 9610 of the wrist assembly 9500 via a respective pin (not shown), which is disposed within a central opening 9468 of the tool member 9462 and a central opening (not shown) of the tool member 9482, which are aligned with openings 9689 of wrist assembly 9500.

The end effector 9460 can be operatively coupled to a mechanical structure in the same or similar manner as described for previous embodiments, such that the tool members 9462 and 9482 rotate about the axis of rotation $A_2$. For example, the drive surface 9471 of the drive pulley 9470 is configured to engage the first cable (not shown) such that a tension force exerted by the first cable along the drive surface 9471 produces a rotation torque about the rotation axis $A_2$. Similarly, the drive surface 9481 of the drive pulley 9480 is configured to engage the second cable (not shown) such that a tension force exerted by the second cable along the drive surface 9481 produces a rotation torque about the rotation axis $A_2$. In this manner, the contact portion 9464 of the tool member 9462 and the contact portion 9484 of the tool member 9482 can be actuated to engage or manipulate a target tissue during a surgical procedure.

As described above for previous embodiments, both the first cable (not shown) and the second cable (not shown) can extend from a mechanical structure (as described herein) and are coupled to the end effector 9460. More specifically, a distal end portion of the first cable is coupled to the first tool member 9462 of the end effector 9460 and a distal end portion of the second cable is coupled to the second tool member 9482 of the end effector 9460 in the same manner as described above for tool members 6462 and 6482.

FIGS. 49-54 illustrate a portion of another embodiment of an end effector that can be used with or incorporated within any of the medical instruments described herein. FIGS. 49-52 and 54 illustrate a portion of the end effector 10460, which end effector can be coupled to a wrist assembly (such as wrist assembly 9500) and a shaft (such as shaft 9410) of a medical instrument.

Figure 50:
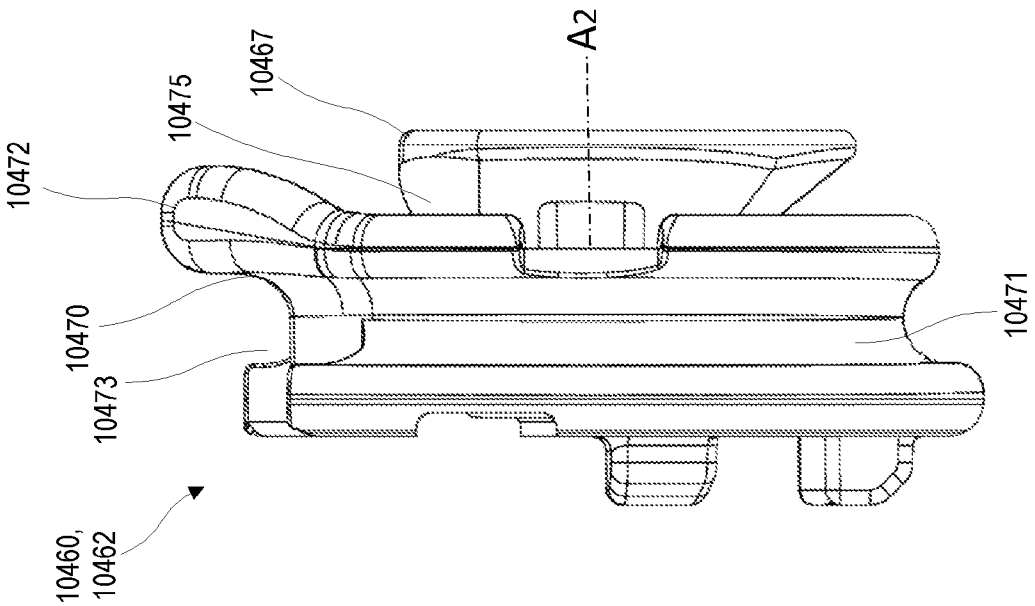
FIG. 50 is a side view of the portion of the end effector of FIG. 49.
Figure 49:
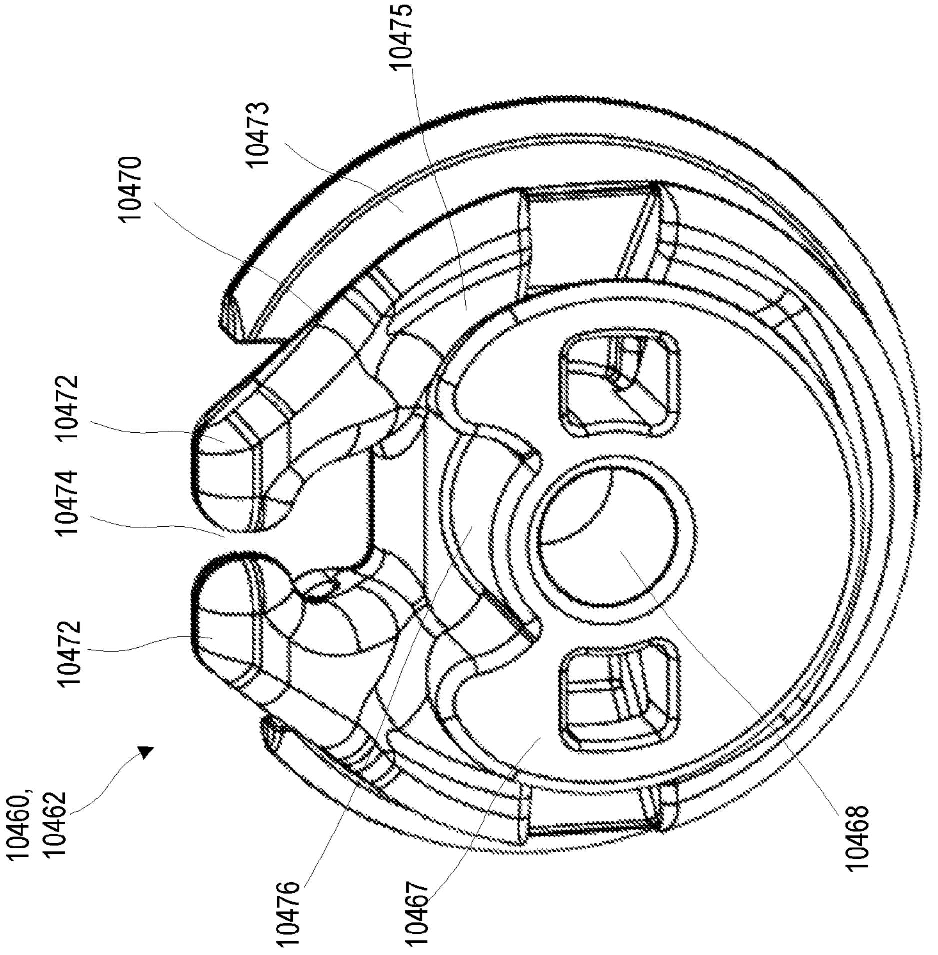
FIG. 49 is a perspective view of a portion of an end effector of a medical instrument according to an embodiment.
Figure 51:
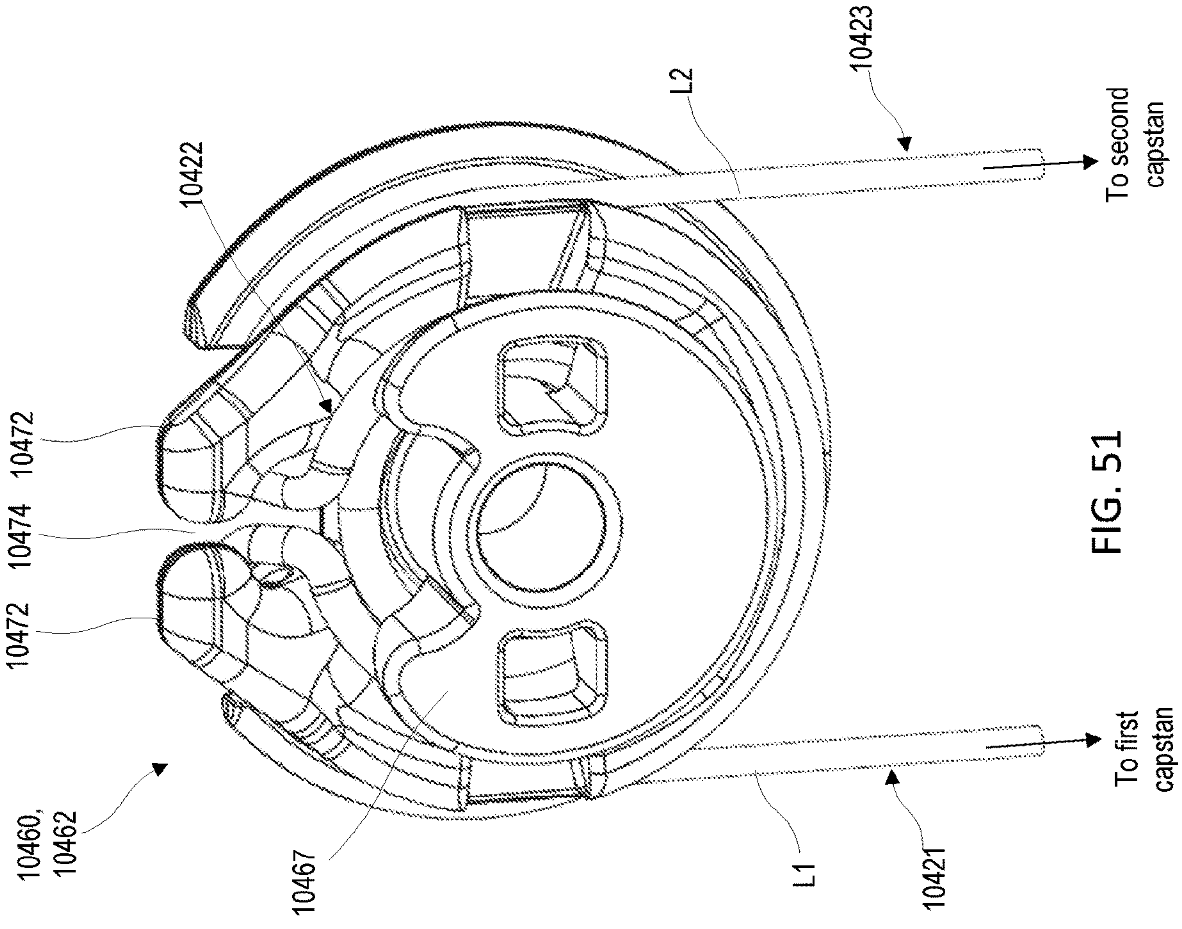
FIG. 51 is a perspective view of the portion of the end effector of FIG. 49 with a cable wrapped within the drive pulley and coupling spool of the end effector.

The end effector 10460 can include a first tool member 10462 and a second tool member (not shown) which can be constructed similar to and function similar to, for example, first and second tool members 9462 and 9482 described above). The below description is for only the first tool 10462, and it should be understood that the second tool can be constructed the same as and function the same as first tool 10462. As shown in FIG. 49-51, the first tool member 10462 includes a drive pulley 10470 and a coupling spool 10467. In this embodiment, the drive pulley 10470 and coupling spool 10467 can be formed as an integral or monolithic component that is welded (or otherwise coupled) to a contact portion (not shown) of the tool member 10460. In some embodiments, the contact portion can be formed as two parts—a stamped component, and the drive pulley 10470 and coupling spool 10467 are formed with a metallic material and machined or formed through a metal injection molding process.

As best shown in FIGS. 49 and 50, the drive pulley 10470 defines a guide channel 10473 with a drive surface 10471, and includes two protrusions 10472 that define an opening 10474 therebetween. The coupling spool 10467 defines a spool channel 10475 with a wrap surface 10476. As with previous embodiments, the guide channel 10473 and spool channel 10467 are configured to receive a distal end portion of a cable (shown in FIGS. 51-54D) as described in more detail below. As shown in the side view of FIG. 51, the drive pulley 10470 is disposed at a first location along an axis $A_2$ and the coupling spool 10467 is disposed at a second location along the axis $A_2$. In other words, the drive pulley 10470 and the coupling spool 10467 are disposed at a spaced distance from each other along the same rotational axis.

The first tool member 10462 and the second tool member (not shown) are rotatably coupled to a link of a wrist assembly as described herein for other embodiments via a respective pin (not shown). More specifically, the pin is disposed within a central opening 10468 of the first tool member 10462 and a central opening (not shown) of the second tool member (nots shown), which are aligned with openings of the wrist assembly.

The end effector 10460 can be operatively coupled to a mechanical structure in the same or similar manner as described for previous embodiments, such that the first tool member 10462 and second tool member (not shown) rotate about the axis of rotation $A_2$. For example, the drive surface 10471 of the drive pulley 10470 is configured to engage a first cable 10420 (described below and shown in FIGS. 51-54D) such that a tension force exerted by the first cable 10420 along the drive surface 10471 produces a rotation torque about the rotation axis $A_2$. Similarly, a drive surface of the drive pulley of the second tool member (not shown) is configured to engage a second cable (not shown) such that a tension force, exerted by the second cable along the drive surface of the second tool member, produces a rotation torque about the rotation axis $A_2$. In this manner, the contact portion of the first tool member 10462 and a contact portion of the second tool member (not shown) can be actuated to engage or manipulate a target tissue during a surgical procedure.

As described above for previous embodiments, both the first cable 10420 and the second cable (not shown) can be coupled to a mechanical structure (as described herein) and extend to and be coupled to the end effector 10460. More specifically, a distal end portion 10422 of the first cable 10420 is coupled to the first tool member 10462 of the end effector 10460 and a distal end portion of the second cable (not shown) is couple to the second tool member (not shown) of the end effector 10460 as described below for first cable 10420 with reference to FIGS. 52-54. The second cable can be coupled in the same manner.

The first cable 10420 and the second cable each include a first proximal portion 10421, a second proximal portion 10423, and the distal portion 10422 (see e.g., FIGS. 51 and 52), the same as or similar to cable 2420 shown in FIG. 5. As described above for cable 2420, the first proximal end portion 10421 and the second proximal end portion 10423 are each coupled to the mechanical structure of the medical instrument, as described in more detail below with reference to FIGS. 55-66, and the distal portion 10422 is coupled to the end effector (i.e., the first and second tool members). In some embodiments, the cables can be constructed from a polymer as described above for the cable 2420.

Figure 52:
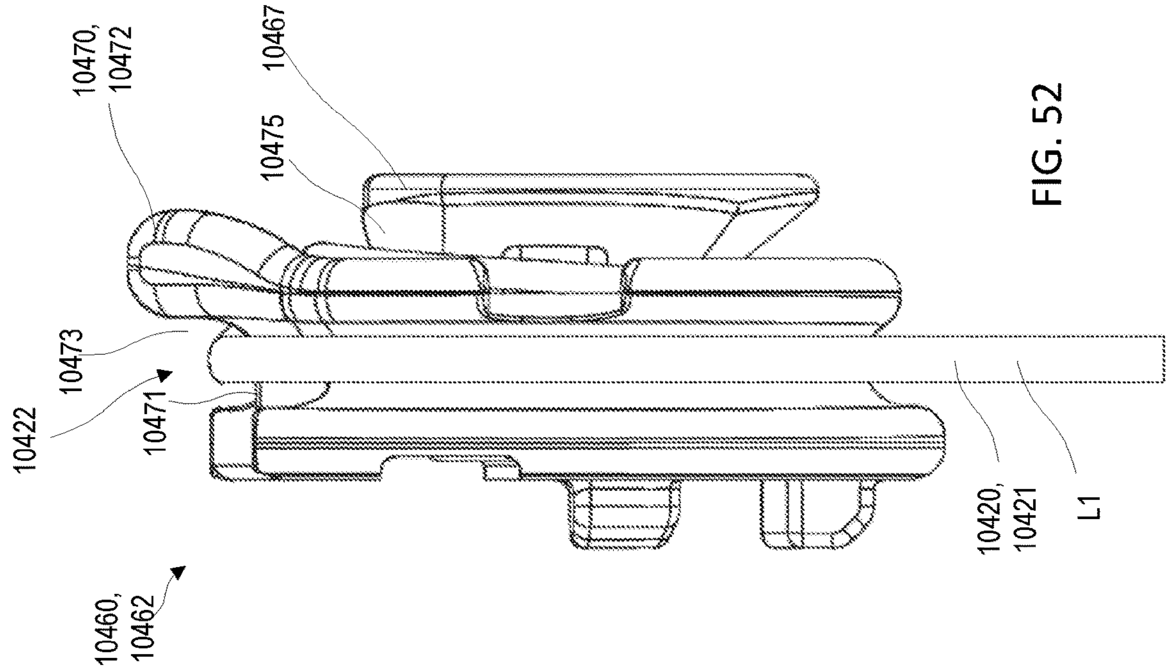
FIG. 52 is a side view of the portion of the end effector of FIG. 49 with the cable wrapped within the drive pulley and coupling spool of the end effector.

In this embodiment, the first cable 10420 is coupled to the first tool member 10462 of the end effector 10460 as shown in FIGS. 51 and 52. It should be understood that the second cable (not shown) can be coupled to the second tool member (not shown) of the end effector 10460 in the same manner. More specifically, in this embodiment, the distal end portion 10422 of the first cable 10420 is wrapped about the first tool member 10462, then extends along the shaft of the medical instrument, and the first proximal end portion 10421 is coupled to a first capstan and the second proximal end portion 10423 is coupled to a second capstan of the mechanical structure of the medical instrument (as described below). The second cable is similarly coupled to the second tool member and routed along the shaft and coupled to a third capstan and a fourth capstan of the mechanical structure.

Figure 53:
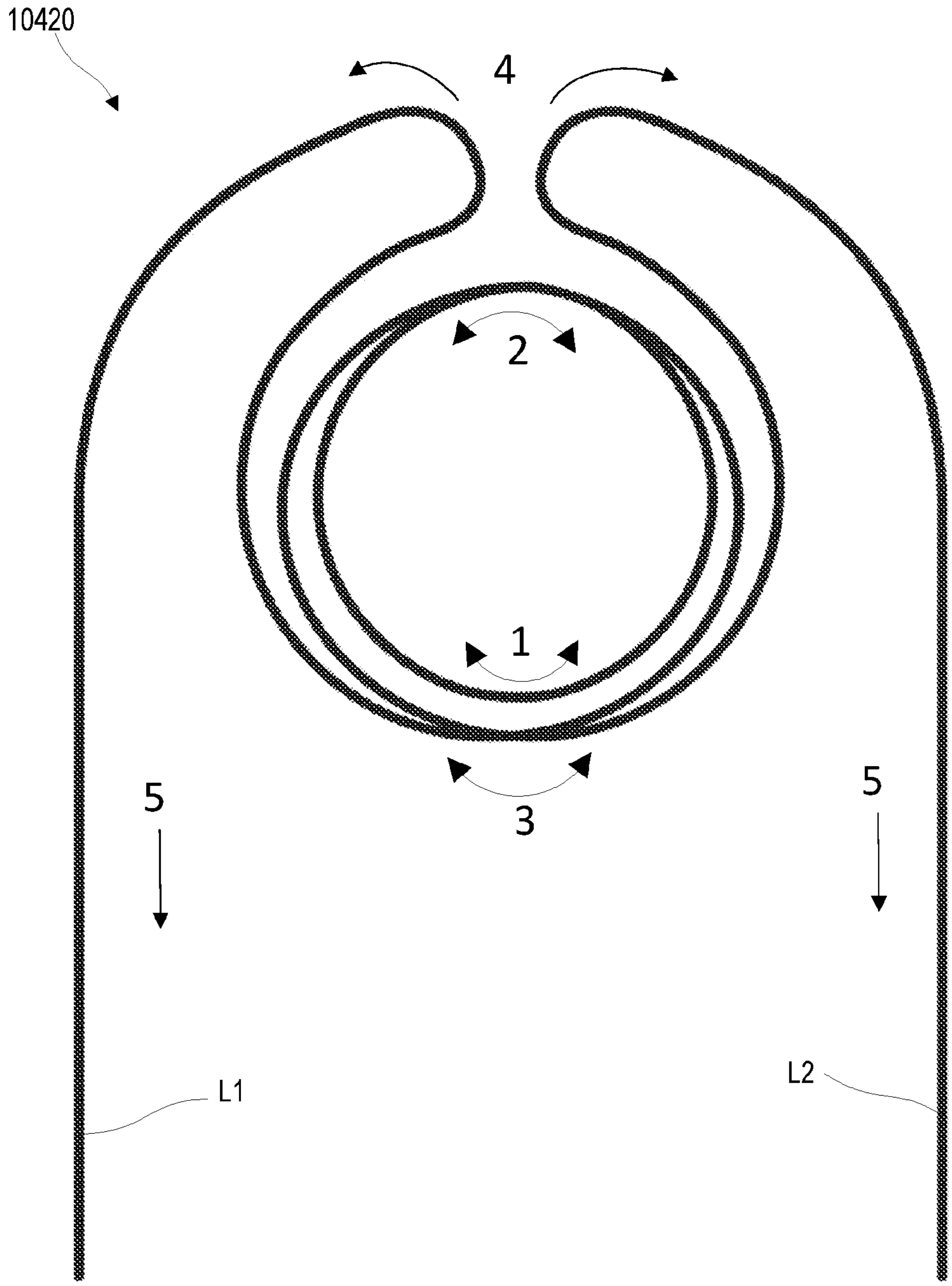
FIG. 53 is a perspective view of a schematic illustration of the cable in a wrap pattern shown removed from the end effector for illustration purposes.
Figure 54B:
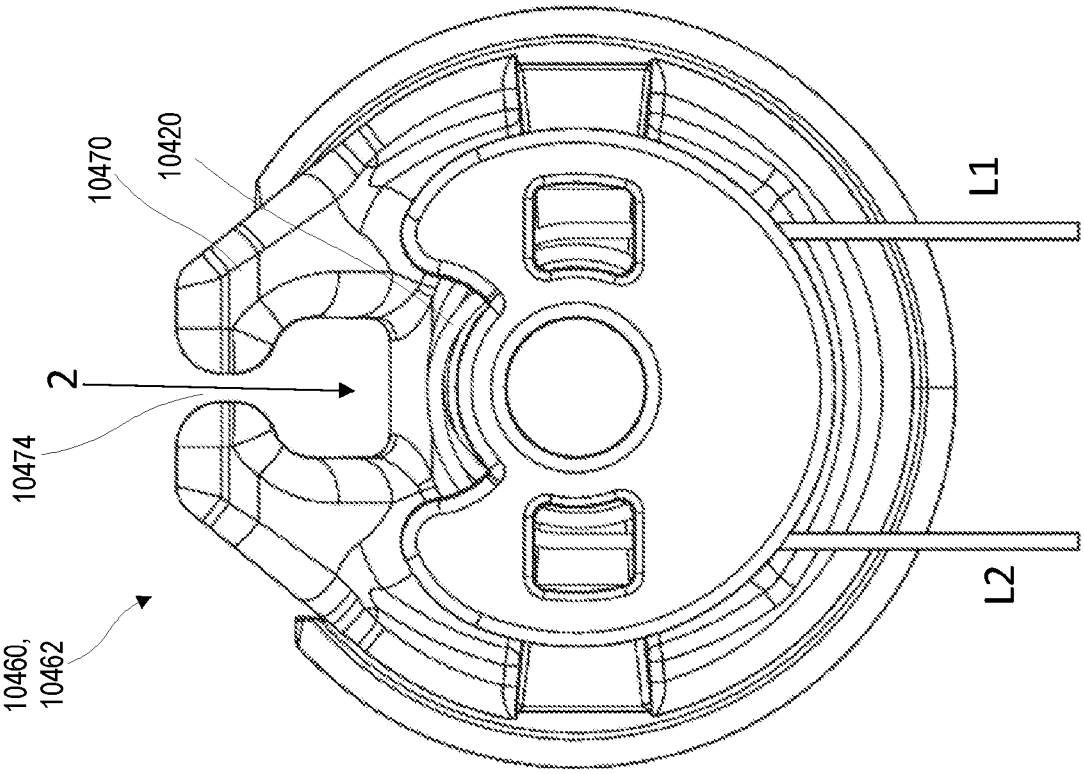
FIGS. 54A-54D each illustrate a step in a wrap sequence for a cable to be coupled to the end effector of FIG. 49.
Figure 54A:
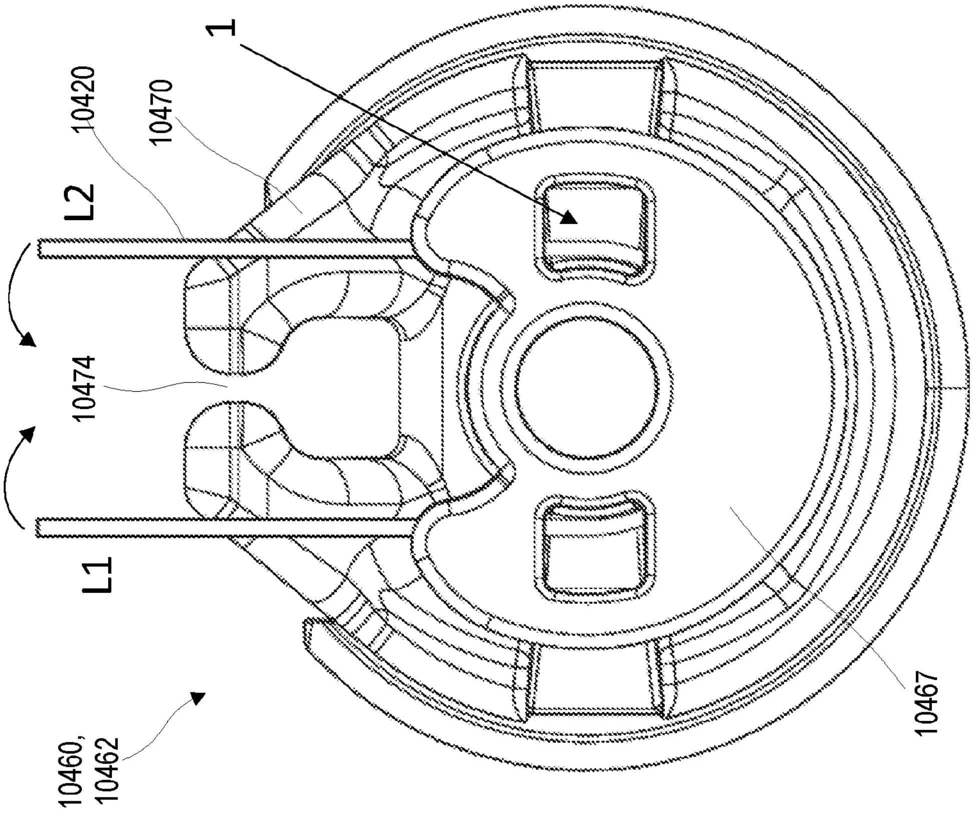
Figure 54D:
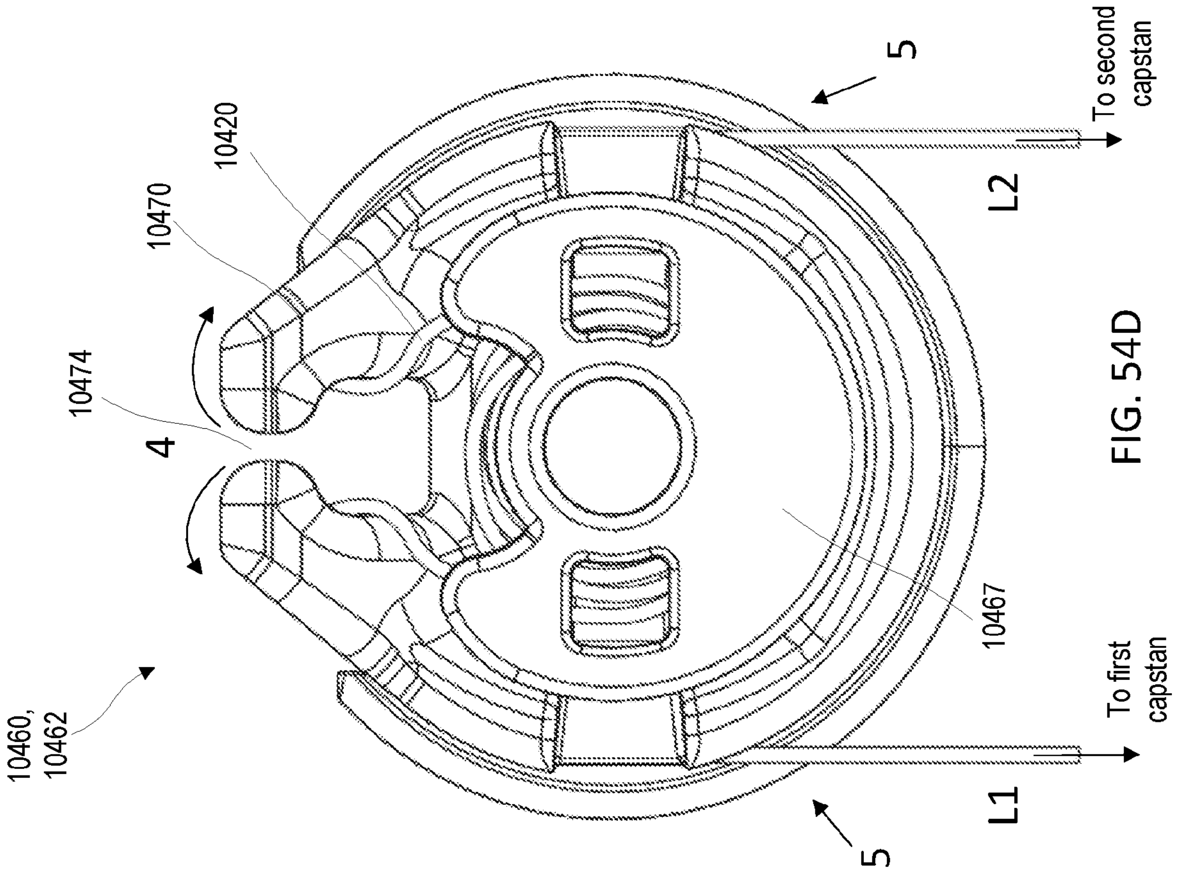
Figure 54C:
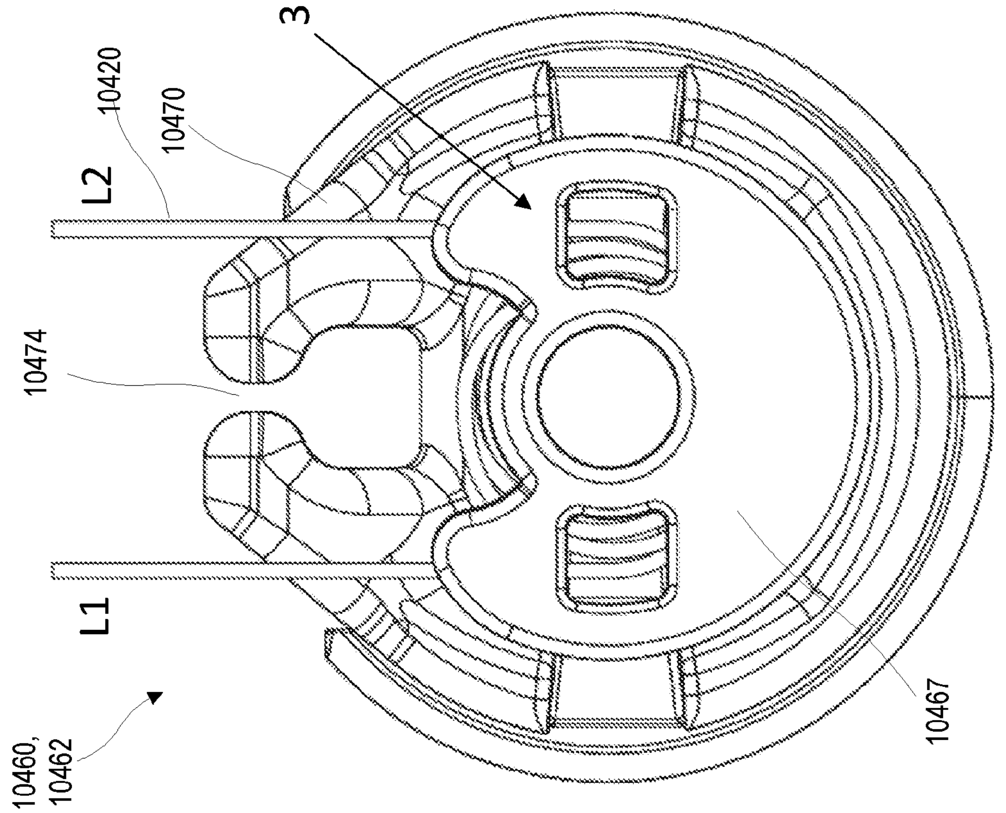

FIG. 53 is a schematic illustration of the cable in a wrapped configuration removed from the tool member 10462 for illustration purposes, and FIGS. 54A-54D illustrate steps in the process to wrap and couple the first cable 10420 to the first tool member 10462. To couple the first cable 10420 to the first tool member 10462, the distal end portion 10422 is placed under and against the bottom side (i.e., the side furthest away from the protrusions 10472) of the wrap surface 10476 within the spool channel 10475, as indicated at arrows 1 in FIGS. 53 and 54A. Said another way, approximately a middle portion of the first cable 10420 is placed against the bottom of the wrap surface 10476 with the lengths L1 and L2 of the cable on each side of the middle portion extending upward as shown in FIG. 54A. A portion of each length L1 and L2 of the first cable 10420 extending from each side of the wrap surface 10476 is then wrapped about the wrap surface 10476 in opposite directions, a first time crossing over each other at a top side (i.e., the side closest to the protrusions 10472) of the wrap surface 10476 within the spool channel 10475, as indicated at arrows 2 in FIGS. 53 and 54B. In other words, length L1 is wrapped counterclockwise and length L2 is wrapped clockwise. A portion of each length L1 and L2 of the first cable 10420 is then wrapped about the wrap surface 10476 in opposite directions (L1 counterclockwise and L2 clockwise) again crossing over each other at a bottom side of the wrap surface 10476 within the spool channel 10475 and partially around the wrap surface 10476 towards the top of the spool channel 10475, as indicated at arrows 3 in FIGS. 53 and 54C. A portion of each length L1 and L2 of the first cable 10420 is then routed through the opening 10474 defined between the protrusions 10472 of the drive pulley 10470, as indicated at arrows 4 in FIGS. 53 and 54D (and also shown in FIGS. 51 and 52). The opening 10474 can be sized (e.g., diameter or width) such that it is smaller than a nominal size (diameter or width) of the cable 10420 such that a force is required to pass the lengths L1 and L2 of the cable 10420 through the opening 10474. For example, in some embodiments, the opening 10474 can have a nominal diameter or width of about half the size of the diameter or width of the cable 10420. In some embodiments, the cable 10420 can be a polymeric cable that can deform when forced through opening 10474. Thus as the cable 10420 is passed through the opening 10474, the cable can deform to fit through the opening 10474. For example, in some embodiments, the cable 10420 has a circular cross-section prior to being passed through the opening 10474 and can deform to a different shape when passed through the opening 10474. In other words, the cable 10420 may not maintain a circular cross-section. Each length L1 and L2 of the first cable 10420 on opposite sides of the opening 10474 are then routed along the drive surface 10471 in opposite directions within the guide channel 10473 as indicated at arrows 5 in FIGS. 53 and 54D.

With the first cable 10420 coupled to the first tool member 10462, the contact surface and friction force of the cable 10420 against the wrap surface 10476 of the coupling spool 10467 and along the drive surface 10471 of the drive pulley 10470 maintain the cable 10420 to the first tool member 10462 without the use of additional fastening or retention components. In addition, as described above, the size of the opening 10474 is smaller than the size of the cable 10420 such that increased friction is created between the cable 10420 and the first tool ember 10462, and the contact between the cable 10420 and the surface of the protrusions 10472 also provides additional engagement surfaces and increased friction between the cable 10420 and the first tool member 10462. Such increased friction between the first tool member 10462 and the cable 10420 assists in maintaining the cable 10420 coupled to the first tool member 10462. The increased friction can also reduce the possibility of slippage of the cable 10420 during operation of the medical instrument.

By wrapping the length L1 counterclockwise and the length L2 clockwise within the spool channel 10475, neither length of cable L1 or L2 is consistently wrapped over the other. Similarly stated, by wrapping both lengths L1 and L2 of the cable in opposing wrap directions, this cable wrap pattern prevents one length portion L1 or L2 from being consistently underneath the other portion. For example, referring to FIG. 54A, a portion of the length L1 is innermost within a portion of the spool channel 10475 on the left, and a portion of the length L2 is innermost within a portion of the spool channel 10475 on the right. In this manner, the effect of the tension applied to either length L1 or length L2 of the cable 10420 will have a more consistent effect on the friction force that maintains the coupling of the cable 10420 to the first tool member 10462. This further prevents slippage of the cable 10420 during operation of the medical instrument when tension is applied to the cable 10420.

After being coupled to the first tool member 10462, each length L1, L2 of the first cable 10420, including the first and second proximal end portions 10421 and 10423 are then routed from the first tool member 10462, through or along the shaft and to the first and second capstan of the mechanical structure, as described below. For example, the first and second proximal end portions 10421 and 10423 of the first cable 10420 can extend within an interior lumen of the shaft or can be routed exterior to the shaft, and be coupled to the first and second capstans of the mechanical structure.

More specifically, the first proximal end portion 10421 is coupled to a first capstan 10710 (shown in FIGS. 55-66) and the second proximal end portion 10423 is coupled to a second capstan (not shown) of the mechanical structure of the medical instrument (as described below). The description below describes the first capstan 10710 and the coupling of the first proximal end portion 10421 of the first cable 10420 thereto, but it should be understood that the second proximal end portion 10423 of the first cable 10420 can be coupled to the second capstan in the same manner. Further, the routing of the second cable (not shown) between the end effector and the mechanical structure is not described below, but it should be understood that the second cable can be routed and coupled to a third and fourth capstan in the same manner as the first cable.

More specifically, the two ends of the first cable 10420 that are associated with opposing directions of a single degree of freedom are connected to two independent drive capstans (first capstan 10710 and a second capstan (not shown)). This arrangement, which is generally referred to as an antagonist drive system as described above for previous embodiments, allows for independent control of the movement of (e.g., pulling in or paying out) each of the ends of the cable. The mechanical structure produces movement of the first cable 10420 and the second cable, which operates to produce the desired articulation movements (pitch, yaw, cutting or gripping) at the end effector 10460. Accordingly, as described herein, the mechanical structure includes components and controls to move a first portion of the first cable 10420 via the first capstan 10710 in a first direction (e.g., a proximal direction) and to move a second portion of the first cable 10420 via the second capstan (not shown) in a second opposite direction (e.g., a distal direction). The mechanical structure can also move both the first portion of the first cable 10420 and the second portion of the first cable 10420 in the same direction. The mechanical structure also includes components and controls to move a first portion of the second cable (not shown) via a third capstan (not shown) in a first direction (e.g., a proximal direction) and to move a second portion of the second cable via the fourth capstan (not shown) in a second opposite direction (e.g., a distal direction). The mechanical structure can also move both the first portion of the second cable and the second portion of the second cable in the same direction. In this manner, the mechanical structure can maintain the desired tension within the cables to produce the desired movements at the end effector 10460.

As shown in FIGS. 55-59, the first capstan 10710 includes a first portion 10715 (which functions as a spool portion) having a drive surface 10716, and a second portion 10714 (which functions as an anchor portion to secure the cable to the capstan 10710) having a coupling surface 10733. In this embodiment, the drive surface 10716 is a circular groove defined about a longitudinal axis Ac of the capstan 10710.

Figure 55:
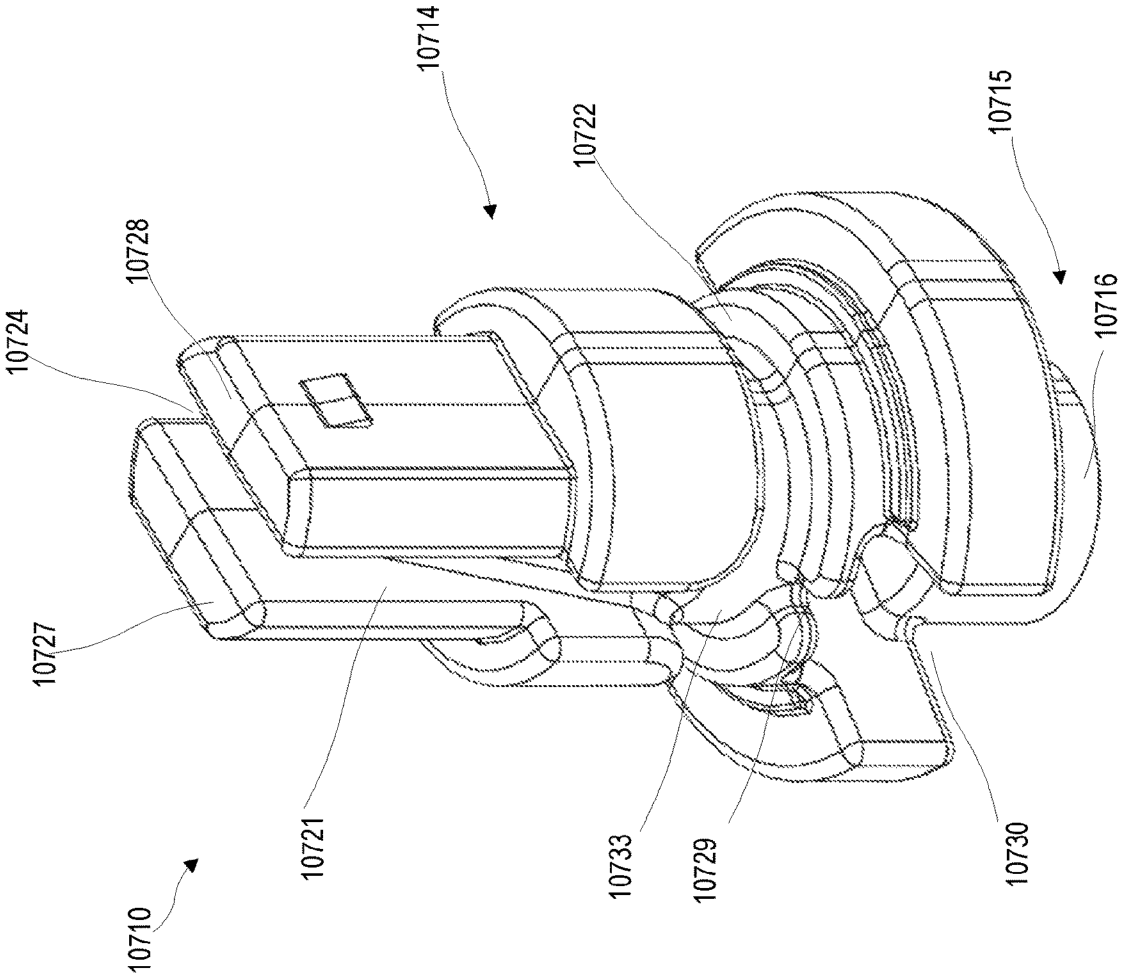
FIG. 55 is a perspective view of a capstan of a medical instrument according to an embodiment.
Figure 57:
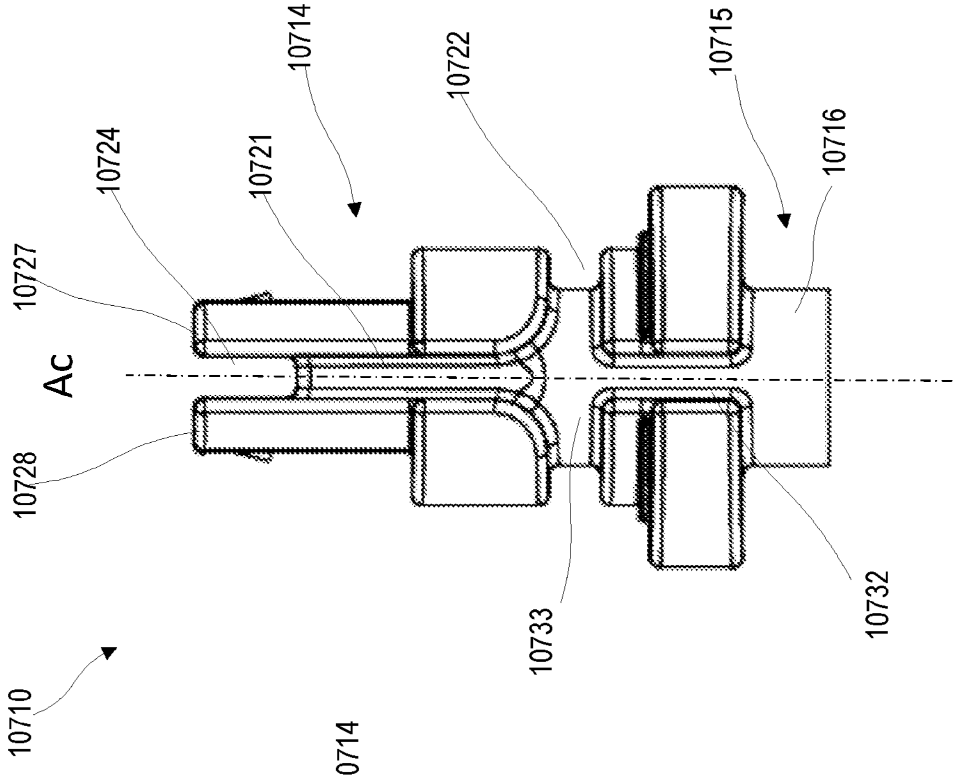
FIG. 57 is a back view of the capstan of FIG. 55.
Figure 56:
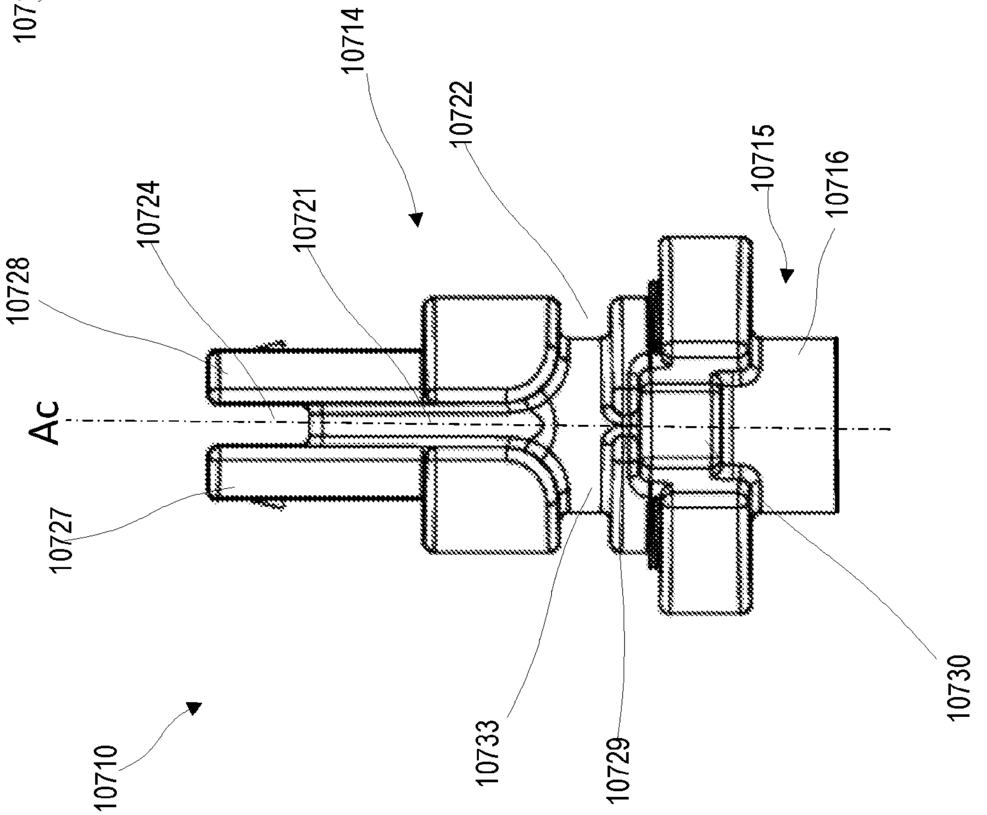
FIG. 56 is a front view of the capstan of FIG. 55.
Figure 59:
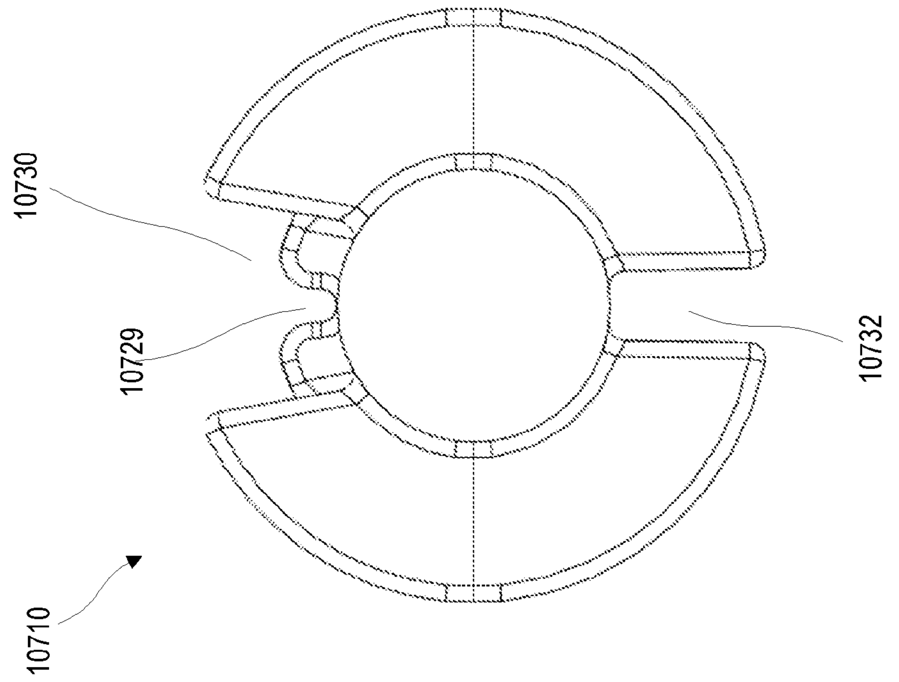
FIG. 59 is a bottom view of the capstan of FIG. 55.
Figure 58:
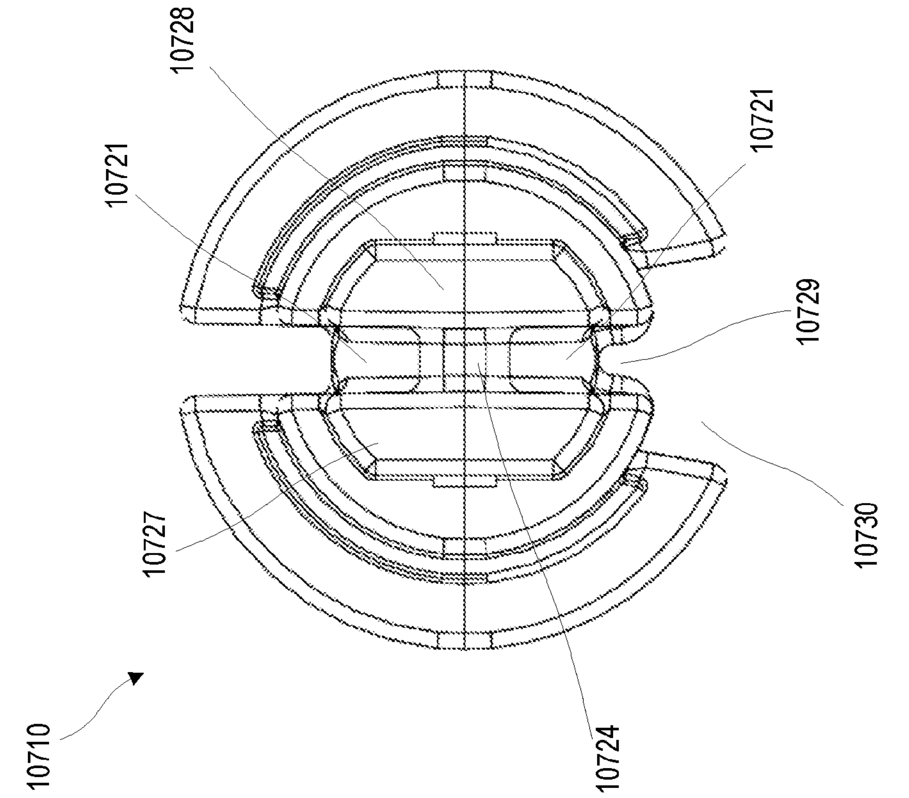
FIG. 58 is a top view of the capstan of FIG. 55.

The second portion 10714 of the first capstan 10710 is cylindrical about the longitudinal axis Ac. The second portion 10714 also defines a first slot 10721 that extends along the longitudinal axis Ac and a second slot 10722 that crosses (or is transverse to) the first slot 10721. In some embodiments, the first slot 10721 is perpendicular to the second slot 10722. The second portion 10714 also defines a top slot 10724 defined between two posts 10727 and 10728 and that crosses the first slot 10721. As shown in FIGS. 55 and 56, a guide opening 10729 and an access opening 10730 are each defined on a first or front side of the capstan 10710. The guide opening 10729 can be used as a locator guide when coupling the first cable 10420 to the capstan 10710 as described below. In some embodiments, the guide opening 10729 is sized larger that the size (e.g., diameter or width) of the cable 10420 such that the cable 10420 can be placed within the guide opening 10729 without exertion of force or friction between the capstan 10710 and the cable 10420. In some embodiments, the guide opening 10729 can be sized (e.g., diameter or width) smaller than the size (e.g., diameter or width) of the cable, such that a pinch point is created between the capstan 10710 and the cable 10420 to capture a portion of the cable 10420. In some embodiments, the guide opening 10729 can be a tapered lumen. The access opening 10730 can be used to provide access for a cutting tool to cut the first cable 10420 after coupling the first cable 10420 to the capstan 10710 as described in more detail below. As shown in FIG. 57, an elongate slot 10732 is defined on a second or back side of the capstan 10710, which can be used to route the first cable 10420 to the drive surface 10716 as described in more detail below.

As described above, after being coupled to the first tool member 10462 of the end effector 10460, the first proximal end portion 10421 of the first cable 10420 extends along or through the shaft and to the first capstan 10710 of the mechanical structure to be coupled thereto. The first proximal end portion 10421 of the first cable 10420 is routed along a particular path on the capstan 10710, and secured thereto without the need for a separate retention element (e.g., a crimp, retention member on the cable, or the like).

Figure 61:
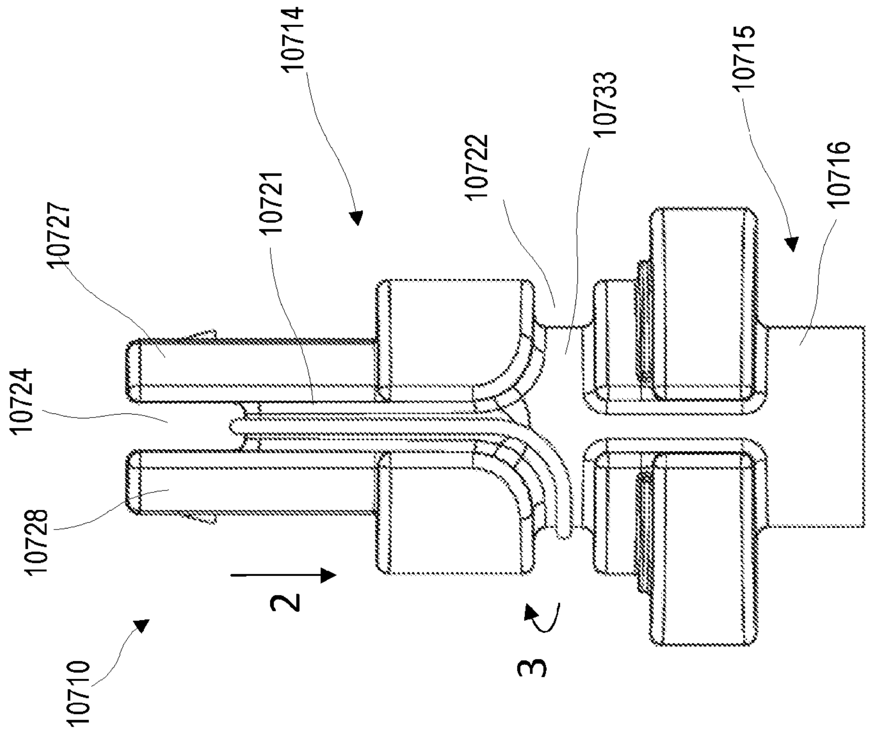
FIGS. 60-66 each illustrate a step in a wrap sequence for a cable to be coupled to the capstan of FIG. 55.
Figure 60:
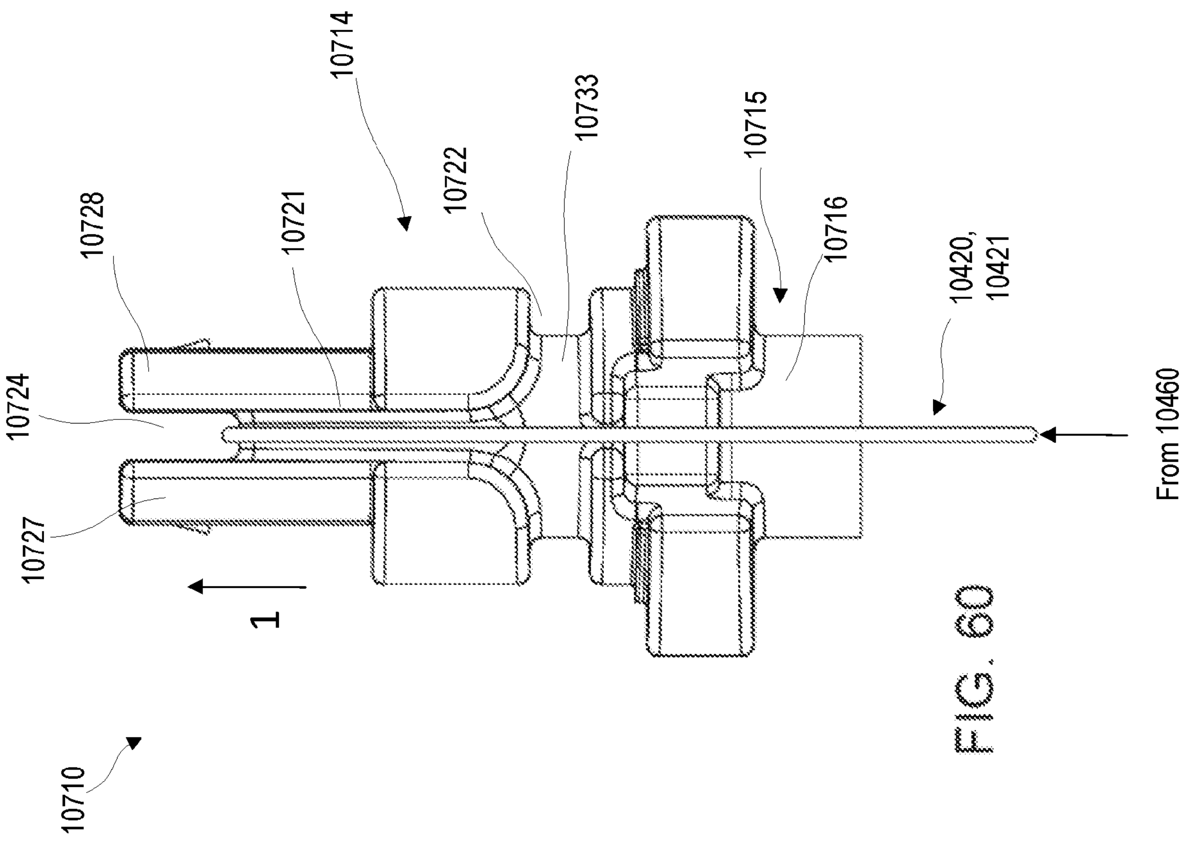
Figure 63:
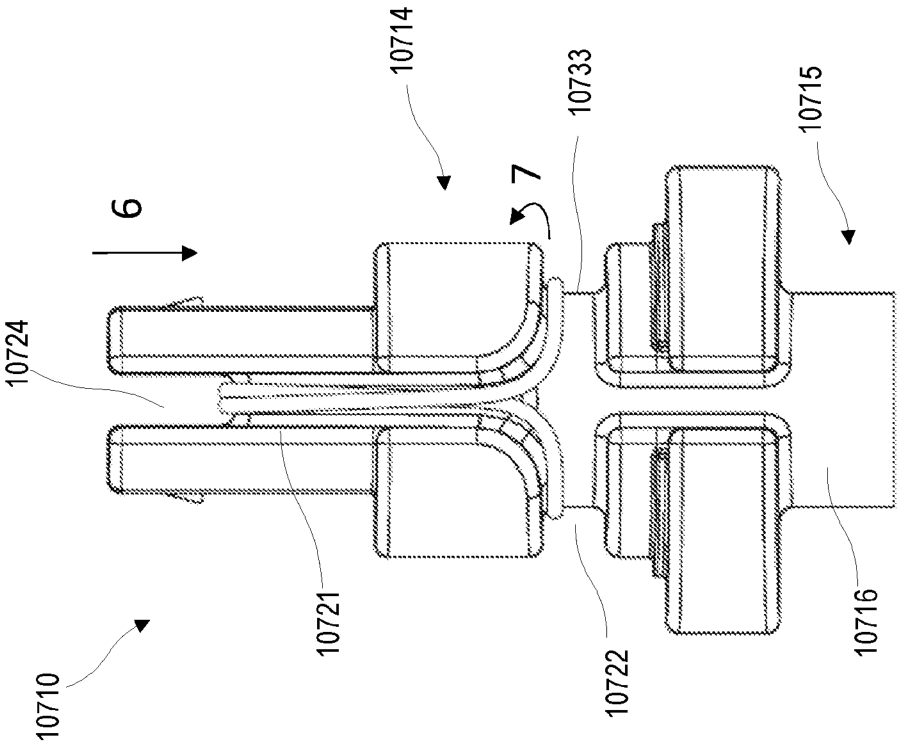
Figure 62:
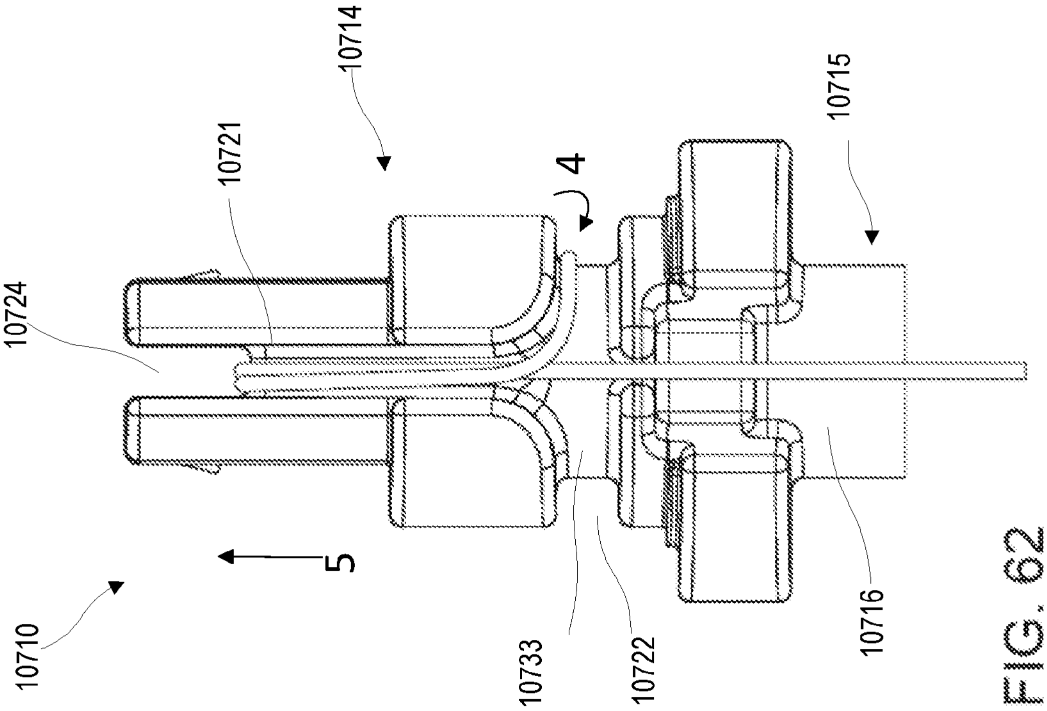
Figure 65:
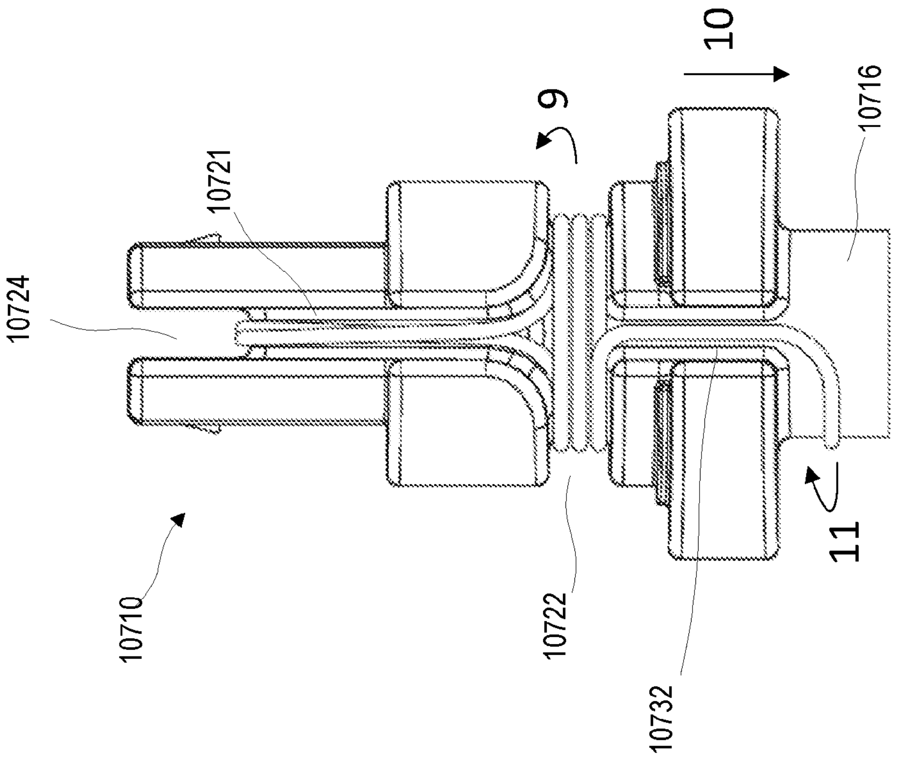
Figure 64:
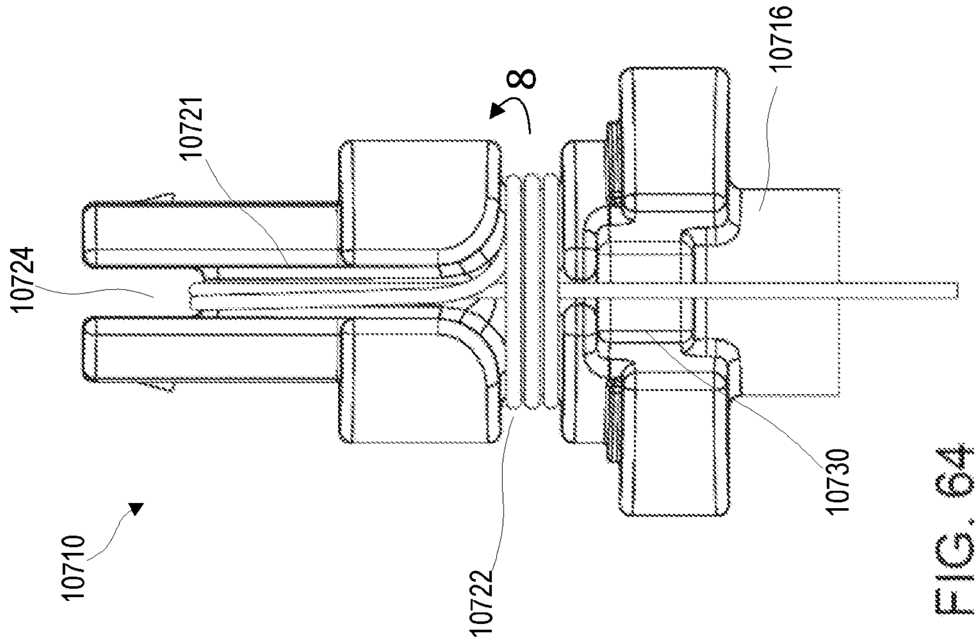
Figure 66:
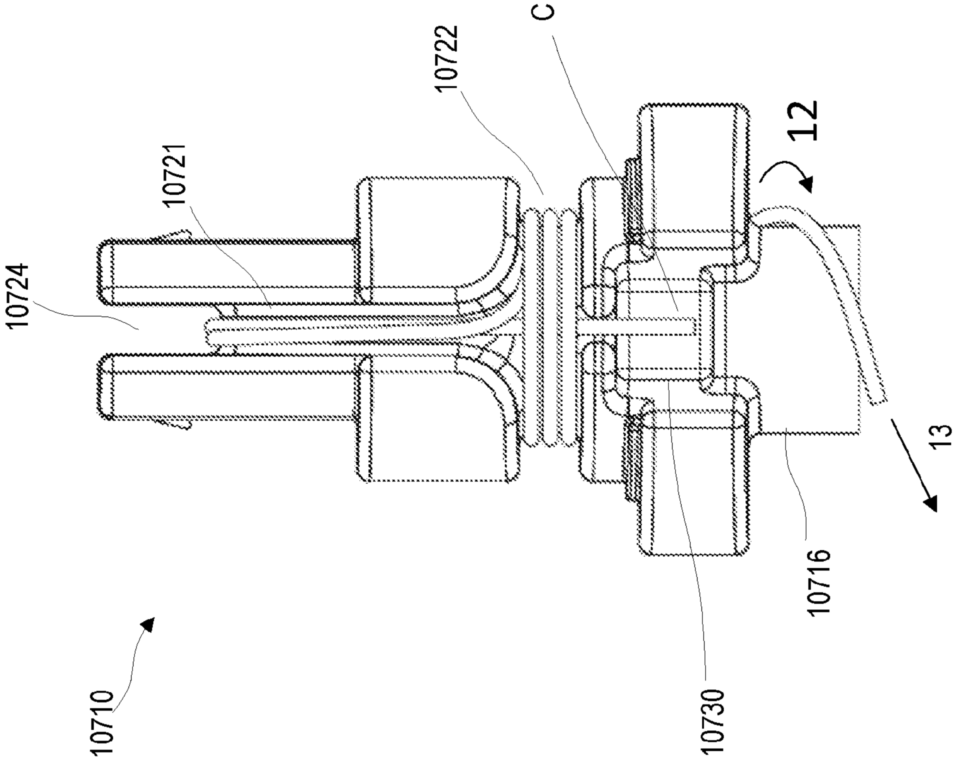
Figure 67:
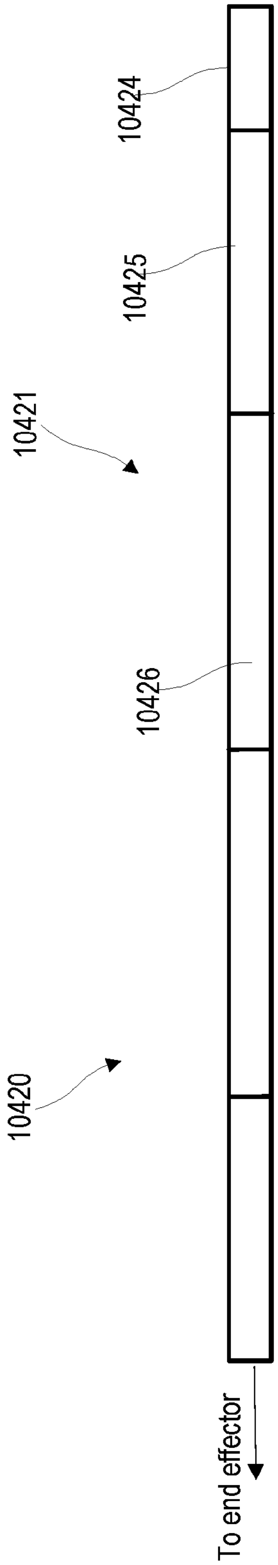
FIG. 67 is a side view of a portion of a cable, according to an embodiment.

More specifically, the first proximal end portion 10421 of the cable 10420 includes a termination end portion 10424, a first wrap portion 10425, a second wrap portion 10426 and a drive portion 10427, as shown in FIG. 67. As shown in FIG. 60, the first proximal end portion 10421 of first cable 10420 extends from the end effector 10460 and is placed within the guide opening 10729 such that a termination end portion of the first cable 10420 extends a select distance through the access opening 10730. The guide opening 10729 assists in positioning the cable 10420 within the first slot 10721 during coupling of the cable 10420 to the capstan 10710. A portion of the proximal end portion 10421, including the first wrap portion 10425, is routed upward through the first slot 10721 and over the third slot 10724 (as indicated at arrow 1 in FIG. 60). As shown in FIG. 61, a portion of the first cable 10420 is then routed through the first slot 10721 on the second side of the capstan 10710 and is routed through the second slot 10722 and wrapped about the coupling surface 10733 towards the first side of the capstan 10710 as indicated at arrows 2 and 3 in FIG. 61. The portion of the first cable 10420 is then routed within the second slot 10722 on the first side of the capstan 10710 and back up through the first slot 10721 as indicated at arrows 4 and 5 in FIG. 62. As shown in FIG. 63, the portion of the first cable 10420 is then routed through the first slot 10721 on the second side of the capstan 10710 and a second portion of the cable 10420, including the second wrap portion 10426, is routed through and wrapped about the coupling surface 10733 of the second slot 10722 in the opposite direction towards the first side of the capstan 10710, crossing over the first wrap portion 10425, as indicated at arrows 6 and 7 in FIG. 63. A portion of the first cable 10420 is then wrapped about the coupling surface 10733 twice as indicated at arrow 8 in FIG. 64, again crossing over the first wrap portion, and crossing over the termination end portion 10424 of the cable 10420 that extends along the drive surface 10733 and within the guide opening 19729 and access opening 10732. As shown in FIG. 65, a portion of the first cable 10420, is then wrapped back around the coupling surface 10733 to the second side of the capstan 10710 as indicated at arrow 9, then down through the elongate slot 10732 as indicated at arrow 10 and then around the drive surface 10716 as indicated at arrow 11. As shown in FIG. 66, a portion of the first cable 10420 is wrapped around the drive surface 10716 to the first side of the capstan 10710 and extends to the end effector 10460, as indicated at arrow 13.

After the first cable 10420 is coupled to the capstan 10710, the proximal end portion 10421 can be cut to remove excess cable. For example, as shown in FIG. 66, a cutting tool (not shown) can cut an end portion off the first cable 10420 at a location C within the access opening 10730. For example, the end can be cut with a heat cutter or by fusing the end or other suitable cutting tool. The length of the first cable 10420 is sized to enable the first cable 10420 to be coupled to the end effector 10460 and then coupled to the capstan 10710 such that there is slack in the cable during transport and storage. In other words, the cable 10420 is not in tension during transport and storage. By limiting the cable tension during storage, the amount of cable stretch can be reduced or eliminated.

With the first cable 10420 coupled to the mechanical structure (not shown) and to the end effector 10460, rotational movement produced by the first capstan 10710 and the second capstan (not shown) can cause movement at the first tool member 10462 and the second tool member (not shown), respectively. Thus, as described previously, better control of the overall movement of the end effector 10460 (and tool members) can be achieved.

Figure 69:
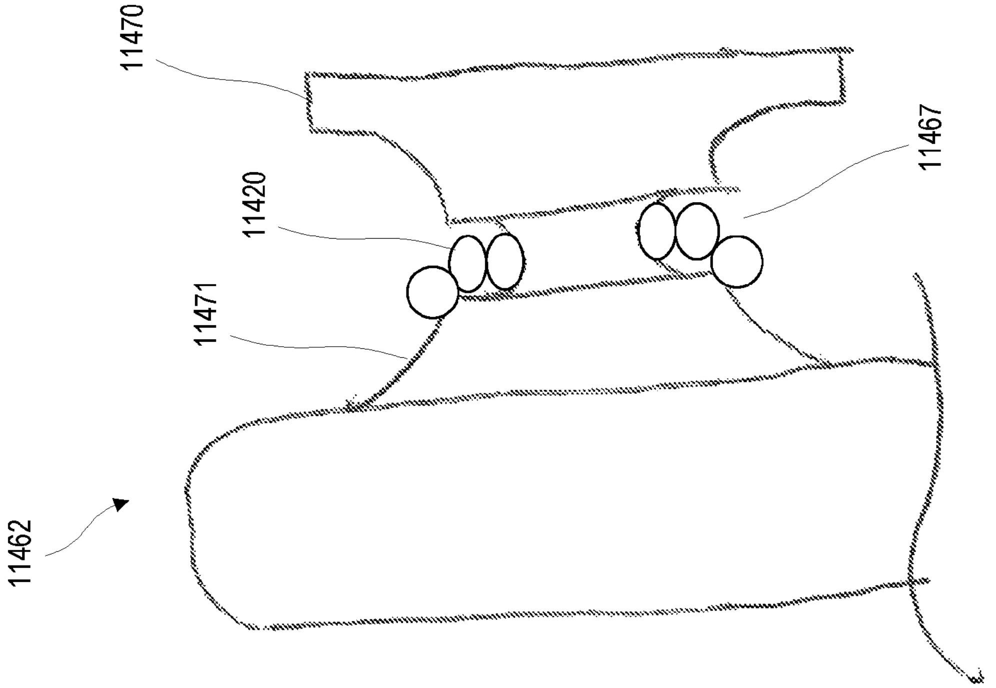
FIG. 69 is a side view of the tool member of FIG. 68 illustrating a portion of a cable coupled thereto.
Figure 68:
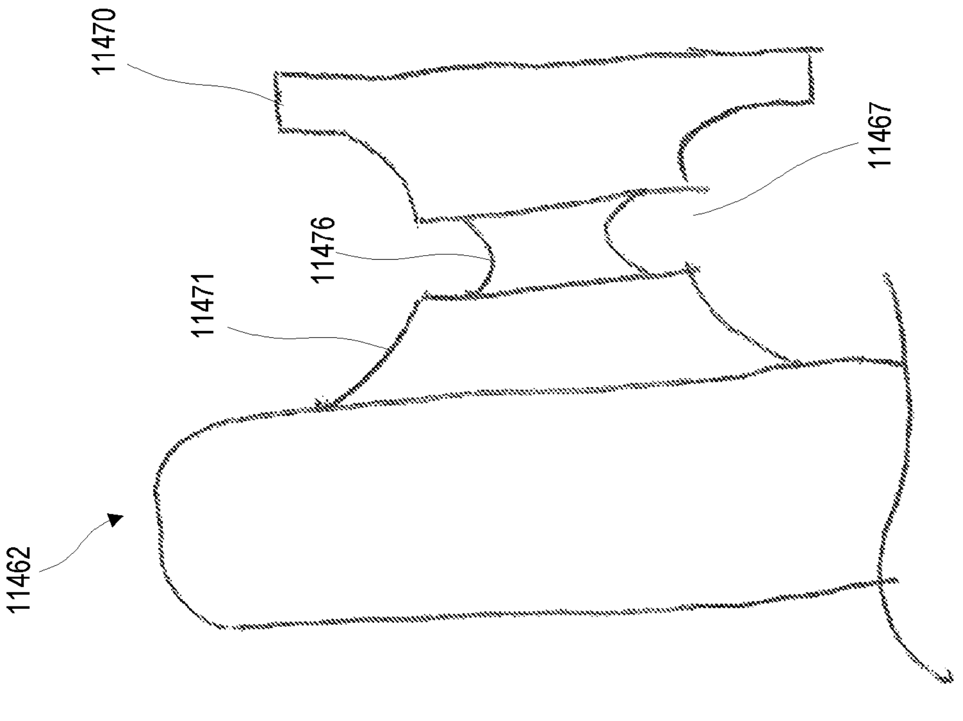
FIG. 68 is a side view of a tool member of a medical instrument, according to an embodiment.

Although many of the embodiments described herein show a tool member (e.g., 10462) having a coupling spool that is separate from a drive pulley, in other embodiments, any of the tool members described herein can include a coupling portion (e.g., where the cable is wrapped to couple the cable to the tool member) that is also within (or a part of) the drive pulley portion. In this manner, the tool geometry can be made simpler by eliminating a separate coupling spool. For example, in some embodiments, a wrap groove can be defined by the drive surface of a drive pulley. Such a groove can be linear (as shown in FIGS. 68 and 69) or can be curved or have a zig-zag or switchback pattern (as shown for capstan 11710 in FIGS. 70 and 71). This construction can increase contact surface between the coupling portion and the cable to improve retention of the cable by the tool member.

FIGS. 68-69 illustrate an alternative embodiment of a tool member of an end effector that includes a groove within the drive surface of the tool member. More specifically, the tool member 11462 includes a drive pulley 11470 that includes a drive surface 11471 and a coupling portion 11467 is defined by the drive surface 11471. The coupling portion 11467 includes a groove with a wrap surface 11476. As shown in FIG. 69, a cable 11420 can be wrapped around the drive pulley 11470 on the wrap surface 11476 within the coupling portion 11467 to couple the cable 11420 to the tool member 11462 and then contact the drive surface 11471 of the drive pulley 11470. The cable 11420 is shown in FIG. 69 (and in FIG. 71) in a cross-sectional view for illustration purposes. In this embodiment, the cable 11420 is wrapped two revolutions around the wrap surface 11476. In alternative embodiments, a cable can be wrapped one time or more than two revolutions around the wrap surface. The cable 11420 can be the constructed the same as or similar to the cables described herein, such as cable 2420 described above.

Figure 70:
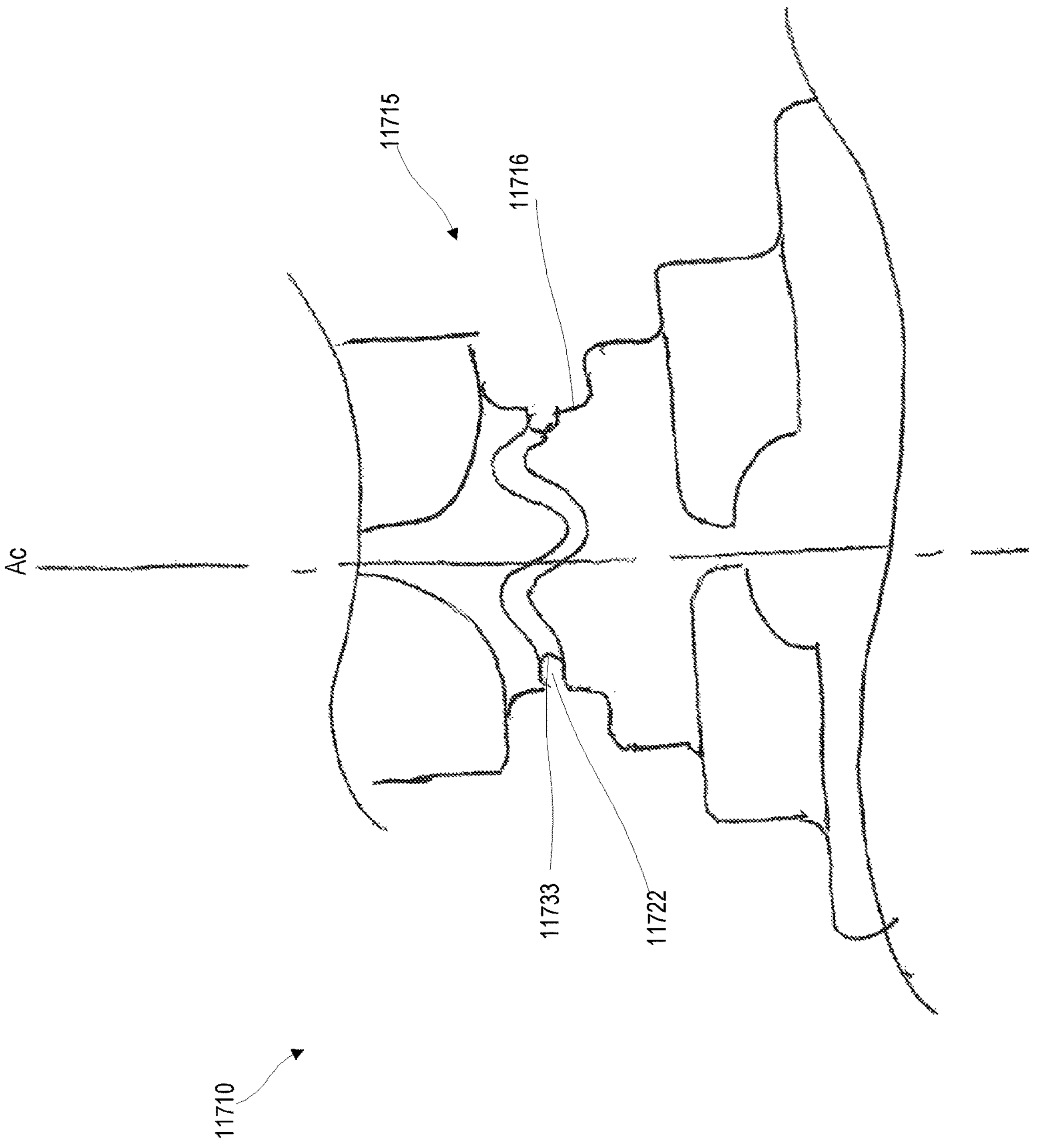
FIG. 70 is a side view of a portion of a capstan of a medical instrument, according to an embodiment.
Figure 71:
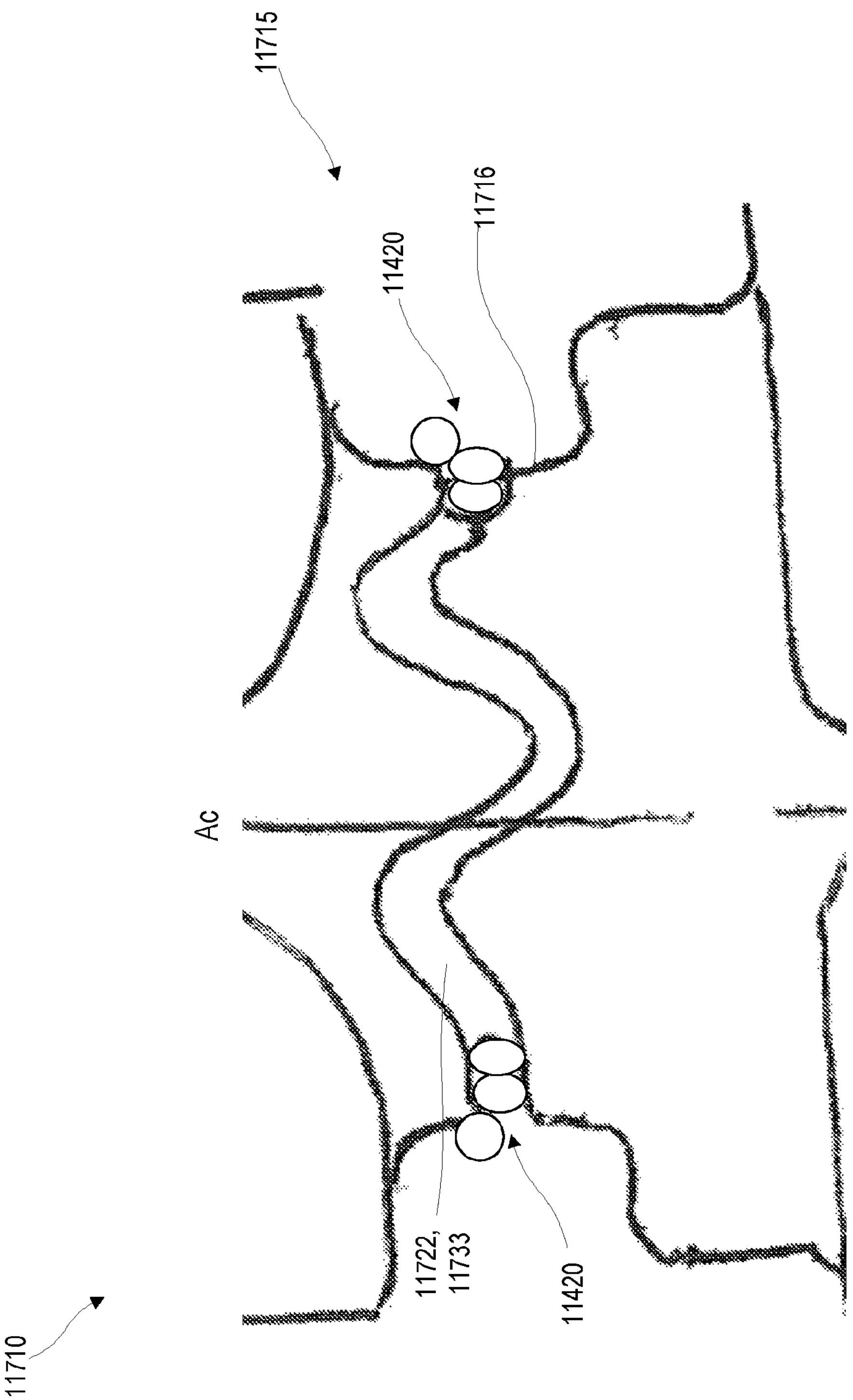
FIG. 71 is an enlarged view of a portion of the capstan of FIG. 70 illustrating a portion of a cable coupled thereto.

Similarly for the capstan of a medical instrument as described herein, although many of the embodiments described show a capstan (e.g., 10710) having a first portion (which functions as a spool portion) having a drive surface, and a second portion (which functions as an anchor portion to secure the cable to the capstan) having a coupling surface, in alternative embodiments, a capstan can include a portion that includes both the drive surface portion and the coupling surface portion. For example, as described for the tool member 11462 above, in some embodiments, a coupling groove and surface can be defined by the drive surface of a capstan. Such a groove can be linear (as shown in FIGS. 67 and 68 for tool member 11462) or can be curved or have a zig-zag or switchback pattern, as shown in FIGS. 70 and 71. This construction can increase contact surface between the coupling portion of the capstan and the cable to improve retention of the cable by the capstan.

FIGS. 70 and 71 illustrate a portion of a capstan that includes a portion that includes both the coupling surface and the drive surface. As shown in FIGS. 70 and 71, the capstan 11710 includes a portion 11715 having a drive surface 11716, which functions as a spool portion. In this embodiment, the drive surface 11716 is within a circular groove defined about a longitudinal axis Ac of the capstan 11710. The drive surface 11716 defines a groove 11722 with a coupling surface 11733, which functions as an anchor portion to secure a cable 11420 to the capstan 11710. The groove 11722 has a zig-zag pattern to further increase the contact surface between the capstan and the cable 11420 to improve retention of the cable 11420 by the capstan 11710. In this embodiment, the cable 11420 is shown wrapped two revolutions around the coupling surface 11733. In alternative embodiments, a cable can be wrapped one time or more than two revolutions around the coupling surface 11733.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys or the like. Further, any of the links, tool members, tension members, or components described herein can be constructed from multiple pieces that are later joined together. For example, in some embodiments, a link can be constructed by joining together separately constructed components. In other embodiments however, any of the links, tool members, tension members, or components described herein can be monolithically constructed.

Although the instruments are generally shown as having an axis of rotation of the tool members (e.g., axis $A_2$) that is normal to an axis of rotation of the wrist member (e.g., axis $A_1$), in other embodiments any of the instruments described herein can include a tool member axis of rotation that is offset from the axis of rotation of the wrist assembly by any suitable angle.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical instrument, comprising:

a shaft comprising a distal end portion and a proximal end portion;

a tool member rotatably coupled to the distal end portion of the shaft about a rotation axis, and comprising a drive pulley and a coupling spool fixedly coupled to the drive pulley, the drive pulley comprising a drive surface;

a mechanical structure coupled to the proximal end portion of the shaft and comprising a first capstan and a second capstan, the first capstan comprising a first portion and a second portion, a first slot and a second slot each defined within the second portion of the first capstan, and the second slot crosses the first slot, the first portion of the first capstan comprising a drive surface, the second capstan comprising a first portion and a second portion, and the first portion of the second capstan comprising a drive surface; and a cable routed along the shaft and comprising a first proximal end, a second proximal end, and a distal portion, the first proximal end of the cable comprising a first wrap portion and a second wrap portion, the second proximal end of the cable comprising a first wrap portion and a second wrap portion, the distal portion of the cable being routed about the drive surface of the drive pulley and being wrapped at least one revolution about the coupling spool to secure the distal portion of the cable to the tool member, the first proximal end of the cable being routed about the drive surface of the first portion of the first capstan, the first proximal end of the cable being wrapped about the second portion of the first capstan within the first slot, and wrapped about the second portion of the first capstan within the second slot such that the second wrap portion of the first proximal end of the cable crosses over the first wrap portion of the first proximal end of the cable, the second proximal end of the cable being routed about the drive surface of the first portion of the second capstan, and the second proximal end of the cable being wrapped about the second portion of the second capstan such that the second wrap portion of the second proximal end of the cable crosses over the first wrap portion of the second proximal end of the cable.

2. The medical instrument of claim 1, wherein:

the cable comprises a polymer.

3. The medical instrument of claim 2, wherein:

the distal portion of the cable is devoid of a retention feature.

4. The medical instrument of claim 1, wherein:

the distal portion of the cable is wrapped at least two revolutions about the coupling spool.

5. The medical instrument of claim 1, wherein:

the distal portion of the cable comprises a first segment and a second segment; and the distal portion of the cable is wrapped about the coupling spool such that the second segment of the distal portion of the cable crosses over the first segment of the distal portion of the cable.

6. The medical instrument of claim 1, wherein:

the first proximal end of the cable is wrapped at least two revolutions about the second portion of the first capstan; and the second proximal end of the cable is wrapped at least two revolutions about the second portion of the second capstan.

7. A medical instrument, comprising:

a shaft comprising a distal end portion and a proximal end portion; and a mechanical structure coupled to the proximal end portion of the shaft, the mechanical structure comprising a capstan, the capstan comprising a first portion and a second portion, the first portion of the capstan comprising a drive surface configured to engage a cable such that rotation of the capstan produces a tension force in the cable, a first slot and a second slot each being defined within the second portion of the capstan, the second slot crossing the first slot, the first slot and the second slot each being configured to receive the cable to secure the cable to the second portion of the capstan, the cable including a first wrap portion and a second wrap portion; and the cable being wrapped about the second portion of the capstan within the first slot and the second slot such that the second wrap portion of the cable crosses over the first wrap portion of the cable.

8. The medical instrument of claim 7, wherein:

the capstan comprises two posts and a third slot defined between the two posts; and the third slot is configured to receive the cable to secure the cable to the second portion of the capstan.

9. The medical instrument of claim 7, wherein:

an opening is defined within the second portion of the capstan;

the cable further comprises a termination end portion; and the termination end portion of the cable is inserted into the opening of the second portion of the capstan.

10. The medical instrument of claim 9, wherein:

the second portion of the capstan comprises a coupling surface; and the cable is wrapped at least two revolutions about the coupling surface of the second portion of the capstan within at least one of the first slot or the second slot.

11. The medical instrument of claim 9, wherein:

the cable is wrapped at least two revolutions about the second portion of the capstan within each of the first slot and the second slot.

12. The medical instrument of claim 9, wherein:

the termination end portion of the cable is devoid of a retention feature.

13. A medical instrument, comprising:

a shaft comprising a distal end portion and a proximal end portion;

an end effector coupled to the distal end portion of the shaft;

a mechanical structure coupled to the proximal end portion of the shaft, the mechanical structure comprising a capstan, the capstan comprising a first portion and a second portion, the first portion of the capstan comprising a drive surface, an opening being defined within the second portion of the capstan, a first slot and a second slot being defined within the second portion of the capstan, and the second slot crossing the first slot; and a cable routed along the shaft and comprising a proximal end portion and a distal portion, the distal portion of the cable being coupled to the end effector, the proximal end portion of the cable comprising a drive portion, a first wrap portion, a second wrap portion, and a termination portion, the drive portion of the proximal end portion of the cable being wrapped at least partially around the drive surface of the first portion of the capstan, the first wrap portion of the proximal end portion of the cable being wrapped about the second portion of the capstan within the first slot, the second wrap portion of the proximal end portion of the cable being wrapped about the second portion of the capstan within the second slot such that the second wrap portion crosses over the first wrap portion, and the termination portion being inserted into the opening of the second portion of the capstan.

14. The medical instrument of claim 13, wherein:

the capstan has a longitudinal axis;

the drive surface of the first portion of the capstan is a circular groove about the longitudinal axis of the capstan and defines a first diameter; and the second portion of the capstan is cylindrical about the longitudinal axis of the capstan and defines a second diameter larger than the first diameter.

15. The medical instrument of claim 14, wherein:

the first portion of the capstan includes a first side wall and a second side wall; and the drive surface of the first portion of the capstan is between the first side wall and the second side wall.

16. The medical instrument of claim 15, wherein:

a passageway is defined within the first side wall; and the first wrap portion of the cable is routed from the first portion of the capstan, through the passageway, and to the first slot.

17. The medical instrument of claim 13, wherein:

the cable comprises a polymer.

18. The medical instrument of claim 13, wherein:

the termination portion of the cable is devoid of a retention feature.

19. The medical instrument of claim 13, wherein:

a central bore is defined within the capstan; and the capstan includes a reinforcing rod within the central bore.

20. The medical instrument of claim 1, wherein:

the first proximal end of the cable is wrapped at least one revolution about the second portion of the first capstan, and the second proximal end of the cable is wrapped at least one revolution about the second portion of the second capstan.

* * * * *